(12) United States Patent
Libutti et al.

(10) Patent No.: US 8,501,912 B2
(45) Date of Patent: Aug. 6, 2013

(54) FILIPIL COMPOSITIONS AND METHODS FOR TREATING CANCER

(75) Inventors: Steven K. Libutti, North Potomac, MD (US); Mjung Kwon, Frederick, MD (US); Anita Tandle, Towson, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 74 days.

(21) Appl. No.: 12/745,279

(22) PCT Filed: Dec. 8, 2008

(86) PCT No.: PCT/IB2008/005015
§ 371 (c)(1),
(2), (4) Date: Oct. 8, 2010

(87) PCT Pub. No.: WO2010/070380
PCT Pub. Date: Jun. 24, 2010

(65) Prior Publication Data
US 2011/0053850 A1   Mar. 3, 2011

Related U.S. Application Data

(60) Provisional application No. 61/005,363, filed on Dec. 3, 2007.

(51) Int. Cl.
*A61K 38/00* (2006.01)
*A61P 35/00* (2006.01)
*C07K 14/00* (2006.01)

(52) U.S. Cl.
USPC ...... 530/350; 424/185.1; 514/13.3; 514/19.2; 530/300

(58) Field of Classification Search
None
See application file for complete search history.

(56) References Cited

U.S. PATENT DOCUMENTS

| | | | |
|---|---|---|---|
| 3,610,795 A | 10/1971 | Antoine |
| 4,016,100 A | 4/1977 | Suzuki et al. |
| 4,089,801 A | 5/1978 | Schneider |
| 4,235,871 A | 11/1980 | Papahadjopoulos et al. |
| 4,342,566 A | 8/1982 | Theofilopoulos et al. |
| 4,485,054 A | 11/1984 | Mezei et al. |
| 4,761,288 A | 8/1988 | Mezei |
| 4,816,567 A | 3/1989 | Cabilly et al. |
| 4,853,228 A | 8/1989 | Wallach et al. |
| 4,868,116 A | 9/1989 | Morgan et al. |
| 4,897,355 A | 1/1990 | Eppstein et al. |
| 4,980,286 A | 12/1990 | Morgan et al. |
| 5,013,497 A | 5/1991 | Yiournas et al. |
| 5,135,917 A | 8/1992 | Burch |
| 5,168,053 A | 12/1992 | Altman et al. |
| 5,176,996 A | 1/1993 | Hogan et al. |
| 5,270,163 A | 12/1993 | Gold et al. |
| 5,294,533 A | 3/1994 | Lupski et al. |
| 5,334,711 A | 8/1994 | Sproat et al. |
| 5,436,330 A | 7/1995 | Taira et al. |
| 5,474,848 A | 12/1995 | Wallach |
| 5,476,766 A | 12/1995 | Gold et al. |
| 5,503,978 A | 4/1996 | Schneider et al. |
| 5,543,293 A | 8/1996 | Gold et al. |
| 5,565,332 A | 10/1996 | Hoogenboom et al. |
| 5,580,737 A | 12/1996 | Polisky et al. |
| 5,580,967 A | 12/1996 | Joyce |
| 5,582,981 A | 12/1996 | Toole et al. |
| 5,595,873 A | 1/1997 | Joyce |
| 5,616,466 A | 4/1997 | Cantor et al. |
| 5,624,824 A | 4/1997 | Yuan et al. |
| 5,627,158 A | 5/1997 | Cho-Chung |
| 5,628,936 A | 5/1997 | Wallach |
| 5,631,115 A | 5/1997 | Ohtsuka et al. |
| 5,631,146 A | 5/1997 | Szostak et al. |
| 5,633,133 A | 5/1997 | Long et al. |
| 5,641,754 A | 6/1997 | Iversen |
| 5,645,985 A | 7/1997 | Froehler et al. |
| 5,646,020 A | 7/1997 | Swiggen et al. |
| 5,646,031 A | 7/1997 | DeYoung et al. |
| 5,646,042 A | 7/1997 | Stinchcomb et al. |
| 5,650,316 A | 7/1997 | Aggarwal et al. |
| 5,652,094 A | 7/1997 | Usman et al. |

(Continued)

FOREIGN PATENT DOCUMENTS

| | | |
|---|---|---|
| EP | 0 045665 | 2/1982 |
| WO | WO 89/07136 | 8/1989 |

(Continued)

OTHER PUBLICATIONS

Bachmann et al. Integrin receptor-targeted transfer peptides for efficient delivery of antisense oligodeoxynucleotides, J Mol. Med, 76, 126-132, 1998.*
Abrahmsén et al., "Engineering subtilisin and its substrates for efficient ligation of peptide bonds in aqueous solution", Biochemistry., Apr. 1991, 30, 30(17), 4151-4159.
Accession No. D00269, *Homo sapiens* gene for tyrosine hydroxylase, partial cds, Jun. 15, 2010.
Acsadi et al., "Human dystrophin expression in mdx mice after intramuscular injection of DNA constructs", Nature., Aug. 1991, 29, 352(6338), 815-818.
Almquist et al., "Synthesis and biological activity of a ketomethylene analogue of a tripeptide inhibitor of angiotensin converting enzyme", J Med Chem., Dec. 1980, 23(12), 1392-1398.
Anthony-Cahill et al., "Site-specific mutagenesis with unnatural amino acids", Trends Biochem Sci., Oct. 1989, 14(10), 400-403.

(Continued)

*Primary Examiner* — Elly-Gerald Stoica
(74) *Attorney, Agent, or Firm* — Woodcock Washburn LLP

(57) ABSTRACT

A purified DOC1 polypeptide comprising a fragment of SEQ ID NO: 1 is provided, wherein the DOC1 polypeptide is not the full-length DOC1 polypeptide sequence. A method of inhibiting angiogenesis in a subject is provided comprising administering to a subject a nucleic acid encoding a DOC1 polypeptide, whereby a cell in the subject produces the DOC1 polypeptide, thus inhibiting angiogenesis. A method of inhibiting tumor growth in a subject is provided comprising administering to a subject a nucleic acid encoding a DOC1 polypeptide, whereby a cell in the subject produces the DOC1 polypeptide, thus inhibiting tumor growth.

8 Claims, 9 Drawing Sheets

U.S. PATENT DOCUMENTS

| | | |
|---|---|---|
| 5,652,107 A | 7/1997 | Lizardi et al. |
| 5,653,996 A | 8/1997 | Hsu |
| 5,683,873 A | 11/1997 | George et al. |
| 5,683,874 A | 11/1997 | Kool |
| 5,683,902 A | 11/1997 | Hampel et al. |
| 5,688,670 A | 11/1997 | Szostak et al. |
| 5,691,317 A | 11/1997 | Cho-Chung |
| 5,693,535 A | 12/1997 | Draper et al. |
| 5,693,773 A | 12/1997 | Kandimalla et al. |
| 5,712,384 A | 1/1998 | Symonds et al. |
| 5,721,367 A | 2/1998 | Kay et al. |
| 5,728,521 A | 3/1998 | Yuan et al. |
| 5,731,295 A | 3/1998 | Draper et al. |
| 5,731,424 A | 3/1998 | Toothman et al. |
| 5,756,291 A | 5/1998 | Griffin et al. |
| 5,770,715 A | 6/1998 | Sugiyama et al. |
| 5,780,228 A | 7/1998 | Parma et al. |
| 5,780,449 A | 7/1998 | Bracht et al. |
| 5,780,607 A | 7/1998 | Goodnow, Jr. et al. |
| 5,780,610 A | 7/1998 | Collins et al. |
| 5,786,138 A | 7/1998 | Swenson |
| 5,786,462 A | 7/1998 | Schneider et al. |
| 5,792,613 A | 8/1998 | Schmidt et al. |
| 5,795,721 A | 8/1998 | Rabin et al. |
| 5,804,440 A | 9/1998 | Burton et al. |
| 5,807,718 A | 9/1998 | Joyce et al. |
| 5,811,300 A | 9/1998 | Sullivan et al. |
| 5,834,185 A | 11/1998 | Ts'o et al. |
| 5,837,243 A | 11/1998 | Deo et al. |
| 5,837,855 A | 11/1998 | Chowrira et al. |
| 5,840,867 A | 11/1998 | Toole et al. |
| 5,846,713 A | 12/1998 | Pagratis et al. |
| 5,849,903 A | 12/1998 | Pietrzkowski et al. |
| 5,856,103 A | 1/1999 | Gray et al. |
| 5,856,188 A | 1/1999 | Hampel et al. |
| 5,856,463 A | 1/1999 | Prydz et al. |
| 5,858,660 A | 1/1999 | Eaton et al. |
| 5,861,254 A | 1/1999 | Schneider et al. |
| 5,861,288 A | 1/1999 | Usman et al. |
| 5,861,501 A | 1/1999 | Benseler et al. |
| 5,864,026 A | 1/1999 | Jensen et al. |
| 5,866,701 A | 2/1999 | Hampel et al. |
| 5,869,246 A | 2/1999 | Matsuo et al. |
| 5,869,248 A | 2/1999 | Yuan et al. |
| 5,869,253 A | 2/1999 | Draper |
| 5,869,339 A | 2/1999 | Hampel et al. |
| 5,869,641 A | 2/1999 | Jayasena et al. |
| 5,874,566 A | 2/1999 | Veerapanane et al. |
| 5,877,021 A | 3/1999 | Stinchcomb et al. |
| 5,877,022 A | 3/1999 | Stinchcomb et al. |
| 5,877,162 A | 3/1999 | Werner et al. |
| 5,891,683 A | 4/1999 | Usman et al. |
| 5,891,684 A | 4/1999 | Usman et al. |
| 5,897,945 A | 4/1999 | Lieber et al. |
| 5,910,408 A | 6/1999 | Szostak et al. |
| 5,919,772 A | 7/1999 | Szyf et al. |
| 5,939,598 A | 8/1999 | Kucherlapati et al. |
| 5,955,590 A | 9/1999 | Levina et al. |
| 5,958,691 A | 9/1999 | Pieken et al. |
| 5,962,426 A | 10/1999 | Glazer |
| 5,972,699 A | 10/1999 | Draper |
| 5,972,704 A | 10/1999 | Draper et al. |
| 5,985,621 A | 11/1999 | Usman et al. |
| 5,989,906 A | 11/1999 | Thompson |
| 5,989,908 A | 11/1999 | Scanlon |
| 5,990,088 A | 11/1999 | Ensoli et al. |
| 5,994,320 A | 11/1999 | Low et al. |
| 5,998,193 A | 12/1999 | Keese et al. |
| 5,998,203 A | 12/1999 | Matulic-Adamic et al. |
| 5,998,602 A | 12/1999 | Torrence et al. |
| 6,001,988 A | 12/1999 | Parma et al. |
| 6,005,095 A | 12/1999 | Capaccioli et al. |
| 6,007,995 A | 12/1999 | Baker et al. |
| 6,013,443 A | 1/2000 | Heilig et al. |
| 6,013,522 A | 1/2000 | Monia et al. |
| 6,017,756 A | 1/2000 | Draper |
| 6,017,898 A | 1/2000 | Pietrzkowski et al. |
| 6,018,042 A | 1/2000 | Mett et al. |
| 6,020,130 A | 2/2000 | Gold et al. |
| 6,022,962 A | 2/2000 | Chowrira et al. |
| 6,025,198 A | 2/2000 | Bennett et al. |
| 6,028,186 A | 2/2000 | Tasset et al. |
| 6,030,776 A | 2/2000 | Eaton et al. |
| 6,033,910 A | 3/2000 | Monia et al. |
| 6,040,296 A | 3/2000 | Nyce |
| 6,046,004 A | 4/2000 | Wu et al. |
| 6,046,319 A | 4/2000 | Power et al. |
| 6,051,698 A | 4/2000 | Janjic et al. |
| 6,057,437 A | 5/2000 | Kamiya et al. |
| 6,096,441 A | 8/2000 | Hauser et al. |
| 6,111,095 A | 8/2000 | Benseler et al. |
| 6,130,364 A | 10/2000 | Jakobovits et al. |
| 6,180,377 B1 | 1/2001 | Morgan et al. |
| 6,261,834 B1 | 7/2001 | Srivastava |
| 6,530,944 B2 | 3/2003 | West et al. |
| 6,759,199 B2 | 7/2004 | Mirkin et al. |
| 2003/0108554 A1* | 6/2003 | Saus et al. .................. 424/155.1 |

FOREIGN PATENT DOCUMENTS

| | | |
|---|---|---|
| WO | WO 90/02806 | 3/1990 |
| WO | WO 91/19813 | 12/1991 |
| WO | WO 92/03566 | 3/1992 |
| WO | WO 92/05285 | 4/1992 |
| WO | WO 92/14843 | 9/1992 |
| WO | WO 93/22434 | 11/1993 |
| WO | WO 94/29348 | 12/1994 |
| WO | WO 95/24489 | 9/1995 |
| WO | WO 97/18312 | 5/1997 |
| WO | WO 98/58057 | 12/1998 |
| WO | WO 98/58058 | 12/1998 |
| WO | WO 00/55180 A2 | 9/2000 |
| WO | WO 02/44321 | 6/2002 |
| WO | WO/03/027263 * | 4/2003 |
| WO | WO/03/048193 * | 6/2003 |

OTHER PUBLICATIONS

Baggiolini et al., "Interleukin-8, a chemotactic and inflammatory cytokine", FEBS Lett., Jul. 1992, 307(1), 97-101.

Bagshawe "The First Bagshawe lecture. Towards generating cytotoxic agents at cancer sites", Br J Cancer., Sep. 1989, 60(3), 275-281.

Banerji et al., "Lymphocyte-specific cellular enhancer is located downstream of the joining region in immunoglobulin heavy chain genes", Cell., Jul. 1983, 33(3), 729-740.

Bangham et al., "Diffusion of univalent ions across the lamellae of swollen phospholipids", J Mol Biol., Aug. 1965, 13(1), 238-252.

Barenholzt et al., "New method for preparation of phospholipid vesicles (liposomes)—French press", FEBS Lett., Mar. 1979, 99(1), 210-214.

Bartel, "Isolation of new ribozymes from a large pool of random sequences [see comment]", Science., Sep. 1993, 261(5127):1411-8.

Battelli et al., "Lymphocyte killing by a xanthine-oxidase-containing immunotoxin" Cancer Immunol Immunother., 1992, 35(6), 421-425.

Batzri et al., "Single bilayer liposomes prepared without sonication" Biochim Biophys Acta., Apr. 1973, 298(4), 1015-1019.

Beck et al., Prolactin antagonist-endostatin fusion protein as a targeted dual-functional therapeutic agent for breast cancer, Cancer Res., Jul. 2003, 63(13), 3598-3604.

Bell et al., "RNA molecules that bind to and inhibit the active site of a tyrosine phosphatase", J Biol Chem., Jun. 1998, 273(23), 14309-14314.

Benner, "Expanding the genetic lexicon: incorporating non-standard amino acids into proteins by ribosome-based synthesis", Trends Biotechnol., May 1994, 12(5), 158-163.

Berkner et al., "Abundant expression of polyomavirus middle T antigen and dihydrofolate reductase in an adenovirus recombinant", J Virol., Apr. 1987, 61(4), 1213-1220.

Bernstein et al., "Role for a bidentate ribonuclease in the initiation step of RNA interference", Nature., Jan. 2001, 409(6818), 363-366.

Blansfield et al., "Combining agents that target the tumor microenvironment improves the efficacy of anticancer therapy", Clin Cancer Res., Jan. 2008, 14(1), 270-280.

Boerner et al., "Production of antigen-specific human monoclonal antibodies from in vitro-primed human splenocytes", J Immunol., Jul. 1991, 147(1), 86-95.

Bout et al., "Lung gene therapy: in vivo adenovirus-mediated gene transfer to rhesus monkey airway epithelium", Hum Gene Ther., Jan. 1994, 5(1), 3-10.

Brigham et al., "Expression of a prokaryotic gene in cultured lung endothelial cells after lipofection with a plasmid vector", Am J Respir Cell Mol Biol., Aug. 1989, 1(2), 95-100.

Brown, "Burlingham BT. Penetration of host cell membranes by adenovirus 2", J Virol., Aug. 1973, 12(2), 386-396.

Brown, "Molecular and cellular mechanisms of receptor-mediated endocytosis", DNA Cell Biol., Jul.-Aug. 1991, 10(6), 399-409.

Brüggemann et al., "Designer mice: the production of human antibody repertoires in transgenic animals", Year Immunol., 1993, 7, 33-40.

Caillaud et al., "Adenoviral vector as a gene delivery system into cultured rat neuronal and glial cells", Eur J Neurosci, Oct. 1993, 5(10), 1287-1291.

Callow, "Thermodynamic modeling and cryomicroscopy of cell-size, unilamellar, and paucilamellar liposomes", Cryobiology., Jun. 1985, 22(3), 251-267.

Carrara et al., "Two helices plus a linker: a small model substrate for eukaryotic RNase P", Proc Natl Acad Sci U S A., Mar. 1995, 92(7), 2627-2631.

Chardonnet, "Early events in the interaction of adenoviruses with HeLa cells. I. Penetration of type 5 and intracellular release of the DNA genome", Virology., Mar. 1970, 40(3), 462-477.

Clark-Lewis et al., "Chemical synthesis, purification, and characterization of two inflammatory proteins, neutrophil activating peptide 1 (interleukin-8) and neutrophil activating peptide", Biochemistry, Mar. 1991, 30(12), 3128-3135.

Clark-Lewis et al., "Structural requirements for interleukin-8 function identified by design of analogs and CXC chemokine hybrids", J Biol Chem., Jun. 1994, 269(23), 16075-16081.

Cole et al. *Monoclonal Antibodies and Cancer Therapy*, Alan R. Liss, p. 77, 1985.

Conrad et al., "In vitro selection of nucleic acid aptamers that bind proteins", Methods Enzymol., 1996, 267, 336-367.

Conrad et al., "Isozyme-specific inhibition of protein kinase C by RNA aptamers", J Biol Chem., Dec. 1994, 269(51), 32051-32054.

Convery et al., "Crystal structure of an RNA aptamer-protein complex at 2.8 A resolution", Nat Struct Biol., Feb. 1998, 5(2), 133-139.

Cotter, "Robertson ES. Molecular genetic analysis of herpesviruses and their potential use as vectors for gene therapy applications", Curr Opin Mol Ther., Oct. 1999, 1(5), 633-644.

Creighton, "Proteins: Structure and Molecular Properties", W. H. Freeman & Co., San Francisco., 1983, 79-86.

DATABASE Geneseq [Online] Aug. 12, 2003, "Human CGDD-51 protein." XP002589628 retrieved from EBI accession No. GSP:ABR69651 Database accession No. ABR69651.

Davidson, "Overproduction of polyomavirus middle T antigen in mammalian cells through the use of an adenovirus vector", J Virol., Apr. 1987, 61(4), 1226-1239.

Dawson, et al., "Synthesis of proteins by native chemical ligation", Science, Nov. 1994, 266(5186), 776-779.

Deamer et al., "Large volume liposomes by an ether vaporization method", Biochim Biophys Acta., Sep. 1976, 443(3), 629-634.

DeLisle Milton et al., Techniques in Protein Chemistry IV. Academic Press, New York, 1992, 257-267.

Eaton et al., "Let's get specific: the relationship between specificity and affinity", Chem Biol., Oct. 1995, 2(10), 633-638.

Elbashir et al., "Duplexes of 21-nucleotide RNAs mediate RNA interference in cultured mammalian cells", Nature., May 2001, 411(6836), 494-498.

Elbashir et al., "RNA interference is mediated by 21- and 22-nucleotide RNAs", Genes Dev., Jan. 2001, 15(2), 188-200.

Ellington "In vitro selection of RNA molecules that bind specific ligands", Nature., Aug. 1990, 346(6287), 818-822.

Ellington et al., "An RNA groove", Nat Struct Biol., Dec. 1996, 3(12), 981-984.

Famulok et al., "Aptamers as tools in molecular biology and immunology", Curr Top Microbiol Immunol., 1999, 243, 123-136.

Felgner et al., "Lipofection: a highly efficient, lipid-mediated DNA-transfection procedure", Proc Natl Acad Sci U S A., Nov. 1987, 84(21), 7413-7417.

Fiers et al., "Complete nucleotide sequence of SV40 DNA", Nature., May 1978, 273(5658), 113-120.

Fire et al., "Potent and specific genetic interference by double-stranded RNA in *Caenorhabditis elegans*", Nature, Feb. 1998, 391(6669), 806-811.

Forster, "External guide sequences for an RNA enzyme", Science., Aug. 1990, 249(4970), 783-786.

Gao et al., "Quantum-dot nanocrystals for ultrasensitive biological labeling and multicolor optical encoding", J Biomed Opt., Oct. 2002, 7(4), 532-537.

GenBank Accession No. NP_001035924.1, filamin A-interacting protein 1-like isoform 3 [*Homo sapiens*], Feb. 13, 2011.

GenBank Accession No. NP_055705 filamin A-interacting protein 1-like isoform 2 [*Homo sapiens*], Feb. 10, 2011.

GenBank Accession No. NP_055705.2 filamin A-interacting protein 1-like isoform 3 [*Homo sapiens*], Feb. 10, 2011.

GenBank Accession No. NP_878913.2 filamin A-interacting protein 1-like isoform 1 [*Homo sapiens*]. Feb. 19, 2011.

Genbank Accession No. XM_002964, *Homo sapiens* downregulated in ovarian cancer 1 (DOC 1) mRNA, Aug. 1, 2002.

Giaever et al., "A morphological biosensor for mammalian cells", Nature., Dec. 1993, 366(6455), 591-592.

Giver et al., "Selective optimization of the Rev-binding element of HIV-1", Nucleic Acids Res., Nov. 1993, 21(23), 5509-5516.

Gómez-Foix et al., "Adenovirus-mediated transfer of the muscle glycogen phosphorylase gene into hepatocytes confers altered regulation of glycogen metabolism", J Biol Chem., Dec. 1992, 267(35), 25129-25134.

Green et al., "Nuclease-resistant nucleic acid ligands to vascular permeability factor/vascular endothelial growth factor", Chem Biol., Oct. 1995, 2(10), 683-695.

Greenaway et al., "Human cytomegalovirus DNA: BamHI, EcoRI and PstI restriction endonuclease cleavage maps", Gene., Jun. 1982, 18(3), 355-360.

Guzman et al., "Efficient gene transfer into myocardium by direct injection of adenovirus vectors", Circ Res., Dec. 1993, 73(6), 1202-1207.

Haj-Ahmad et al., "Development of a helper-independent human adenovirus vector and its use in the transfer of the herpes simplex virus thymidine kinase gene", J Virol., Jan. 1986, 57(1), 267-274.

Hajitou et al., "A hybrid vector for ligand-directed tumor targeting and molecular imaging", Cell., Apr. 2006, 125(2), 385-398.

Hajitou et al., "Design and construction of targeted AAVP vectors for mammalian cell transduction", Nat Protoc., 2007, 2(3), 523-531.

Hammond et al., "An RNA-directed nuclease mediates post-transcriptional gene silencing in *Drosophila* cells", Nature., Mar. 2000, 404(6775), 293-296.

Han et al., "Quantum-dot-tagged microbeads for multiplexed optical coding of biomolecules", Nat Biotechnol., Jul. 2001, 19(7), 631-635.

Hann, "On the double bond isostere of the peptide bond: preparation of an enkephalin analogue", J. Chem. Soc Perkin Trans. 1982, I 307-314.

Hannon, "RNA interference", Nature., Jul. 2002, 418(6894), 244-251.

Hesselberth et al., "In vitro selection of nucleic acids for diagnostic applications", J Biotechnol., Mar. 2000, 74(1), 15-25.

Hirao et al., "The limits of specificity: an experimental analysis with RNA aptamers to MS2 coat protein variants", Mol Divers., 1998-1999, 4(2), 75-89.

Holladay et al. "Synthesis of Hydroxyethylene and ketomethyleve Dipeptide Isosteres", Tetrahedron. Lett 24, 1983, 4401-4404.

Homann et al., "Combinatorial selection of high affinity RNA ligands to live African trypanosomes", Nucleic Acids Res., May 1999, 27(9), 2006-2014.

Hoogenboom et al.,"By-passing immunisation. Human antibodies from synthetic repertoires of germline VH gene segments rearranged in vitro", J Mol Biol., Sep. 1992, 227(2), 381-388.

Hruby, "Conformational restrictions of biologically active peptides via amino acid side chain groups", Life Sci., Jul. 1982, 31(3), 189-199.

Hudson et al., "Methionine enkephalin and isosteric analogues. I. Synthesis on a phenolic resin support", Int J Pept Protein Res., 1979, 14(3), 177-185.

Hughes et al., "Monoclonal antibody targeting of liposomes to mouse lung in vivo", Cancer Res., Nov. 1989, 49(22), 6214-6220.

Ibba et al., "Towards engineering proteins by site-directed incorporation in vivo of non-natural amino acids", Biotechnology (N Y)., Jul. 1994, 12(7), 678-682.

Ibba, "Strategies for in vitro and in vivo translation with non-natural amino acids", Biotechnology & Genetic Engineering Reviews, 1995, 13,197-216.

Itakura et al., "Synthesis and use of synthetic oligonucleotides", Annu Rev Biochem., 1984, 53, 323-356.

Jaeger et al., "Improved predictions of secondary structures for RNA", Proc Natl Acad Sci U S A., Oct. 1989, 86(20), 7706-7770.

Jaeger et al., "Predicting optimal and suboptimal secondary structure for RNA", Methods Enzymol., 1990, 183, 281-306.

Jakobovits et al., "Analysis of homozygous mutant chimeric mice: deletion of the immunoglobulin heavy-chain joining region blocks B-cell development and antibody production", Proc Natl Acad Sci U S A., Mar. 1993, 90(6), 2551-2555.

Jellinek et al., "High-affinity RNA ligands to basic fibroblast growth factor inhibit receptor binding", Proc Natl Acad Sci U S A., Dec. 1993, 90(23), 11227-11231.

Jellinek et al., "Inhibition of receptor binding by high-affinity RNA ligands to vascular endothelial growth factor", Biochemistry., Aug. 1994, 33(34, 10450-10456.

Jellinek et al., "Potent 2'-amino-2'-deoxypyrimidine RNA inhibitors of basic fibroblast growth factor", Biochemistry., Sep. 1995, 34(36), 11363-11372.

Jennings-White et al. "Synthesis of Ketomethylene Analogs of Dipeptides", Tetrahedron Lett., 1982, 23, 2533-2534.

Jones et al., "Replacing the complementarity-determining regions in a human antibody with those from a mouse", Nature., May 29-Jun. 4, 1986, 321(6069), 522-525.

Joyce, "Amplification, mutation and selection of catalytic RNA. Gene", Oct. 1989, 82(1), 83-87.

Keese et al., "Electrical wound-healing assay for cells in vitro", Proc Natl Acad Sci U S A., Feb. 2004, 101(6), 1554-1559.

Kim et al., "Preparation of multivesicular liposomes", Biochim Biophys Acta., Mar. 1983, 728(3), 339-348.

Kirpotin et al., "Sterically stabilized anti-HER2 immunoliposomes: design and targeting to human breast cancer cells in vitro", Biochemistry., Jan. 1997, 36(1), 66-75.

Kirshenbaum et al., "Highly efficient gene transfer into adult ventricular myocytes by recombinant adenovirus", J Clin Invest., Jul. 1993, 92(1), 381-387.

Klener et al., "Insights into gene expression changes impacting B-cell transformation: cross-species microarray analysis of bovine leukemia virus tax-responsive genes in ovine B cells", J Virol., Feb. 2006, 80(4), 1922-1938.

Köhler et al., "Continuous cultures of fused cells secreting antibody of predefined specificity", Nature., Aug. 1975, 256(5517):, 495-497.

Kunkel et al., "Rapid and efficient site-specific mutagenesis without phenotypic selection" Methods Enzymol., 1987, 154, 367-382.

Kwon, Mijung et al. "Functional characterization of filamin A interacting protein 1-like, a novel candidate for antivascular cancer therapy" Cancer Research, Sep. 1 2008, 68(18), 7332-7341.

Laimins et al., "Osmotic control of kdp operon expression in *Escherichia coli*", Proc Natl Acad Sci U S A., Jan. 1981, 78(1), 464-468.

Le Gal et al., "An adenovirus vector for gene transfer into neurons and glia in the brain", Science., Feb. 1993, 259(5097), 988-990.

Letsinger et al., "Cholesteryl-conjugated oligonucleotides: synthesis, properties, and activity as inhibitors of replication of human immunodeficiency virus in cell culture", Proc Natl Acad Sci U S A., Sep. 1989, 86(17), 6553-6556.

Lin, et al., "Photonic pseudo-gap-based modification of photoluminescence from CdS nancrystal satellites around polymer microspheres in a photonic crystal", Appl. Phys Lett., 2002, 81, 3134.

Litzinger et al., "Biodistribution and immunotargetability of ganglioside-stabilized dioleoylphosphatidylethanolamine liposomes", Biochim Biophys Acta., Feb. 1992, 1104(1), 179-187.

Lusky et al., "Bovine papilloma virus contains an activator of gene expression at the distal end of the early transcription unit", Mol Cell Biol., Jun. 1983, 3(6), 1108-1122.

Marks et al., "By-passing immunization. Human antibodies from V-gene libraries displayed on phage", J Mol Biol., Dec. 1991, 222(3), 581-597.

Martinez et al., "Single-stranded antisense siRNAs guide target RNA cleavage in RNAi", Cell., Sep. 2002, 110(5), 563-574.

Massie et al., "Construction of a helper-free recombinant adenovirus that expresses polyomavirus large T antigen", Mol Cell Biol., Aug. 1986, 6(8), 2872-2883.

Mastrobattista et al., "Immunoliposomes for the targeted delivery of antitumor drugs", Adv Drug Deliv Rev., Nov. 1999, 40(1-2), 103-127.

Mazzanti et al., "Early genetic mechanisms underlying the inhibitory effects of endostatin and fumagillin on human endothelial cells", Genome Res., Aug. 2004, 14(8), 1585-1593.

Mok et al., "Molecular cloning of differentially expressed genes in human epithelial ovarian cancer", Gynecol Oncol., Feb. 1994, 52(2), 247-252.

Morley, "K+ channel openers and suppression of airway hyperreactivity", Trends Pharmacol Sci., Dec. 1994, 15(12), 463-468.

Morrison et al., "Chimeric human antibody molecules: mouse antigen-binding domains with human constant region domains", Proc Natl Acad Sci U S A., Nov. 1984, 81(21), 6851-6855.

Morsy et al., "Efficient adenoviral-mediated ornithine transcarbamylase expression in deficient mouse and human hepatocytes", J Clin Invest., Sep. 1993, 92(3), 1580-1586.

Moullier et al., "Correction of lysosomal storage in the liver and spleen of MPS VII mice by implantation of genetically modified skin fibroblasts", Nat Genet., Jun. 1993, 4(2), 154-159.

Mulligan et al., "Expression of a bacterial gene in mammalian cells", Science., Sep. 1980, 209(4463), 1422-1427.

Mulligan, "The basic science of gene therapy", Science., May 1993, 260(5110), 926-932.

Napoli et al., "Introduction of a Chimeric Chalcone Synthase Gene into Petunia Results in Reversible Co-Suppression of Homologous Genes in trans", Plant Cell., Apr. 1990, 2(4), 279-289.

Narang et al., "Chemical synthesis of deoxyoligonucleotides by the modified triester method", Methods Enzymol., 1980, 65(1), 610-620.

Needleman, "A general method applicable to the search for similarities in the amino acid sequence of two proteins", J. Mol Biol., Mar. 1970, 48, 443-453.

Nielsen et al., "Peptide nucleic acid (PNA). A DNA mimic with a peptide backbone", Bioconjug Chem., Jan.-Feb. 1994, 5(1), 3-7.

Nykänen et al., "ATP requirements and small interfering RNA structure in the RNA interference pathway", Cell., Nov. 2001, 107(3), 309-321.

Osborne et al., "Aptamers as therapeutic and diagnostic reagents: problems and prospects", Curr Opin Chem Biol., Jun. 1997, 1(1), 5-9.

Osborne et al., "Transcription control region within the protein-coding portion of adenovirus E1A genes", Mol Cell Biol., Jul. 1984, 4(7), 1293-1305.

Pai, et al., "Microscopic flow visualization system for fluids in magnetic field", Mag. & Magnetic Mater., 1999, 194, 262-266.

Papahadjopoulos et al., "Surface properties of acidic phospholipids: interaction of monolayers and hydrated liquid srystals with uni- and bi-valent metal ions", Biochim et Biophys Acta, Sep. 1968, 135, 238-254.

Pearson et al., "Improved tools for biological sequence comparison", Proc Natl Acad Sci USA., Apr. 1988, 85(8), 2444-2448.

Pietersz et al., "Antibody conjugates for the treatment of cancer", Immunol Rev., Oct. 1992, 129, 57-80.

Poole et al., "Altered patterns of cellular gene expression in dermal microvascular endothelial cells infected with Kaposi's sarcoma-associated herpesvirus", J Virol., Apr. 2002, 76(7), 3395-3420.

Presta, "Antibody engineering", Curr. Opin. Struct. Biol., Aug. 1992, 2, 593-596.

Ragot et al., "Replication-defective recombinant adenovirus expressing the Epstein-Barr virus (EBV) envelope glycoprotein gp340/220 induces protective immunity against EBV-induced lymphomas in the cottontop tamarin", J Gen Virol., Mar. 1993, 74 ( Pt 3), 501-507.

Rajarathnam et al., "1H NMR studies of interleukin 8 analogs: characterization of the domains essential for function", Biochemistry., May 1994, 33(21), 6623-6630.
Ram et al., "In situ retroviral-mediated gene transfer for the treatment of brain tumors in rats", Cancer Res., Jan. 1993, 53(1), 83-88.
Rich et al., "Development and analysis of recombinant adenoviruses for gene therapy of cystic fibrosis", Hum Gene Ther., Aug. 1993, 4(4), 461-476.
Riechmann et al., "Reshaping human antibodies for therapy", Nature., Mar. 1988, 332(6162), 323-327.
Rizo et al., "Constrained peptides: models of bioactive peptides and protein substructures", Annu Rev Biochem., 1992, 61, 387-418.
Roessler et al., "Adenoviral-mediated gene transfer to rabbit synovium in vivo", J Clin Invest., Aug. 1993, 92(2), 1085-1092.
Roffler et al., "Anti-neoplastic glucuronide prodrug treatment of human tumor cells targeted with a monoclonal antibody-enzyme conjugate", Biochem Pharmacol., Oct. 1991, 42(10), 2062-2065.
Sambrook et al., Molecular Cloning: A Laboratory Manual, 2nd Edition (Cold Spring Harbor Laboratory Press, Cold Spring Harbor, N.Y., 1989) Chapters 5, 6.
Schnölzer et al., "Constructing proteins by dovetailing unprotected synthetic peptides: backbone-engineered HIV protease", Science., Apr. 1992, 256(5054), 221-225.
Schwarze et al. "Novel pathways associated with bypassing cellular senescence in human prostate epithelial cells" J. Urology, Apr. 1, 2002, 167(4 Suppl), p. 139.
Schwarze et al., "Novel pathways associated with bypassing cellular senescence in human prostate epithelial cells", J Biol Chem., Apr. 2002, 277(17), 14877-14883.
Schwarze et al., "The identification of senescence-specific genes during the induction of senescence in prostate cancer cells", Neoplasia., Sep. 2005, 7(9), 816-823.
Senter et al., "Generation of 5-fluorouracil from 5-fluorocytosine by monoclonal antibody-cytosine deaminase conjugates", Bioconjug Chem., Nov.-Dec. 1991, 2(6), 447-451.
Senter et al., "Generation of cytotoxic agents by targeted enzymes", Bioconjug Chem., Jan.-Feb. 1993, 4(1), 3-9.
Seth et al., "Evidence that the penton base of adenovirus is involved in potentiation of toxicity of *Pseudomonas* exotoxin conjugated to epidermal growth factor", Mol Cell Biol., Aug. 1984, 4(8), 1528-1533.
Seth et al., "Role of a low-pH environment in adenovirus enhancement of the toxicity of a *Pseudomonas* exotoxin-epidermal growth factor conjugate", J Virol., Sep. 1984, 51(3), 650-655.
Smith et al., "Comparison of Biosequences", Adv. Appl. Math., 1981, 2, 482-489.
Soghomonyan et al., "Molecular PET imaging of HSV1-tk reporter gene expression using [18F]FEAU", Nat Protoc., 2007, 2(2), 416-423.
Southern et al., "Transformation of mammalian cells to antibiotic resistance with a bacterial gene under control of the SV40 early region promoter", J Mol Appl Genet., 1982, 1(4), 327-341.
Spatola et al., "Structure-activity relationships of enkephalins containing serially replaced thiomethylene amide bond surrogates", Life Sci., Apr. 1986, 38(14), 1243-1249.
Spatola, in *Chemistry and Biochemistry of Amino Acids, Peptides, and Proteins*, Ch. 5, Peptide Backbone Modifications, B. Weinstein, eds., Marcel Dekker, New York, 1983, 267-357.
Sudimack et al., "Targeted drug delivery via the folate receptor", Adv Drug Deliv Rev., Mar. 2000, 41(2), 147-162.
Sugden et al., "A vector that replicates as a plasmid and can be efficiently selected in B-lymphoblasts transformed by Epstein-Barr virus", Mol Cell Biol., Feb. 1985, 5(2), 410-413.
Sun et al., "Human artificial episomal chromosomes for cloning large DNA fragments in human cells", Nat Genet., Sep. 1994, 8(1), 33-41.
Svensson "Role of vesicles during adenovirus 2 internalization into HeLa cells", J Virol., Aug. 1985, 55(2), 442-449.

Tandle et al., "Endothelial monocyte activating polypeptide-II induced gene expression changes in endothelial cells", Cytokine., Jun. 2005, 30(6), 347-358.
Thorson et al., "A biosynthetic approach for the incorporation of unnatural amino acids into proteins", Methods Mol Biol., 1998, 77, 43-73.
Tkachenko et al., "Multifunctional gold nanoparticle-peptide complexes for nuclear targeting", J Am Chem Soc., Apr. 2003, 125(16), 4700-4701.
Todd, R. et al. "Deleted in oral cancer-1 (doc-1), a novel oral tumor suppressor gene" FASEB Journal, Oct. 9, 1995, vol. 9, 1362-1370.
Tsai et al., "In vitro selection of an RNA epitope immunologically cross-reactive with a peptide", Proc Natl Acad Sci U S A., Oct. 1992, 89(19), 8864-8868.
Tuerk et al., "RNA pseudoknots that inhibit human immunodeficiency virus type 1 reverse transcriptase", Proc Natl Acad Sci U S A., Aug. 1992, 89(15), 6988-6992.
Tuerk et al., "Systematic evolution of ligands by exponential enrichment: RNA ligands to bacteriophage T4 DNA polymerase", Science., Aug. 1990, 249(4968), 505-510.
Ui-Tei et al., "Sensitive assay of RNA interference in *Drosophila* and Chinese hamster cultured cells using firefly luciferase gene as target", FEBS Lett., Aug. 2000, 479(3), 79-82.
Varga et al., "Infectious entry pathway of adenovirus type 2", J Virol., Nov. 1991, 65(11), 6061-6070.
Verhoeyen et al., "Reshaping human antibodies: grafting an antilysozyme activity", Science., Mar. 1988, 239(4847), 1534-1536.
Verma, Retroviral vectors for gene transfer. In Microbiology—1985, American Society for Microbiology, Washington, 1985, 229-232.
Vyas et al., "Endogenous carriers and ligands in non-immunogenic site-specific drug delivery", Adv Drug Deliv Rev., Sep. 2000, 43(2-3), 101-164.
Wang et al., "Lithium Niobate Inverse Opals Prepared by Templating Colloidal Crystals of Polyelectrolyte-Coated Particles", Chem. Mater. 2003, 15, 2724.
Weder, et al. In "Liposome Technology", ed. G. Gregoriadis, CRC Press Inc., Boca Raton, Fla., 1984, 1, chapter 7, 79-107.
Weiss et al., "RNA aptamers specifically interact with the prion protein PrP", J Virol., Nov. 1997, 71(11), 8790-8797.
Wickham et al., "Integrins alpha v beta 3 and alpha v beta 5 promote adenovirus internalization but not virus attachment", Cell., Apr. 1993, 73(2), 309-319.
Wolff et al., "Direct gene transfer into mouse muscle in vivo", Science., Mar. 1990, 247(4949 Pt 1), 1465-1468.
Xu et al.,"Anti-peptide aptamers recognize amino acid sequence and bind a protein epitope", Proc Natl Acad Sci U S A., Jul. 1996, 93(15), 7475-7480.
Yuan et al., "Targeted cleavage of mRNA by human RNase P", Proc Natl Acad Sci U S A., Sep. 1992, 89(17), 8006-8010.
Yuan et al.,"Substrate recognition by human RNase P: identification of small, model substrates for the enzyme", EMBO J., Jan. 1995, 14(1), 159-168.
Zabner et al., "Adenovirus-mediated gene transfer transiently corrects the chloride transport defect in nasal epithelia of patients with cystic fibrosis", Cell., Oct. 1993, 75(2), 207-216.
Zabner et al., "Safety and efficacy of repetitive adenovirus-mediated transfer of CFTR cDNA to airway epithelia of primates and cotton rats", Nat Genet., Jan. 1994, 6(1), 75-83.
Zhang et al., "Generation and identification of recombinant adenovirus by liposome-mediated transfection and PCR analysis", Biotechniques., Nov. 1993, 15(5), 868-872.
Zoller, "New recombinant DNA methodology for protein engineering", Curr Opin Biotechnol., Aug. 1992, 3(4), 348-354.
Zuker, "On finding all suboptimal foldings of an RNA molecule", Science., Apr. 1989, 244(4900), 48-52.

* cited by examiner

FILIP1L COMPOSITIONS AND METHODS FOR TREATING CANCER

CROSS-REFERENCE TO RELATED APPLICATIONS

This application is the National Stage of International Application No. PCT/IB2008/005015, filed Dec. 8, 2008, which claims the benefit of U.S. Provisional Application No. 61/005,363, filed Dec. 3, 2007. The aforementioned applications are incorporated herein by reference in their entireties for all purposes.

BACKGROUND

Angiogenesis, the process of the formation of new blood vessels from pre-existing capillaries, is required for the sustained growth, invasion and spread of tumors. Thus, the inhibition of tumor angiogenesis has been considered to be one of the important targets in anticancer therapy. Utilizing cDNA microarray analysis, it has been demonstrated that the expression of genes such as DOC1, KLF4 and TC-1 was rapidly modulated by the angiogenesis inhibitors, endostatin and fumagillin. In addition, DOC1 (downregulated in ovarian cancer 1; also known as FILIP1L (filamin A interacting protein 1-like)) was shown to be an upstream regulator of KLF4 and TC-1 following endostatin treatment (Mazzanti C M et al. Genome Res (2004) 14:1585). Expression of DOC1 was rapidly regulated by another angiogenesis inhibitor EMAP II (Tandle A T et al. Cytokine (2005) 30:347). DOC1 mRNA expression has been shown to be consistently absent in ovarian carcinoma cells (Mok S C et al. Gynecol Oncol (1994) 52:247). In addition, it has been shown to be induced in senescent human prostate epithelial cells, but significantly repressed in immortalized prostate epithelial cells (Schwarze S R et al. J Biol Chem (2002) 277:14877; and Schwarze S R et al. Neoplasia (2005) 7:816). Furthermore, DOC1 mRNA expression was shown to be downregulated in microvascular endothelial cells infected with Kaposi's sarcoma-associated herpesvirus as well as during B-cell transformation (Poole L I et al. J Virol (2002) 76:3395 7; and Klener P et al. J Virol (2006) 80:1922). The function of DOC1, however, is completely unknown.

BRIEF SUMMARY

In accordance with the purpose of this invention, as embodied and broadly described herein, this invention relates to compositions and methods for treating cancer using DOC1 (FILIP1L) and DOC1 polypeptides.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION

Figure 1A:
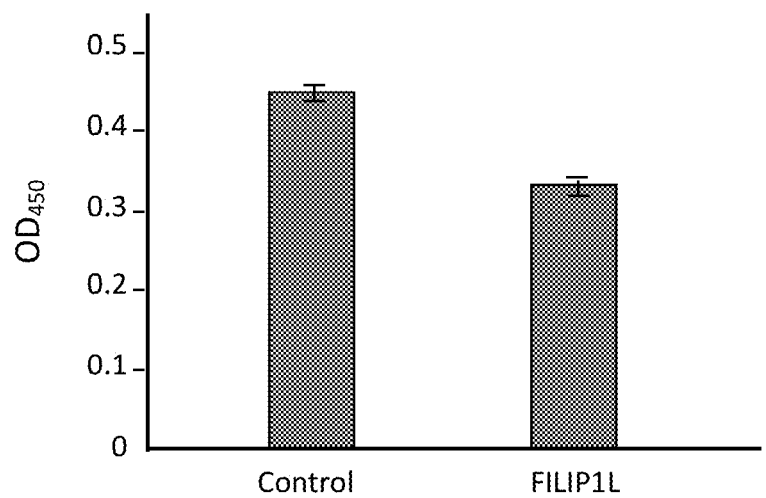
FIG. 1 shows that overexpression of FILIP1L in endothelial cells leads to inhibition of cell proliferation and increase in apoptosis (A) Inhibition of cell proliferation by overexpression of FILIP1L in HUVECs (human umbilical vein endothelial cells) was analyzed by BrdU ELISA 24 h after transfection. Error bars indicate SEM (n=4, P<0.0001). The result is a representative of three independent experiments. (B) Increased apoptosis by overexpression of FILIP1L in HUVECs was analyzed by annexin V-FITC and 7-AAD staining followed by flow cytometry analysis 48 h after transfection. The numbers 15.2 for control and 44.4 for FILIP1L indicate the percentage of cells in late apoptosis. The result is a representative of two independent experiments.

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a DOC1 polypeptide or nucleic acid (e.g., DOC1 wild-type, variant 2, isoform 1 or isoform 4) is disclosed and discussed and a number of modifications that can be made to a number of molecules including the DOC1 polypeptide or nucleic acid (e.g., DOC1 wild-type, variant 2, isoform 1 or isoform 4) are discussed, each and every combination and permutation of DOC1 polypeptide or nucleic acid (e.g., DOC1 wild-type, variant 2, isoform 1 or isoform 4) and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

A. Definitions

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents.

It must be noted that as used herein and in the appended claims, the singular forms "a," "an," and "the" include plural reference unless the context clearly dictates otherwise. Thus, for example, reference to "a cell" includes a plurality of such cells; reference to "the DOC1 polypeptide" is a reference to one or more DOC1 polypeptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps.

The term "preventing" as used herein refers to administering a compound prior to the onset of clinical symptoms of a disease or conditions so as to prevent a physical manifestation of aberrations associated with the disease or condition.

The term "treating" as used herein refers to administering a compound after the onset of clinical symptoms. Treating can include a partial improvement in symptoms (e.g., a reduction in tumor size or in the number of tumors or a slowing of tumor growth), or may be a complete cessation of symptoms (e.g., eradication of any cancer).

The term "in need of treatment" as used herein refers to a judgment made by a caregiver (e.g. physician, nurse, nurse practitioner, or individual in the case of humans; veterinarian in the case of animals, including non-human mammals) that an individual or animal requires or will benefit from treatment. This judgment is made based on a variety of factors that are in the realm of a care giver's expertise, but that include the knowledge that the individual or animal is ill, or will be ill, as the result of a condition that is treatable by the compounds of the invention. A similar judgment may be mad by a caregiver to determine if a subject (individual) is "in need of prevention."

The terms "individual" and "subject" as used herein refer to a mammal, including animals, preferably mice, rats, other rodents, rabbits, dogs, cats, swine, cattle, sheep, horses, or primates, particularly humans.

The terms "higher," "increases," "elevates," or "elevation" refer to increases above basal levels, e.g., as compared to a control. The terms "low," "lower," "reduces," or "reduction" refer to decreases below basal levels, e.g., as compared to a control.

"Anti-angiogenic" as used herein means either the prevention of or a reduction in the growth of new blood vessels, or a reduction in existing vessels, e.g., via necrosis, or both.

B. Compositions

1. Functional DOC1 Polypeptides

Provided is a purified DOC1 (also referred to as FILIP1L) polypeptide comprising a fragment of SEQ ID NO:1, wherein the DOC1 polypeptide is not the full-length DOC1 protein disclosed in that sequence. SEQ ID NO:1 is the wild-type DOC1 protein sequence also known as isoform 2, and found under GenBank Accession No. NP_055705.2. Provided is a purified DOC1 (also referred to as FILIP1L) polypeptide comprising a fragment of SEQ ID NO:2 (also known as variant 2, also formerly found under GenBank Accession No. NP_055705) wherein the DOC1 polypeptide is not the full-length DOC1 protein disclosed in that sequence. Provided is a purified DOC1 (also referred to as FILIP1L) polypeptide comprising a fragment of SEQ ID NO:3 (also know as isoform 1, and found under GenBank Accession No. NP_878913.2) wherein the DOC1 polypeptide is not the full-length DOC1 protein disclosed in that sequence. Provided is a purified DOC1 (also referred to as FILIP1L) polypeptide comprising a fragment of SEQ ID NO:4 (also known as isoform 3, and found under GenBank Accession No. NP_001035924.1) wherein the DOC1 polypeptide is not the full-length DOC1 protein disclosed in that sequence. Thus, the FILIP1L protein referred to herein can be the protein found under Accession Nos. NP_055705.2, NP_001035924.1, NP_878913.2, and NP_055705. The FILIP1L polypeptide sequences, nucleic acid sequences encoding FILIP1L, and the additional information set forth under GenBank Accession Nos. NP_055705.2, NP_001035924.1, NP_878913.2, and NP_055705 are hereby incorporated by reference.

Provided is a purified DOC1 (also referred to as FILIP1L) polypeptide comprising a fragment of SEQ ID NO:1, wherein the DOC1 polypeptide is not the full-length DOC1 protein disclosed in that sequence, and the fragment is at least 400 amino acids in length. Provided is a purified DOC1 (also referred to as FILIP1L) polypeptide comprising a fragment of SEQ ID NO:1, wherein the DOC1 polypeptide is not the full-length DOC1 protein disclosed in that sequence, with the proviso that the fragment does not consist of amino acids 3-32, 3-52, 43-52, or 510-893 of SEQ ID NO:1. A purified DOC1 polypeptide comprising a fragment of SEQ ID NO: 2, wherein the DOC1 polypeptide is not the full-length DOC1 polypeptide sequence, and the fragment is at least 51 amino acids in length. Also provided is a purified DOC1 polypeptide comprising a fragment of SEQ ID NO: 3, wherein the DOC1 polypeptide is not the full-length DOC1 polypeptide sequence, and the fragment is at least 51 amino acids in length. Also provided is a purified DOC1 polypeptide comprising a fragment of SEQ ID NO: 4, wherein the DOC1 polypeptide is not the full-length DOC1 polypeptide sequence, and the fragment is at least 400 amino acids in length. Also provided is a purified DOC1 polypeptide comprising a fragment of SEQ ID NO: 1, wherein the DOC1 polypeptide is not the full-length DOC1 polypeptide sequence, and the fragment comprises amino acids 127-512 of SEQ ID NO:1.

The disclosed DOC1 polypeptide can comprise at least 10 contiguous amino acids of DOC1 (e.g., DOC1 of SEQ ID NO:1, DOC1 of SEQ ID NO:2, DOC1 of SEQ ID NO:3 or DOC1 of SEQ ID NO:4) and can range up to 751 contiguous amino acids (for fragments on SEQ ID NO:2), 892 contiguous amino acids (for fragments on SEQ ID NO:1), 1132 contiguous amino acids (for fragments on SEQ ID NO:4) or 1134 contiguous amino acids (for fragments on SEQ ID NO:3) of DOC1, including every number of amino acids in between. For example, the fragment of DOC1 can be up to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100; 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400; 20, 40, 60, 80, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 710, 720, 730, 740, 750, 760, 770, 780, 790, 800, 810, 820, 839, 840, 850, 860, 870, 880, 890, 900, 910, 920, 930, 940, 950, 960, 970, 980, 990, 1000, 1010, 1020, 1030, 1040, 1050, 1060, 1080, 1090, 1100, 1110, 1120 or 1130 amino acids in length. A fragment of a reference protein/polypeptide has a sequence that is identical to a region of the reference protein. As used herein, a fragment of DOC1 is a subpart of DOC1. Thus, it does not include any variation in the amino acid sequence of DOC1 (e.g., SEQ ID NO:1), but is only shorter than the native DOC1 polypeptide.

In one aspect, the DOC1 polypeptide has one or more functions of full-length DOC1, that is, it is a functional fragment of DOC1.

For example, the DOC1 polypeptide can have the anti-angiogenic function of native DOC1. Angiogenesis is a process where blood vessels are formed from existing blood vessels. This involves proliferation, differentiation and migration of endothelial cells and possibly other cells found in the vasculature, such as smooth muscle cells and fibroblasts. Anti-angiogenic function also includes a reduction in existing vessels, for example, via necrosis of existing vessels. Alteration of this process, either its potentiation or its inhibition, can have benefits be beneficial for the therapy or treatment of human diseases, such as cancer, macular degeneration, rheumatoid arthritis, Alzheimer's disease, wound healing, atherosclerosis and ischemia.

Alternatively or in addition the DOC1 polypeptide can have the apoptotic activity of native DOC1.

Alternatively or in addition the DOC1 polypeptide can have anti-tumor (anti-proliferative) activity of native DOC1.

Figure 3:
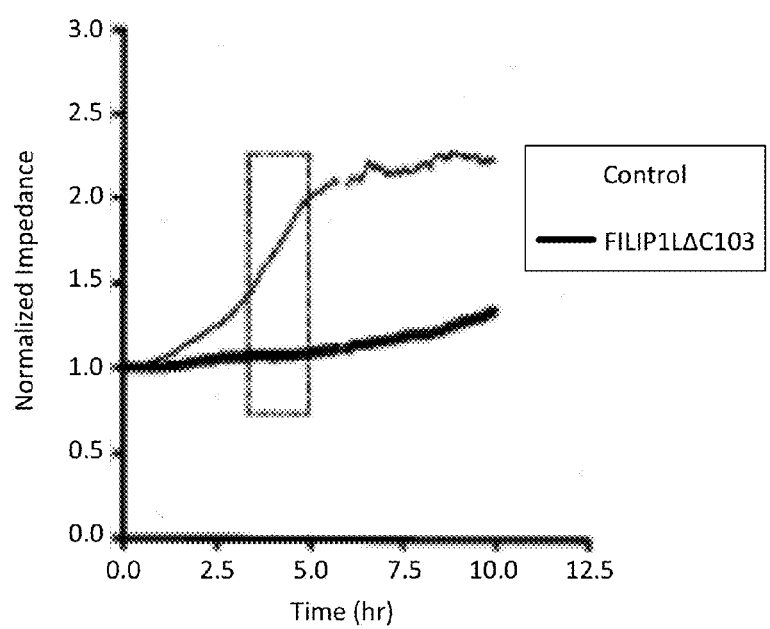
FIG. 3 shows that overexpression of FILIP1LΔC103 in HUVECs as well as DU145 prostate cancer cells leads to inhibition of cell migration. A, FILIP1LΔC103-transfected HUVECs showed a significantly slower migration rate than control vector-transfected HUVECs as measured by Electric Cell-Substrate Impedance Sensing System in real time (P<0.0001). The square box indicates the linear range in the curve that was used for analysis. The result is representative of three independent experiments.
Figure 9:
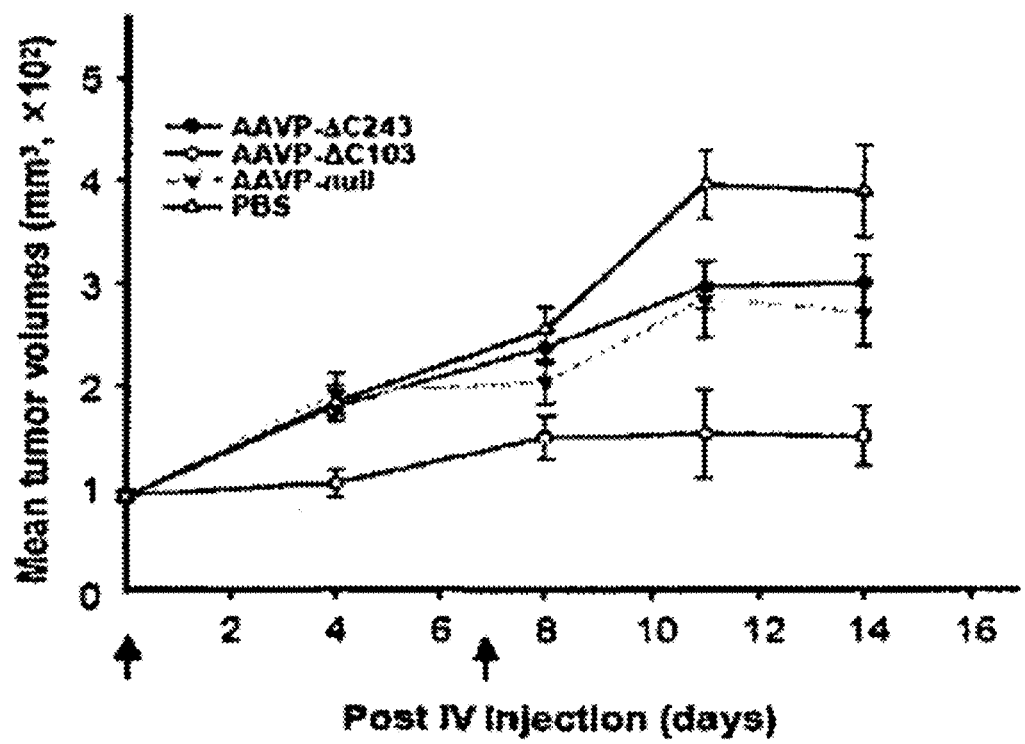
FIG. 9 shows that targeted expression of FILIP1LΔC103 in tumor vasculature results in inhibition of tumor growth in vivo. Tumors from AAVP-ΔC103-treated mice (empty circles) were significantly smaller than those from PBS-treated mice (empty triangles) in M21 xenograft model at day 14 (P<0.01). Tumors from AAVP-ΔC103-treated mice were also significantly smaller than those from AAVP-null-treated mice (filled triangles; P<0.05) and AAVP-ΔC243-treated mice (filled circles; P<0.05) by day 14. AAVP was injected intravenously at day 0 and day 7 (indicated by arrow). Error bars indicate SEM (n=11). The result is representative of two independent experiments.

Alternatively or in addition the DOC1 polypeptide can have the anti-migration activity of native DOC1 (see, e.g., FIG. 3 and FIG. 9).

A DOC1 polypeptide of the invention that retains at least 50% of the level of at least one function of the native DOC1 is considered to be functional. The DOC1 polypeptide can exhibit a level of activity that is 60%, 70%, 80%, 90%, 100% or greater than the level of the same activity of the full-length DOC1.

For example, disclosed is a purified DOC1 polypeptide, which is a fragment of SEQ ID NO: 1 comprising amino acids selected from the group consisting of amino acids amino acids 1-790 of SEQ ID NO: 1, amino acids 1-650 of SEQ ID NO: 1, amino acids 1-512 of SEQ ID NO: 1, amino acids 65-893 of SEQ ID NO: 1, amino acids 127-512 of SEQ ID NO:1, amino acids 127-893 of SEQ ID NO: 1, and amino acids 127-650 of SEQ ID NO: 1, and amino acids 127-790 of SEQ ID NO:1. More specifically, the DOC1 polypeptide having anti-proliferative activity can be selected from the group consisting of amino acids 1-790 of SEQ ID NO:1, amino acids 1-650 of SEQ ID NO:1, amino acids 1-512 of SEQ ID NO:1, and amino acids 127-893 of SEQ ID NO:1.

Also disclosed is a purified DOC1 polypeptide, which is a fragment of SEQ ID NO: 2 comprising amino acids selected from the group consisting of amino acids amino acids 1-746 of SEQ ID NO: 2, amino acids 1-752 of SEQ ID NO: 2, amino acids 1-650 of SEQ ID NO: 2, amino acids 1-512 of SEQ ID NO:2, amino acids 65-752 of SEQ ID NO:2, amino acids 127-512 of SEQ ID NO:2, amino acids 127-752 of SEQ ID NO:2, and amino acids 127-650 of SEQ ID NO:2, and amino acids 127-752 of SEQ ID NO:2. More specifically, the DOC 1 polypeptide having anti-proliferative activity can be selected from the group consisting of amino acids 1-746 of SEQ ID NO: 2, amino acids 1-752 of SEQ ID NO:2, amino acids 1-650 of SEQ ID NO:2, amino acids 1-512 of SEQ ID NO:2, and amino acids 127-752 of SEQ ID NO:2. Also disclosed is a purified DOC1 polypeptide, which is a fragment of SEQ ID NO: 3 comprising amino acids selected from the group consisting of amino acids amino acids 241-1128 of SEQ ID NO:3.

Also disclosed is a purified DOC1 polypeptide, which is a fragment of SEQ ID NO: 4 comprising amino acids selected from the group consisting of amino acids amino acids 241-1133 of SEQ ID NO:4.

A coiled-coil region (residues 3-542 of SEQ ID NO:1), two leucine zipper motifs (residues 83-111 and 218-253 of SEQ ID NO:1) and a prefoldin domain (residues 465-535 of SEQ ID NO:1) could be recognized in N-terminal half of DOC1 protein. In addition, NCBI conserved domain search reveals that DOC1 has a SbcC (COG0419; ATPase involved in DNA repair; residues 19-576) conserved domain in its N-terminal half and a Herpes_BLLF1 (pfam05109; Herpes virus major outer envelope glycoprotein; residues 640-829) conserved domain in its C-terminal half. A DOC1 polypeptide that retains the coiled-coil region (3-542 of SEQ ID NO:1) is expected to retain function.

2. Functional DOC1 Variants

Provided is a purified polypeptide comprising an amino acid sequence that is a functional variant of DOC1 or a functional variant of a fragment of DOC1. A functional variant of DOC1 or a functional variant of a DOC1 polypeptide possess at least one function of full-length DOC1 (e.g., SEQ ID NO:1, SEQ ID NO:2, SEQ ID NO:3 or SEQ ID NO:4). Examples of functions of DOC1 or DOC1 polypeptide are recited herein. In general, variants of the DOC1 proteins disclosed herein typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent similarity to the stated sequence or the native sequence. For example, the variant polypeptide can be at least about 95% identical to the amino acid sequence of SEQ ID NO:1 or functional fragment of SEQ ID NO:1 as described herein. For example, the variant polypeptide can be at least about 96% identical to the amino acid sequence of SEQ ID NO:1 or functional fragment of SEQ ID NO:1 as described herein. For example, the variant polypeptide can be at least about 97% identical to the amino acid sequence of SEQ ID NO:1 or functional fragment of SEQ ID NO:1 as described herein. For example, the variant polypeptide can be at least about 98% identical to the amino acid sequence of SEQ ID NO:1 or functional fragment of SEQ ID NO:1 as described herein. For example, the variant polypeptide can be at least about 99% identical to the amino acid sequence of SEQ ID NO:1 or functional fragment of SEQ ID NO:1 as described herein.

In a further example, the variant polypeptide can be at least about 95% identical to the amino acid sequence of SEQ ID NO:2 or functional fragment of SEQ ID NO:2 as described herein. For example, the variant polypeptide can be at least about 96% identical to the amino acid sequence of SEQ ID NO:2 or functional fragment of SEQ ID NO:2 as described herein. For example, the variant polypeptide can be at least about 97% identical to the amino acid sequence of SEQ ID NO:2 or functional fragment of SEQ ID NO:2 as described herein. For example, the variant polypeptide can be at least about 98% identical to the amino acid sequence of SEQ ID NO:2 or functional fragment of SEQ ID NO:2 as described herein. For example, the variant polypeptide can be at least about 99% identical to the amino acid sequence of SEQ ID NO:2 or functional fragment of SEQ ID NO:2 as described herein.

In a further example, the variant polypeptide can be at least about 95% identical to the amino acid sequence of SEQ ID NO:3 or functional fragment of SEQ ID NO:3 as described herein. For example, the variant polypeptide can be at least about 96% identical to the amino acid sequence of SEQ ID NO:3 or functional fragment of SEQ ID NO:3 as described herein. For example, the variant polypeptide can be at least about 97% identical to the amino acid sequence of SEQ ID NO:3 or functional fragment of SEQ ID NO:3 as described herein. For example, the variant polypeptide can be at least about 98% identical to the amino acid sequence of SEQ ID NO:3 or functional fragment of SEQ ID NO:3 as described herein. For example, the variant polypeptide can be at least about 99% identical to the amino acid sequence of SEQ ID NO:3 or functional fragment of SEQ ID NO:3 as described herein.

In a further example, the variant polypeptide can be at least about 95% identical to the amino acid sequence of SEQ ID NO:4 or functional fragment of SEQ ID NO:4 as described herein. For example, the variant polypeptide can be at least about 96% identical to the amino acid sequence of SEQ ID NO:4 or functional fragment of SEQ ID NO:4 as described herein. For example, the variant polypeptide can be at least about 97% identical to the amino acid sequence of SEQ ID NO:4 or functional fragment of SEQ ID NO:4 as described herein. For example, the variant polypeptide can be at least about 98% identical to the amino acid sequence of SEQ ID NO:4 or functional fragment of SEQ ID NO:4 as described herein. For example, the variant polypeptide can be at least about 99% identical to the amino acid sequence of SEQ ID NO:4 or functional fragment of SEQ ID NO:4 as described herein.

Those of skill in the art readily understand how to determine the sequence similarity of two proteins or nucleic acids. For example, the homology can be calculated after aligning the two sequences so that the homology is at its highest level. Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

Provided is a purified polypeptide comprising a fragment of SEQ ID NO:1, wherein the polypeptide has the formula $R_1$-fragment of SEQ ID NO:1-$R_2$, wherein $R_1$ or $R_2$ comprise, H, acyl, or an amino acid sequence that does not flank the fragment of SEQ ID NO:1 in any naturally occurring DOC1 polypeptide. For example, the following list is exemplary of the DOC1 polypeptides of the invention:

$R_1$-amino acids 1-790 of SEQ ID NO:1-$R_2$;
$R_1$-amino acids 1-650 of SEQ ID NO:1-$R_2$;
$R_1$-amino acids 1-512 of SEQ ID NO:1-$R_2$;
$R_1$-amino acids 127-512 of SEQ ID NO:1-$R_2$;
$R_1$-amino acids 127-893 of SEQ ID NO:1-$R_2$;
$R_1$-amino acids 127-650 of SEQ ID NO:1-$R_2$; and
$R_1$-amino acids 127-790 of SEQ ID NO:1-$R_2$.

3. Fusion Protein

For example, the polypeptide having the general formula $R_1$-fragment of SEQ ID NO:1-$R_2$ can be a fusion protein. Fusion proteins can include targeting sequences. The targeting molecule can be an RGD, NGR, GFP or any targeting sequence. Any molecule that can target a specific tissue can be used as the targeting molecule of the present fusion protein. For example, the targeting molecule can be a molecule (e.g., an antibody or aptamer) that interacts with human epithelial cell mucin (Muc-1; a 20 amino acid core repeat for Muc-1 glycoprotein, present on breast cancer cells and pancreatic cancer cells), the Ha-ras oncogene product, p53, carcinoembryonic antigen (CEA), the raf oncogene product, gp100/pmel17, GD2, GD3, GM2, TF, sTn, MAGE-1, MAGE-3, BAGE, GAGE, tyrosinase, gp75, Melan-A/Mart-1, gp100, HER2/neu, EBV-LMP 1 & 2, HPV-F4, 6, 7, prostate-specific antigen (PSA), HPV-16, MUM, alpha-fetoprotein (AFP), C017-1A, GA733, gp72, p53, the ras oncogene product, HPV E7, Wilm's tumor antigen-1, telomerase, melanoma gangliosides, or a simple transmembrane sequence.

Selective delivery of therapeutic agents to cancer cells in a living body is another area of research where targeting of cancer specific biomarkers is intensively studied. (E. Mastrobattista, G. A. Koning, and G. Storm, "Immonoliposomes for the Targeted Delivery of Antitumor Drugs," Adv Drug Delivery Reviews 1999, 40: 103-27; J. Sudimack and R. J. Lee, "Targeted Drug Delivery Via Folate Receptor," Adv Drug Delivery Reviews 2000, 41: 147-62; S. P. Vyas and V. Sihorkar, "Endogenous Carriers and Ligands in Non-Immunogenic Site-Specific Drug Delivery," Adv Drug Delivery Reviews 2000, 43: 101-64.). Immunoliposome-mediated targeting using monoclonal antibodies to folate receptor, (E. Mastrobattista, G. A. Koning, and G. Storm, "Immonoliposomes for the Targeted Delivery of Antitumor Drugs," Adv Drug Delivery Reviews 1999, 40: 103-27; J. Sudimack and R. J. Lee, "Targeted Drug Delivery Via Folate Receptor," Adv Drug Delivery Reviews 2000, 41: 147-62) CA-125, (E. Mastrobattista, G. A. Koning, and G. Storm, "Immonoliposomes for the Targeted Delivery of Antitumor Drugs," Adv Drug Delivery Reviews 1999, 40: 103-27) and HER2/neu antigen (D. B. Kirpotin, J. W. Park, K. Hong, S. Zalipsky, W. L. Li, P. Carter, C. C. Benz, and D. Papahadjopoulos, "Sterically Stabilized anti-HER2 immunoliposomes: design and targeting to human breast cancer cells in vitro," Biochemistry 1997, 36: 66-75) have been described.

The targeting molecule of the instant invention is an optional feature that presents an extra measure of selectivity. The targeting molecule directs the fusion protein to the target cell, where the DOC1 polypeptide can cause apoptosis or inhibit proliferation or both. The targeting molecule may be added to the N- or C-terminus, or both.

In some embodiments, the targeting molecule is an antibody. For example, the antibody can be an anti-fibronectin ED-B antibody, thereby directing the DOC1 fragment to the extracellular matrix associated with neo-vessel formation.

Targeting molecules that target the neo-vasculature can also be linked to the DOC1 fragment. Molecules that target the neo-vasculature can easily be identified by screening phage display libraries. Any such peptide would be a suitable targeting molecule of the present invention.

Targeting molecules which bind specifically to integrins are one class of signal sequences that can be found on cells of the vasculature. These peptides bear the signal sequence based on Arg-Gly-Asp (RGD). Accordingly, sequences that bind certain integrins can serve as useful targeting molecules to endothelial cells and other cells of the neo-vasculature. For example, the targeting molecule can be an RGD targeting sequence.

Non-structural spacers may be a feature of the targeting molecule. Such spacers typically comprise glycine and/or proline residues. Lengths of these spacers can range from about one to about 5 amino acids. In addition, it is often preferable to physically constrain the targeting molecule by cyclization, which usually results in increased binding. This is usually accomplished by a pair of cysteine residues, flanking the RGD core at a distance of about 4 (having only RGD in between) to 10 amino acids from one another. For example, the pair of cysteine residues, flanking the RGD core can be at a distance of 7 amino acids from one another.

Thus, a typical targeting molecule would have the following structure: -XRGDYX- wherein X is zero to five amino acids and Y is a one or two amino acids, selected from cysteine, serine, threonine and methionine. In a particularly useful embodiment, X is comprised of glycine residues, but optionally contains at least one, and typically one or two, free thiol- or amine-containing amino acids and/or a single hydrophobic amino acid. Thiol-containing residues include methionine and cysteine; amine-containing residues include lysine and (at least one additional) arginine; and hydrophobic residues include leucine, isoleucine, alanine and phenylalanine.

Targeting molecules which bind specifically to integrins are one class of signal sequences that can be found on cells of the vasculature. These peptides bear the signal sequence based on Asn-Gly-Arg (NGR). Accordingly, sequences that bind certain integrins can serve as useful targeting molecules to endothelial cells and other cells of the neo-vasculature. For example, the targeting molecule can be an NGR targeting sequence.

Non-structural spacers may be a feature of the targeting molecule. Such spacers typically comprise glycine and/or proline residues. Lengths of these spacers can range from about one to about 5 amino acids. In addition, it is often preferable to physically constrain the targeting molecule by cyclization, which usually results in increased binding. This is usually accomplished by a pair of cysteine residues, flanking the NGR core at a distance of about 4 (having only NGR in between) to 10 amino acids from one another. For example, the pair of cysteine residues, flanking the NGR core can be at a distance of 7 amino acids from one another.

Thus, a typical targeting molecule would have the following structure: -XNGRYX- wherein X is zero to five amino acids and Y is a one or two amino acids, selected from cysteine, serine, threonine and methionine. In a particularly useful embodiment, X is comprised of glycine residues, but optionally contains at least one, and typically one or two, free thiol- or amine-containing amino acids and/or a single hydrophobic amino acid. Thiol-containing residues include methionine and cysteine; amine-containing residues include lysine and (at least one additional) arginine; and hydrophobic residues include leucine, isoleucine, alanine and phenylalanine.

The targeting molecule can be an aptamer or an antibody specific for the target. Traditionally, the identification of biomarkers and development of antibodies for their specific targeting has been a difficult and time-consuming process that does not always provide the best result for a particular application. For example, although many cancer related biomarkers have been identified, only few of them have shown promising results for cancer screening and prognosis, and it has been recognized that it may be true that only combinations of these biomarkers can provide the best discrimination between cancerous and normal tissue.

Numerous reviews have been written about the practice and products of in vitro selection of aptamers. (Conrad, R. C., L. Giver, et al. (1996). "In vitro selection of nucleic acid aptamers that bind proteins." Methods Enzymol 267: 336-67; Osborne, S. E., I. Matsumura, et al. (1997). "Aptamers as therapeutic and diagnostic reagents: problems and prospects." Curr Opin Chem Biol 1(1): 5-9; Famulok, M. and G. Mayer (1999). "Aptamers as tools in molecular biology and immunology." Curr Top Microbiol Immunol 243: 123-36; Hesselberth, J., M. P. Robertson, et al. (2000). "In vitro selection of nucleic acids for diagnostic applications [In Process Citation]." J Biotechnol 74(1): 15-25.). The methods of the present invention may utilize aptamers with unique or improved binding characteristics to a target that is unique to or over represented (as compared to a normal or non-target cell) in, around or on a cell of interest. An "aptamer" as used herein refers to a nucleic acid that binds a target molecule through interactions or conformations other than those of nucleic acid annealing/hybridization described herein. Methods for making and modifying aptamers, and assaying the binding of an aptamer to a target molecule may be assayed or screened for by any mechanism known to those of skill in the art (see for example, U.S. Pat. Nos. 6,111,095, 5,861,501, 5,840,867, 5,792,613, 5,780,610, 5,780,449, 5,756,291 5,631,146 and 5,582,981; as well as PCT Publication Nos. WO92/14843, WO91/19813, and WO92/05285, each of which is incorporated herein by reference).

Aptamers are single- or double-stranded DNA or single-stranded RNA molecules that recognize and bind to a desired target molecule by virtue of their shapes. See, e.g., PCT Publication Nos. WO92/14843, WO91/19813, and WO92/05285. The SELEX procedure, described in U.S. Pat. No. 5,270,163 to Gold et al., Tuerk et al. (1990) Science 249:505-510, Szostak et al. (1990) Nature 346:818-822 and Joyce (1989) Gene 82:83-87, can be used to select for RNA or DNA aptamers that are target-specific. In the SELEX procedure, an oligonucleotide is constructed wherein an n-mer, preferably a random sequence tract of nucleotides thereby forming a "randomer pool" of oligonucleotides, is flanked by two polymerase chain reaction (PCR) primers. The construct is then contacted with a target molecule under conditions which favor binding of the oligonucleotides to the target molecule. Those oligonucleotides which bind the target molecule are: (a) separated from those oligonucleotides which do not bind the target molecule using conventional methods such as filtration, centrifugation, chromatography, or the like; (b) dissociated from the target molecule; and (c) amplified using conventional PCR technology to form a ligand-enriched pool of oligonucleotides. Further rounds of binding, separation, dissociation and amplification are performed until an aptamer with the desired binding affinity, specificity or both is achieved. The final aptamer sequence identified can then be prepared chemically or by in vitro transcription.

The length of a random sequence tract can range from 20 to over 150 residues, and can be even longer if multiple, random oligonucleotides are combined into a single pool by ligation or other methods. (Bartel, D. P. and J. W. Szostak (1993). "Isolation of new ribozymes from a large pool of random sequences [see comment]." Science 261(5127): 1411-8.). The number of individuals in a random sequence population is typically at least 10.sup.13 and can easily be over 10.sup.15. For most pools, this means that upwards of all possible 25-mers are present, and a proportionately smaller number of motifs longer than 25. Because of the redundancy of biological sequences, the sequence diversity of most random sequence pools likely rivals the sequence diversity of the Earth's biosphere.

Aptamers have been selected against a surprising range of targets, ranging from ions to small organics to peptides to proteins to supramolecular structures such as viruses and tissues. (Famulok, M. and G. Mayer (1999). "Aptamers as tools in molecular biology and immunology." Curr Top Microbiol Immunol 243: 123-36; Xu, W. and A. D. Ellington (1996). "Anti-peptide aptamers recognize amino acid sequence and bind a protein epitope." Proc Natl Acad Sci USA 93(15): 7475-80; Weiss, S., D. Proske, et al. (1997). "RNA aptamers specifically interact with the prion protein PrP." J Virol 71(11): 8790-7; Convery, M. A., S. Rowsell, et al. (1998). "Crystal structure of an RNA aptamer-protein complex at 2.8 A resolution." Nat Struct Biol 5(2): 133-9; Homann, M. and H. U. Goringer (1999). "Combinatorial selection of high affinity RNA ligands to live African trypanosomes." Nucleic Acids Res 27(9): 2006-14.). In particular, aptamers have been selected against a wide variety of proteins, including many nucleic acid binding proteins, such as T4 DNA polymerase (Tuerk, C. and L. Gold (1990). "Systematic evolution of ligands by exponential enrichment: RNA ligands to bacteriophage T4 DNA polymerase." Science 249 (4968): 505-10.) and HIV-1 Rev, (Giver, L., D. Bartel, et al. (1993). "Selective optimization of the Rev-binding element of HIV-1." Nucleic Acids Res 21(23): 5509-16.) and multiple non-nucleic acid binding proteins. In general, anti-protein aptamers seem to recognize basic patches on protein surfaces. For example, the arginine-rich motifs (ARMs) of many viral proteins are recognized by aptamers (reviewed in Ellington, A. D., F. Leclerc, et al. (1996). "An RNA groove [news]." Nat Struct Biol 3(12): 981-4.), the phosphate-binding pockets of both kinases (Conrad, R., L. M. Keranen, et al. (1994). "Isozyme-specific inhibition of protein kinase C by RNA aptamers." J Biol Chem 269(51): 32051-4.) and phosphatases, (Bell, S. D., J. M. Denu, et al. (1998). "RNA molecules that bind to and inhibit the active site of a tyrosine phosphatase." J Biol Chem 273(23): 14309-14.) and the heparin-binding sites on many surface proteins and cytokines, such as basic fibroblast growth factor (Jellinek, D., C. K. Lynott, et al. (1993). "High-affinity RNA ligands to basic fibroblast growth factor inhibit receptor binding." Proc Natl Acad Sci USA 90(23): 11227-31; Jellinek, D., L. S. Green, et al. (1995). "Potent 2'-amino-2'-deoxypyrimidine RNA inhibitors of basic fibroblast growth factor." Biochemistry 34(36): 11363-72.) and vascular endothelial growth factor. (Jellinek, D., L. S. Green, et al. (1994) "Inhibition of receptor binding by high-affinity RNA ligands to vascular endothelial growth factor." Biochemistry 33(34): 10450-6; Green, L. S., D. Jellinek, et al. (1995). "Nuclease-resistant nucleic acid ligands to vascular permeability factor/vascular endothelial growth factor." Chem Biol 2(10): 683-95.).

Aptamers also seem to have an affinity for pockets or cusps on protein surfaces, such as the combining sites of antibodies (Tsai, D. E., D. J. Kenan, et al. (1992). "In vitro selection of an RNA epitope immunologically cross-reactive with a peptide." Proc Natl Acad Sci USA 89(19): 8864-8) or the active sites of enzymes. (Tuerk, C., S. MacDougal, et al. (1992). "RNA pseudoknots that inhibit human immunodeficiency virus type 1 reverse transcriptase." Proc Natl Acad Sci USA 89(15): 6988-92.). Almost all proteins have either surface pockets or basic patches (indeed, even proteins with negative pI's, such as T4 DNA polymerase, typically contain sites that can elicit aptamers). Most aptamer: target complexes have dissociation constants in the nanomolar range. Moreover, aptamers recognize their targets with high specificity, and can typically discriminate between protein targets that are highly homologous or differ by only a few amino acids. (Conrad, R., L. M. Keranen, et al. (1994). "Isozyme-specific inhibition of protein kinase C by RNA aptamers." J Biol Chem 269(51): 32051-4; Eaton, B. E., L. Gold, et al. (1995). "Let's get specific: the relationship between specificity and affinity." Chem Biol 2(10): 633-8; Hirao, I., M. Spingola, et al. (1998). "The limits of specificity: an experimental analysis with RNA aptamers to MS2 coat protein variants." Mol Divers 4(2): 75-89.).

Thus, an example of a fusion protein comprises amino acids 127-512 of SEQ ID NO:1, flanked N-terminally or C-terminally with RGD, e.g., RGD-amino acids 127-52 of SEQ ID NO:1 or
amino acids 127-52 of SEQ ID NO:1-RGD.
Further examples of the fusion protein include:
[targeting molecule]-amino acids 1-790 of SEQ ID NO: 1,
amino acids 1-790 of SEQ ID NO: 1-[targeting molecule],
[targeting molecule]-amino acids 1-650 of SEQ ID NO: 1,
amino acids 1-650 of SEQ ID NO: 1-[targeting molecule],
[targeting molecule]-amino acids 1-512 of SEQ ID NO: 1,
amino acids 1-512 of SEQ ID NO: 1-[targeting molecule],
[targeting molecule]-amino acids 65-893 of SEQ ID NO: 1,
amino acids 65-893 of SEQ ID NO: 1-[targeting molecule],
[targeting molecule]-amino acids 127-893 of SEQ ID NO: 1, amino acids 127-790 of SEQ ID NO: 1-[targeting molecule],

[targeting molecule]-amino acids 127-790 of SEQ ID NO: 1, amino acids 127-893 of SEQ ID NO: 1-[targeting molecule]

[targeting molecule]-amino acids 127-650 of SEQ ID NO: 1, and amino acids 127-650 of SEQ ID NO: 1-[targeting molecule], wherein the targeting molecule is as described herein. It will be understood that linkers (e.g., amino acids) can be used to link the DOC1 peptide region of the fusion protein to the non-DOC1 region of the fusion protein. A nucleic acid encoding each of the above polypeptides is also provided.

4. Sequence Similarities

It is understood that as discussed herein the use of the terms homology and identity mean the same thing as similarity. Thus, for example, if the word homology is used to compare two non-natural sequences it is understood that this is not necessarily indicating an evolutionary relationship between these two sequences, but rather is looking at the similarity or relatedness between their nucleic acid (or amino acid) sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of similarity to specific known sequences. The similarity of particular sequences disclosed herein is discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent similarity to the stated sequence or the native sequence. Those of skill in the art readily understand how to determine the similarity of two proteins or nucleic acids, such as genes. For example, the similarity can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Similarity can also be determined based on a nucleotide by nucleotide (amino acid by amino acid) comparison. This comparison can include a comparison of all of the nucleotides/amino acids in one sequence against all of the nucleotides/amino acids in the other sequence (overall homology); thus, the similarity will be reduced by differences in the length of the sequences being compared. For example, in such a comparison, a 50 nt nucleic acid and a 100 nt nucleic acid have a region of overlap defined by the shorter sequence; if nt in that overlap are identical, the sequences will have 50% similarity. In contrast, the comparison can be based on only the overlapping region. For example, in such a comparison, a 50 nt nucleic acid and a 100 nt nucleic acid that have an identical overlapping region of 50 nt, will have 100% similarity. As a further example of comparison in the region of overlap, a 50 nt nucleic acid and a 100 nt nucleic acid that have 25 nucleotides that differ in the overlapping region, will have 50% similarity.

5. Nucleic Acids

There are a variety of molecules disclosed herein that are nucleic acid based, including for example the nucleic acids that encode, for example DOC1, or fragments thereof, as well as various functional nucleic acids.

Provided are nucleic acids encoding the full-length DOC1 protein of SEQ ID NO:1. The nucleic acids encoding DOC1 have sequences defined by the amino acid sequence of DOC1 in accordance with the degeneracy of the genetic code. Also, provided are nucleic acids encoding functional fragments of DOC1, i.e., encoding the DOC1 polypeptide of the invention. The length of these nucleic acids is commensurate with the length of the polypeptide they encode. For example the nucleic acids encode polypeptides having a length from 10 to 1133 amino acids. Thus, the nucleic acids encoding these polypeptides range from 30 to 3399 nucleotides in length, including all numbers of nucleotides in between based on the number of codons required.

Provided are nucleic acids encoding a DOC1 fragment-containing fusion protein disclosed herein. The length of these nucleic acids are commensurate with the length of the fusion polypeptide they encode. The nucleic acid encodes, for example, both the DOC1 fragment containing region and the coding region for a targeting moiety.

The disclosed nucleic acids can be made up of for example, nucleotides, nucleotide analogs, or nucleotide substitutes. Non-limiting examples of these and other molecules are discussed herein. It is understood that for example, when a vector is expressed in a cell, the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

i. Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

ii. Sequences

There are a variety of sequences related to the protein molecules for DOC1, for example SEQ ID NO:1, SEQ ID NO:2, SEQ ID NO:3 or SEQ ID NO:4, or any of the nucleic acids disclosed herein for producing DOC1, all of which are encoded by nucleic acids or are nucleic acids. The sequences for the human analogs of these genes, as well as other analogs, and alleles of these genes, and splice variants and other types of variants, are available in a variety of protein and gene databases, including GenBank. Those sequences available at the time of filing this application at GenBank are herein incorporated by reference in their entireties as well as for individual subsequences contained therein. GenBank can be accessed at http://www.ncbi.nih.gov/entrez/query.fcgi.

Those of skill in the art understand how to resolve sequence discrepancies and differences and to adjust the compositions and methods relating to a particular sequence to other related sequences. Primers and/or probes can be designed for any given sequence given the information disclosed herein and known in the art.

iii. Primers and Probes

Disclosed are compositions including primers and probes, which are capable of interacting with the disclosed nucleic acids, such as the DOC1 nucleic acids as disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the disclosed nucleic acids or region of the nucleic acids or they hybridize with the complement of the nucleic acids or complement of a region of the nucleic acids.

The size of the primers or probes for interaction with the nucleic acids in certain embodiments can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750 or 3000 nucleotides long.

In other embodiments a primer or probe can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750 or 3000 nucleotides long.

The primers for the DOC1 gene typically will be used to produce an amplified DNA product that contains a region of the DOC1 gene or the complete gene. In general, typically the size of the product will be such that the size can be accurately determined to within 3, or 2 or 1 nucleotides.

In certain embodiments this product is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000 or 3405 nucleotides long.

In other embodiments the product is less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000 or 3405 nucleotides long.

iv. Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, RNAi, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$. A representative sample of methods and techniques which aid in the design and use of antisense molecules can be found in U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $K_d$'s from the target molecule of less than 10-12 M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule (U.S. Pat. No. 5,543,293). It is preferred that the aptamer have a $K_d$ with the target molecule at least 10, 100, 1000, 10,000, or 100,000 fold lower than the $K_d$ with a background binding molecule. It is preferred when doing the comparison for a polypeptide for example, that the background molecule be a different polypeptide. Representative examples of how to make and use aptamers to bind a variety of different target molecules can be found in U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203; International Patent Application Nos. WO 9858058 by Ludwig and Sproat, WO 9858057 by Ludwig and Sproat, and WO 9718312 by Ludwig and Sproat) hairpin ribozymes (for example, U.S. Pat. Nos. 5,631,115, 5,646,031, 5,683,902, 5,712,384, 5,856,188, 5,866,701, 5,869,339, and 6,022,962), and tetrahymena ribozymes (for example, U.S. Pat. Nos. 5,595,873 and 5,652,107). There are also a number of ribozymes that are not found in natural systems, but which have been engineered to catalyze specific reactions de novo (for example, U.S. Pat. Nos. 5,580,967, 5,688,670, 5,807, 718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in U.S. Pat. Nos. 5,646,042, 5,693,535, 5,731,295, 5,811,300, 5,837, 855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $K_d$ less than 10-6, 10-8, 10-10, or 10-12. Representative examples of how to make and use triplex forming molecules to bind a variety of different target molecules can be found in U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, Science 238:407-409 (1990)).

Similarly, eukaryotic EGS/RNAse P-directed cleavage of RNA can be utilized to cleave desired targets within eukarotic cells. (Yuan et al., Proc. Natl. Acad. Sci. USA 89:8006-8010 (1992); WO 93/22434 by Yale; WO 95/24489 by Yale; Yuan and Altman, EMBO J 14:159-168 (1995), and Carrara et al., Proc. Natl. Acad. Sci. (USA) 92:2627-2631 (1995)). Representative examples of how to make and use EGS molecules to facilitate cleavage of a variety of different target molecules be found in U.S. Pat. Nos. 5,168,053, 5,624,824, 5,683,873, 5,728,521, 5,869,248, and 5,877,162.

Gene expression can also be effectively silenced in a highly specific manner through RNA interference (RNAi). This silencing was originally observed with the addition of double stranded RNA (dsRNA) (Fire, A., et al. (1998) Nature, 391: 806-11; Napoli, C., et al. (1990) Plant Cell 2:279-89; Hannon, G. J. (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200; Bernstein, E., et al. (2001) Nature, 409:363-6; Hammond, S. M., et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al. (2001) Nature, 411:494 498) (Ui-Tei, K., et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. Disclosed herein are any shRNA designed as described above based on the sequences for the herein disclosed inflammatory mediators.

Examples of siRNAs for DOC1 include pSiRNA-Neo-DOC1: 5'AGCGTAACCAAGGAGAGAGAT3' (accession number XM_002964, position 1172-1192; SEQ ID NO:5); and pSiRNA-Neo-Control: 5'ATTCATTCATTCATTCAC-CAT3' (accession number D00269, position 1192-1212; SEQ ID NO:6)

6. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

7. Cell Delivery Systems

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

For example, provided is a vector comprising a nucleic acid encoding the DOC1 polypeptide of SEQ ID NO:1 or a nucleic acid that encodes a functional fragment of DOC1 as described herein.

Based on the provision of such a vector, provided is a host cell containing a vector comprising a nucleic acid encoding the DOC1 polypeptide of SEQ ID NO:1 or a nucleic acid that encodes a functional fragment of DOC1 as described herein.

A vector comprising a nucleic acid encoding the fusion protein containing a functional DOC1 fragment is provided.

Based on the provision of such a vector, provided is a host cell containing a vector comprising a nucleic acid encoding the fusion protein containing a functional DOC1 fragment disclosed herein.

i. Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as DOC1 coding sequence and expression-related sequences into the cell without degradation and include a promoter yielding expression of the gene in the cells into which it is delivered. In some embodiments the vectors are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

a. Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

b. Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

c. Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorproated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

d. Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes.

Other useful systems include, for example, replicating and host-restricted non-replicating vaccinia virus vectors.

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

ii. Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed DOC1 or vectors encoding DOC1 for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Feigner et al. *Proc. Natl. Acad. Sci. USA* 84:7413-7417 (1987); U.S. Pat. No. 4,897, 355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue, the principles of which can be applied to targeting of other cells (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

8. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

i. Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

ii. Markers

The viral vectors can include nucleic acid sequence encoding a marker product. This marker product is used to determine if the gene has been delivered to the cell and once delivered is being expressed. Preferred marker genes are the E. Coli lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

9. Peptides i. Protein Variants

As discussed herein there are numerous variants of the DOC1 protein that are known and herein contemplated. In addition, to the known functional DOC1 variants there are derivatives of the DOC1 proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations | |
|---|---|---|
| Alanine | Ala | A |
| Allosoleucine | AIle | |
| Arginine | Arg | R |
| Asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| Proline | Pro | P |
| Pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 2

Amino Acid Substitutions
Original Residue Exemplary Conservative Substitutions,
others are known in the art.

| | |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO:1 sets forth a particular sequence of DOC1 and SEQ ID NO:2 sets forth a particular sequence of a variant DOC1 protein, SEQ ID NO:3 sets forth a particular sequence of another variant DOC1 protein, and SEQ ID NO:4 sets forth a particular sequence of another variant DOC1 protein. Specifically disclosed are variants of these and other proteins herein disclosed which have at least, 70% or 75% or 80% or 85% or 90% or 95% sequence similarity (also referred to as homology) to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO:1 is set forth in SEQ ID NO:7. Other nucleic acids that encode the same protein sequence set forth in SEQ ID NO:1 are known to the skilled person based on degeneracy of the genetic code.

In addition, for example, a disclosed conservative derivative of SEQ ID NO:1 is shown in SEQ ID NO: 8, where the isoleucine (I) at position 20 is changed to a valine (V). It is understood that for this mutation all of the nucleic acid sequences that encode this particular derivative of DOC1 are also disclosed. It is also understood that while no amino acid sequence indicates what particular DNA sequence encodes that protein within an organism, where particular variants of a disclosed protein are disclosed herein, the known nucleic acid sequence that encodes that protein is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $—CH_2NH—$, $—CH_2S—$, $—CH_2—CH_2—$, $—CH=CH—$ (cis and trans), $—COCH_2—$, $—CH(OH)CH_2—$, and $—CHH_2SO—$ (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) ($—CH_2NH—$, $CH_2CH_2—$); Spatola et al. Life Sci 38:1243-1249 (1986) ($—CHH_2—S$); Hann J. Chem. Soc Perkin Trans. 1307-314 (1982) ($—CH—CH—$, cis and trans); Almquist et al. J. Med. Chem. 23:1392-1398 (1980) ($—COCH_2—$); Jennings-White et al. Tetrahedron Lett 23:2533 (1982) (—COCH$_2$—); Szelke et al. European Appln, EP 45665 CA (1982): 97:39405 (1982) (—CH(OH)CH$_2$—); Holladay et al. Tetrahedron. Lett 24:4401-4404 (1983) (—C(OH)CH$_2$—); and Hruby Life Sci 31:189-199 (1982) (—CH$_2$—S—); each of which is incorporated herein by reference. A particularly preferred non-peptide linkage is —CH$_2$NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

10. Antibodies

Provided is an antibody that specifically binds a full-length wild-type DOC1, or a full-length variant of DOC1 as defined herein. "Specifically binds" is used herein to mean an antibody that binds the amino acid sequence of the peptide specified, and not any other peptide with a substantially different polypeptide sequence. Also provided is an antibody that specifically binds to a DOC1 polypeptide disclosed herein. Provided is an antibody that can specifically bind to a fragment of DOC1, wherein the fragment comprises a polypeptide selected from the group consisting of amino acids amino acids 1-790 of SEQ ID NO: 1, amino acids 1-650 of SEQ ID NO: 1, amino acids 1-512 of SEQ ID NO: 1, amino acids 65-893 of SEQ ID NO: 1, amino acids 127-893 of SEQ ID NO: 1, and amino acids 127-650 of SEQ ID NO: 1. Provided is an antibody that specifically binds the DOC1 polypeptide consisting of amino acids 1-790 or SEQ ID NO:1 and the DOC1 polypeptide consisting of amino acids 1-650 or SEQ ID NO:1. Provided is an antibody that binds to a fragment of DOC1, with the proviso that the antibody does specifically not bind to a fragment consisting of amino acids 3-32, 3-52, 43-52, or 510-893 of SEQ ID NO:1.

Provided is an antibody that has the binding characteristics of the antibody that binds the DOC1 polypeptide comprising amino acids 1-790 of SEQ ID NO:1, e.g., the antibody produced by the hybridoma deposited with the ATCC under deposit number SD-5990/5991. Further provided is an antibody that has the binding characteristics of the antibody that binds wild-type DOC1 (SEQ ID NO:1), e.g., the antibody antibody produced by the hybridoma deposited with the American Type Culture Collection (ATCC), P.O. Box 1549, Manassas, Va. 20108 under deposit number SD-5990/5991. Binding characteristics of an antibody include its binding specificity. The binding specificity can be specificity for the antigen or it can be specificity based on the epitope recognized by the antibody. Since both the former and the latter are inherent characteristics of an antibody, the disclosure of the present antibodies provides definition of both epitope and antigen specificity. Thus, provided are an antibody that has the binding specificity of the antibody produced by the hybridoma deposited with the ATCC under deposit number SD-5990/5991 and an antibody that has the binding specificity of the antibody produced by the hybridoma deposited with the ATCC under deposit number SD-5990/5991. Reference to the binding specificity of a deposited monoclonal antibody is the equivalent of reference to the specific epitope on DOC1 to which that antibody binds. The binding specificity of any individual monoclonal antibody is an inherent property of any other monoclonal antibody of the sub-genus defined by the disclosed, deposited antibody. Methods of identifying the binding specificity of a given antibody are well known in the art. Further methods of measuring avidity and other characteristics of antibody binding are well known.

i. Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with DOC1 or DOC1 fragment. Antibodies that bind the disclosed regions of DOC1 are disclosed. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

ii. Human Antibodies

The disclosed human antibodies can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86-95, 1991). Human antibodies (and fragments thereof) can also be produced using phage display libraries (Hoogenboom et al., *J. Mol. Biol.*, 227:381, 1991; Marks et al., *J. Mol. Biol.*, 222:581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255 (1993); Jakobovits et al., *Nature*, 362:255-258 (1993); Bruggermann et al., *Year in Immunol.*, 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

iii. Humanized Antibodies

Antibody humanization techniques generally involve the use of recombinant DNA technology to manipulate the DNA sequence encoding one or more polypeptide chains of an antibody molecule. Accordingly, a humanized form of the mouse or other non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature*, 321:522-525 (1986), Reichmann et al., *Nature*, 332:323-327 (1988), and Presta, *Curr. Opin. Struct. Biol.*, 2:593-596 (1992)).

Methods for humanizing non-human antibodies are well known in the art. For example, humanized antibodies can be generated according to the methods of Winter and co-workers (Jones et al., *Nature*, 321:522-525 (1986), Riechmann et al., *Nature*, 332:323-327 (1988), Verhoeyen et al., *Science*, 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

iv. Administration of Antibodies

Administration of the antibodies can be done as disclosed herein. Nucleic acid approaches for antibody delivery also exist. The anti-DOC1 antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

11. Effectors

The herein provided compositions can further comprise an effector molecule. By "effector molecule" is meant a substance that acts upon the target cell(s) or tissue to bring about a desired effect. The effect can, for example, be the labeling, activating, repressing, or killing of the target cell(s) or tissue. Thus, the effector molecule can, for example, be a small molecule, pharmaceutical drug, toxin, fatty acid, detectable marker, conjugating tag, nanoparticle, or enzyme. The effector can be a known anti-cancer therapeutic that can be administered with the disclosed full-length DOC1 polypeptide or DOC1 polypeptide comprising a DOC1 fragment.

Examples of small molecules and pharmaceutical drugs that can be conjugated to a targeting peptide are known in the art. The effector can be a cytotoxic small molecule or drug that kills the target cell. The small molecule or drug can be designed to act on any critical cellular function or pathway. For example, the small molecule or drug can inhibit the cell cycle, activate protein degradation, induce apoptosis, modulate kinase activity, or modify cytoskeletal proteins. Any known or newly discovered cytotoxic small molecule or drugs is contemplated for use with the targeting peptides.

The effector can be a toxin that kills the targeted cell. Non-limiting examples of toxins include abrin, modeccin, ricin and diphtheria toxin. Other known or newly discovered toxins are contemplated for use with the provided compositions.

Fatty acids (i.e., lipids) that can be conjugated to the provided compositions include those that allow the efficient incorporation of the peptide into liposomes. Generally, the fatty acid is a polar lipid. Thus, the fatty acid can be a phospholipid The provided compositions can comprise either natural or synthetic phospholipid. The phospholipids can be selected from phospholipids containing saturated or unsaturated mono or disubstituted fatty acids and combinations thereof. These phospholipids can be dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Albaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, (16:0)-oleoyl (18:1)-PC, and myristoyl (14:0)-oleoyl (18:1)-PC as constituents. Thus, as an example, the provided compositions can comprise palmitoyl 16:0.

Detectable markers include any substance that can be used to label or stain a target tissue or cell(s). Non-limiting examples of detectable markers include radioactive isotopes, enzymes, fluorochromes, and quantum dots (Qdot®). Other known or newly discovered detectable markers are contemplated for use with the provided compositions.

The effector molecule can be a nanoparticle, such as a heat generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Nanoshells can be formed with a core of a dielectric or inert material such as silicon, coated with a material such as a highly conductive metal which can be excited using radiation such as near infrared light (approximately 800 to 1300 nm). Upon excitation, the nanoshells emit heat. The resulting hyperthermia can kill the surrounding cell(s) or tissue. The combined diameter of the shell and core of the nanoshells ranges from the tens to the hundreds of nanometers. Near infrared light is advantageous for its ability to penetrate tissue. Other types of radiation can also be used, depending on the selection of the nanoparticle coating and targeted cells. Examples include x-rays, magnetic fields, electric fields, and ultrasound. The problems with the existing methods for hyperthermia, especially for use in cancer therapy, such as the use of heated probes, microwaves, ultrasound, lasers, perfusion, radiofrequency energy, and radiant heating is avoided since the levels of radiation used as described herein is insufficient to induce hyperthermia except at the surface of the nanoparticles, where the energy is more effectively concentrated by the metal surface on the dielectric. The particles can also be used to enhance imaging, especially using infrared diffuse photon imaging methods. Targeting molecules can be antibodies or fragments thereof, ligands for specific receptors, or other proteins specifically binding to the surface of the cells to be targeted.

The effector molecule can be covalently linked to the disclosed peptide. The effector molecule can be linked to the amino terminal end of the disclosed peptide. The effector molecule can be linked to the carboxy terminal end of the disclosed peptide. The effector molecule can be linked to an amino acid within the disclosed peptide. The herein provided compositions can further comprise a linker connecting the effector molecule and disclosed peptide. The disclosed peptide can also be conjugated to a coating molecule such as bovine serum albumin (BSA) (see Tkachenko et al., (2003) J Am Chem Soc, 125, 4700-4701) that can be used to coat the Nanoshells with the peptide.

Protein crosslinkers that can be used to crosslink the effector molecule to the disclosed peptide are known in the art and are defined based on utility and structure and include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxycarbonyloxy)ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio)propionamido]butane), BSSS (Bis(sulfosuccinimdyl)suberate), SMPB (Succinimdyl-4-(p-maleimidophenyl)butyrate), SULFO SMPB (Sulfosuccinimdyl-4-(p-maleimidophenyl)butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl)aminobenzoate), SULFO SIAB (N-Sulfosuccinimidyl(4-iodoacetyl)aminobenzoate), SMCC (Succinimidyl-4-(N-maleimidomethyl) cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio)propionamido)hexanoate), SULFO NHS LC SPDP (Sulfosuccinimidyl-6-[3-(2-pyridyldithio)propionamido)hexanoate), SPDP (N-Succinimidyl-3-(2-pyridyldithio)propionate), NHS BROMOACETATE (N-Hydroxysuccinimidylbromoacetate), NHS IODOACETATE (N-Hydroxysuccinimidyliodoacetate), MPBH (4-(N-Maleimidophenyl)butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS (N-(epsilon-Maleimidocaproyloxy)sulfosuccinimide), EMCS(N-(epsilon-Maleimidocaproyloxy)succinimide), PMPI (N-(p-Maleimidophenyl)isocyanate), KMUH (N-(kappa-Maleimidoundecanoic acid)hydrazide), LC SMCC (Succinimidyl-4-(N-maleimidomethyl)-cyclohexane-1-carboxy(6-amidocaproate)), SULFO GMBS (N-(gamma-Maleimidobutryloxy)sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy)succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), DMA (Dimethyladipimidate hydrochloride).

12. Carriers

The disclosed DOC polypeptide or DOC1 polypeptide fragments can be combined, conjugated or coupled with or to carriers and other compositions to aid administration, delivery or other aspects of the inhibitors and their use. For convenience, such composition will be referred to herein as carriers. Carriers can, for example, be a small molecule, pharmaceutical drug, fatty acid, detectable marker, conjugating tag, nanoparticle, or enzyme.

The disclosed compositions can be used therapeutically in combination with a pharmaceutically acceptable carrier. By "pharmaceutically acceptable" is meant a material that is not biologically or otherwise undesirable, i.e., the material can be administered to a subject, along with the composition, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds can be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The materials may be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:

57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

The carrier molecule can be covalently linked to the disclosed inhibitors. The carrier molecule can be linked to the amino terminal end of the disclosed peptides. The carrier molecule can be linked to the carboxy terminal end of the disclosed peptides. The carrier molecule can be linked to an amino acid within the disclosed peptides. The herein provided compositions can further comprise a linker connecting the carrier molecule and disclosed inhibitors. The disclosed inhibitors can also be conjugated to a coating molecule such as bovine serum albumin (BSA) (see Tkachenko et al., (2003) J Am Chem Soc, 125, 4700-4701) that can be used to coat microparticles, nanoparticles of nanoshells with the inhibitors.

Protein crosslinkers that can be used to crosslink the carrier molecule to the inhibitors, such as the disclosed peptides, are known in the art and are defined based on utility and structure and include DSS (Disuccinimidylsuberate), DSP (Dithiobis (succinimidylpropionate)), DTSSP (3,3'-Dithiobis (sulfosuccinimidylpropionate)), SULFO BSOCOES (Bis[2-(sulfosuccinimdooxycarbonyloxy)ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio)propionamido]butane), BSSS (Bis(sulfosuccinimdyl)suberate), SMPB (Succinimdyl-4-(p-maleimidophenyl)butyrate), SULFO SMPB (Sulfosuccinimdyl-4-(p-maleimidophenyl)butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl)aminobenzoate), SULFO SIAB (N-Sulfosuccinimidyl(4-iodoacetyl)aminobenzoate), SMCC (Succinimidyl-4-(N-maleimidomethyl) cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio)propionamido]hexanoate), SULFO NHS LC SPDP (Sulfosuccinimidyl-6-[3-(2-pyridyldithio)propionamido]hexanoate), SPDP (N-Succinimdyl-3-(2-pyridyldithio)propionate), NHS BROMOACETATE (N-Hydroxysuccinimidylbromoacetate), NHS IODOACETATE (N-Hydroxysuccinimidyliodoacetate), MPBH (4-(N-Maleimidophenyl)butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS(N-(epsilon-Maleimidocaproyloxy) sulfosuccinimide), EMCS(N-(epsilon-Maleimidocaproyloxy)succinimide), PMPI (N-(p-Maleimidophenyl)isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy)sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy)succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), DMA (Dimethyladipimidate hydrochloride).

i. Nanoparticles, Microparticles, and Microbubbles

The term "nanoparticle" refers to a nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. A nanoparticle can produce a detectable signal, for example, through absorption and/or emission of photons (including radio frequency and visible photons) and plasmon resonance.

Microspheres (or microbubbles) can also be used with the methods disclosed herein. Microspheres containing chromophores have been utilized in an extensive variety of applications, including photonic crystals, biological labeling, and flow visualization in microfluidic channels. See, for example, Y. Lin, et al., Appl. Phys Lett. 2002, 81, 3134; D. Wang, et al., Chem. Mater. 2003, 15, 2724; X. Gao, et al., J. Biomed. Opt. 2002, 7, 532; M. Han, et al., Nature Biotechnology. 2001, 19, 631; V. M. Pai, et al., Mag. & Magnetic Mater. 1999, 194, 262, each of which is incorporated by reference in its entirety. Both the photostability of the chromophores and the monodispersity of the microspheres can be important.

Nanoparticles, such as, for example, silica nanoparticles, metal nanoparticles, metal oxide nanoparticles, or semiconductor nanocrystals can be incorporated into microspheres. The optical, magnetic, and electronic properties of the nanoparticles can allow them to be observed while associated with the microspheres and can allow the microspheres to be identified and spatially monitored. For example, the high photostability, good fluorescence efficiency and wide emission tunability of colloidally synthesized semiconductor nanocrystals can make them an excellent choice of chromophore. Unlike organic dyes, nanocrystals that emit different colors (i.e. different wavelengths) can be excited simultaneously with a single light source. Colloidally synthesized semiconductor nanocrystals (such as, for example, core-shell CdSe/ZnS and CdS/ZnS nanocrystals) can be incorporated into microspheres. The microspheres can be monodisperse silica microspheres.

The nanoparticle can be a metal nanoparticle, a metal oxide nanoparticle, or a semiconductor nanocrystal. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, and uranium), boron, aluminum, gallium, indium, thallium, silicon, germanium, tin, lead, antimony, bismuth, polonium, magnesium, calcium, strontium, and barium. In certain embodiments, the metal can be iron, ruthenium, cobalt, rhodium, nickel, palladium, platinum, silver, gold, cerium or samarium. The metal oxide can be an oxide of any of these materials or combination of materials. For example, the metal can be gold, or the metal oxide can be an iron oxide, a cobalt oxide, a zinc oxide, a cerium oxide, or a titanium oxide. Preparation of metal and metal oxide nanoparticles is described, for example, in U.S. Pat. Nos. 5,897,945 and 6,759,199, each of which is incorporated by reference in its entirety.

For example, DOC1 can be immobilized on silica nanoparticles (SNPs). SNPs have been widely used for biosensing and catalytic applications owing to their favorable surface area-to-volume ratio, straightforward manufacture and the possibility of attaching fluorescent labels, magnetic nanoparticles (Yang, H. H. et al. 2005) and semiconducting nanocrystals (Lin, Y. W., et al. 2006).

The nanoparticle can also be, for example, a heat generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells.

Targeting molecules can be attached to the disclosed compositions and/or carriers. For example, the targeting molecules can be antibodies or fragments thereof, ligands for specific receptors, or other proteins specifically binding to the surface of the cells to be targeted.

ii. Liposomes

"Liposome" as the term is used herein refers to a structure comprising an outer lipid bi- or multi-layer membrane surrounding an internal aqueous solution. Liposomes can be used to package any biologically active agent for delivery to cells.

Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 µm. These MLVs were first described by Bangham, et al., J. Mol. Biol. 13:238-252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz, et al., FEBS Lett. 99:210-214 (1979)).

Liposomes can also take the form of unilamnellar vesicles, which are prepared by more extensive sonication of MLVs, and consist of a single spherical lipid bilayer surrounding an aqueous solution. Unilamellar vesicles ("ULVs") can be small, having diameters within the range of 20 to 200 nm, while larger ULVs can have diameters within the range of 200 nm to 2 µm. There are several well-known techniques for making unilamellar vesicles. In Papahadjopoulos, et al., Biochim et Biophys Acta 135:624-238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri, et al., Biochim et Biophys Acta 298:1015-1019 (1973) and the ether injection technique of Deamer, et al., Biochim et Biophys Acta 443:629-634 (1976). These methods involve the rapid injection of an organic solution of lipids into a buffer solution, which results in the rapid formation of unilamellar liposomes. Another technique for making ULVs is taught by Weder, et al. in "Liposome Technology", ed. G. Gregoriadis, CRC Press Inc., Boca Raton, Fla., Vol. I, Chapter 7, pg. 79-107 (1984). This detergent removal method involves solubilizing the lipids and additives with detergents by agitation or sonication to produce the desired vesicles.

Papahadjopoulos, et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim, et al., Biochim et Biophys Acta 728:339-348 (1983), these multivesicular liposomes are spherical and contain internal granular structures. The outer membrane is a lipid bilayer and the internal region contains small compartments separated by bilayer septum. Still yet another type of liposomes are oligolamellar vesicles ("OLVs"), which have a large center compartment surrounded by several peripheral lipid layers. These vesicles, having a diameter of 2-15 µm, are described in Callo, et al., Cryobiology 22(3):251-267 (1985).

Mezei, et al., U.S. Pat. Nos. 4,485,054 and 4,761,288 also describe methods of preparing lipid vesicles. More recently, Hsu, U.S. Pat. No. 5,653,996 describes a method of preparing liposomes utilizing aerosolization and Yiournas, et al., U.S. Pat. No. 5,013,497 describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all the aforementioned lipid vesicles and methods for their preparation are described in "Liposome Technology", ed. G. Gregoriadis, CRC Press Inc., Boca Raton, Fla., Vol. I, II & III (1984). This and the aforementioned references describing various lipid vesicles suitable for use in the invention are incorporated herein by reference.

Fatty acids (i.e., lipids) that can be conjugated to the provided compositions include those that allow the efficient incorporation of the proprotein convertase inhibitors into liposomes. Generally, the fatty acid is a polar lipid. Thus, the fatty acid can be a phospholipid The provided compositions can comprise either natural or synthetic phospholipid. The phospholipids can be selected from phospholipids containing saturated or unsaturated mono or disubstituted fatty acids and combinations thereof. These phospholipids can be dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Albaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided compositions can comprise palmitoyl 16:0.

iii. In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

C. Methods

Treatment and Prevention Methods

A method of inhibiting angiogenesis in a subject is provided comprising increasing the activity of DOC1 in the subject by an amount sufficient to inhibit angiogenesis. The activity of DOC1 can be increased by delivering exogenous DOC1 polypeptide to the subject or by delivering a molecule that enhances expression of DOC1 in the subject or in a relevant tissue of the subject.

A method of inhibiting angiogenesis in a subject is provided comprising administering to a subject a nucleic acid encoding a DOC1 polypeptide as disclosed herein, whereby a cell in the subject produces the DOC1 polypeptide, thus inhibiting angiogenesis. Any of the DOC1 polypeptides disclosed herein can by used in the present methods. For example, the wild-type DOC1 isoform 2 (NP_055705.2 (893 aa), is disclosed herein as SEQ ID NO:1.

In the disclosed methods, the administration of DOC1 polypeptide can be direct (e.g., delivery of the DOC1 polypeptide to a subject), or it can be indirect (e.g., delivery of a DOC1-expressing nucleic acid construct to the subject or delivery of a nucleic acid encoding a molecule that increases expression of DOC1 to the subject). The administration of DOC-1 polypeptide can be by any therapeutically effective mode of administration, including but not limited to oral, intravascular, intrathecal, subcutaneous, and intratumor.

In the method that calls for delivering a nucleic acid, the nucleic acid can be administered locally (e.g., to the site of a tumor). In another aspect of the method, the nucleic acid can be administered systemically. Whether delivered locally or systemically, the nucleic can be administered in a vector. The vector can be any suitable vector, including the bacteriophage AAV hybrid or other vectors disclosed herein. In one example, the nucleic acid encodes SEQ ID NO: 1. In further examples, the nucleic acid encodes a fragment of SEQ ID NO: 1. In further examples the nucleic acid encodes SEQ ID NO:2 or a fragment thereof. In further examples the nucleic acid encodes SEQ ID NO:3 or a fragment thereof. In further examples the nucleic acid encodes SEQ ID NO:4 or a fragment thereof.

In the method where a nucleic acid encoding a fragment of SEQ ID NO:1 is administered, the fragment of SEQ ID NO: 1 can be selected from the group consisting of amino acids amino acids 1-790 of SEQ ID NO: 1, amino acids 1-650 of SEQ ID NO: 1, amino acids 1-512 of SEQ ID NO: 1, amino acids 65-893 of SEQ ID NO: 1, amino acids 127-893 of SEQ ID NO: 1, and amino acids 127-650 of SEQ ID NO: 1.

Provided is a method of inhibiting tumor growth in a subject comprising increasing the activity of DOC1 in the subject by an amount sufficient to inhibit tumor growth. It is recognized that the subject being treated is in need of tumor growth inhibition, for example, after the patient is diagnosed with a tumor. The activity of DOC1 can be increased directly or indirectly in the subject by several means, including those described herein, each of which is contemplated as a manner of carrying out the invention.

Thus, provided is a method of inhibiting tumor growth in a subject is provided, comprising administering to a subject a nucleic acid encoding a DOC1 polypeptide, whereby a cell in the subject produces the DOC1 polypeptide, thus inhibiting tumor growth.

In the method that calls for delivering a nucleic acid, the nucleic acid can be administered locally (e.g., to the site of a tumor), orally, intravascularly, intrathecally, and subcutaneously. In another aspect of the method, the nucleic acid can be administered systemically. Whether delivered locally or systemically, the nucleic can be administered in a vector. The vector can be any suitable vector, including the bacteriophage AAV hybrid or other vectors disclosed herein. In one example, the nucleic acid encodes SEQ ID NO: 1 or a fragment of SEQ ID NO: 1. In a further example, the nucleic acid encodes SEQ ID NO: 2 or a fragment of SEQ ID NO: 2. In a further example, the nucleic acid encodes SEQ ID NO: 3 or a fragment of SEQ ID NO: 3. In a further example, the nucleic acid encodes SEQ ID NO: 4 or a fragment of SEQ ID NO: 4.

In the method where a nucleic acid encoding a fragment of SEQ ID NO:1 is administered, the fragment of SEQ ID NO: 1 can be selected from the group consisting of amino acids amino acids 1-790 of SEQ ID NO: 1, amino acids 1-650 of SEQ ID NO: 1, amino acids 1-512 of SEQ ID NO: 1, amino acids 65-893 of SEQ ID NO: 1, amino acids 127-893 of SEQ ID NO: 1, and amino acids 127-650 of SEQ ID NO: 1.

The inhibition of tumor growth by administration of DOC1 polypeptide can be via inhibition of cell motility and via inhibition of cell migration. The tumor growth inhibition by administration of DOC1 polypeptide can also be via increased cell apoptosis and inhibition of cell proliferation. These effects are seen on both endothelial cells and tumor cells. For example, inhibition of cell migration, apoptosis and proliferation in both endothelial cells and tumor cells are demonstrated in vitro. In vivo administration of a DOC1 fragment that targets tumor vasculature resulted in necrosis in the tumor and inhibition of tumor growth.

Provided is a method of inhibiting cell migration comprising administering a DOC1 polypeptide, or fragment thereof, or nucleic acid encoding a DOC-1 polypeptide or fragment thereof. In one embodiment, a method of inhibiting the cell migration of endothelial cells is provided. A further embodiment is a method of inhibiting the cell migration of DU145 prostate cancer cells. A further embodiment is a method of inhibiting the cell migration of cancer cells. A further embodiment is a method of inhibiting the metastasis of cancer cells. A further embodiment is a method of inhibiting the cell migration of immune system cells. A further embodiment is a method of inhibiting inflammatory disease by inhibiting the cell migration of immune system cells. In a further embodiment is a method of inhibiting cell migration of disease-causing cells Provided is a method of increasing apoptosis. In one embodiment a method of increasing apoptosis of endothelial cells is provided, comprising administering a DOC1 polypeptide, or fragment thereof, or nucleic acid encoding a DOC-1 polypeptide or fragment thereof. In a further embodiment is a method of increasing apoptosis in cancer cells. In a further embodiment is a method of increasing apoptosis in disease-causing cells.

Provided is a method of treating cancer in a subject comprising increasing the activity of DOC1 in the subject by an amount sufficient to treat cancer. It is recognized that the subject being treated is in need of treatment for cancer, for example, after the patient is diagnosed with cancer. The activity of DOC1 can be increased in the subject by several means, including those described herein, each of which is contemplated as a manner of carrying out the invention.

A representative but non-limiting list of cancers that the disclosed methods compositions can be used to treat is the following: lymphoma (Hodgkins and non-Hodgkins), B cell lymphoma, T cell lymphoma, AIDS-related lymphomas, hematopoietic cancers, mycosis fungoides, Hodgkin's Disease, leukemias, myeloid leukemia, myelomas, carcinomas of solid tissues bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers, testicular cancer, colon and rectal cancers, prostatic cancer, or pancreatic cancer, squamous cell carcinomas, squamous cell carcinomas of the mouth, throat, larynx, and lung, adenocarcinomas, sarcomas, gliomas, high grade gliomas, blastomas, neuroblastomas, plasmacytomas, histiocytomas, melanomas, adenomas, hypoxic tumors, AIDS-related sarcomas, metastatic cancers, or cancers in general.

In the cancer treatment method that calls for delivering a nucleic acid, the nucleic acid can be administered locally (e.g., to the site of a tumor). In another aspect of the method, the nucleic acid can be administered systemically. Whether delivered locally or systemically, the nucleic can be administered in a vector. The vector can be any suitable vector, including the bacteriophage AAV hybrid or other vectors disclosed herein. In one example, the nucleic acid encodes SEQ ID NO: 1. For example the nucleic acid can be any nucleic acid shown in SEQ ID NO:7 or any other coding sequence for SEQ ID NO:1.

In further examples, the nucleic acid encodes a fragment of SEQ ID NO: 1. In the method where a nucleic acid encoding a fragment of SEQ ID NO:1 is administered, the nucleic acid encoding a fragment of SEQ ID NO: 1 can be selected from the group consisting of nucleic acids that encode amino acids 1-790 of SEQ ID NO: 1, amino acids 1-650 of SEQ ID NO: 1, amino acids 1-512 of SEQ ID NO: 1, amino acids 127-512 of SEQ ID NO:1, amino acids 65-893 of SEQ ID NO: 1, amino acids 127-893 of SEQ ID NO: 1, amino acids 127-650 of SEQ ID NO: 1 and amino acids 127-790 of SEQ ID NO:1. More specifically, the nucleic acid encoding a DOC1 polypeptide having anti-proliferative activity can be selected from the group of nucleic acids consisting nucleic acids encoding amino acids 1-790 of SEQ ID NO:1, amino acids 1-650 of SEQ ID NO:1, amino acids 1-512 of SEQ ID NO:1, and amino acids 127-893 of SEQ ID NO:1.

Numerous anti-cancer drugs are available for combination with the present method and compositions. The following are lists of anti-cancer (anti-neoplastic) drugs that can be used in conjunction with the presently disclosed DOC1 activity-enhancing or expression-enhancing methods.

Antineoplastic: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocannycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin;

propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

1. Administration

The disclosed compounds and compositions can be administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The exact amount of the compositions required can vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. Thus, effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage can vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products.

For example, a typical daily dosage of the DOC1 or DOC1 polypeptide comprising a DOC1 fragment used alone might range from about 1 µg/kg to up to 100 mg/kg of body weight or more per day, depending on the factors mentioned above. More specifically, from about 0.1 mg to about 10 mg/kg of body weight or more per day can be administered. In another embodiment a DOC1 polypeptide (e.g., aa1-790 of SEQ ID NO:1)-expressing phage is administered directly to a tumor to increase DOC1 polypeptide presence in the tumor. An effective amount of DOC1 polypeptide expression in a tumor being treated can range from 2-300 fold more mRNA expression than in a corresponding control. For example, a treatment regimen can include DOC1-expressing phage ($1\times10^{11}$ TU per dose) injected intravenously twice at day 0 and day 7 and continuing as long as required.

Following administration of a disclosed composition for treating, inhibiting, or preventing cancer, the efficacy of the therapeutic DOC1 or DOC1 polypeptide comprising a DOC1 fragment can be assessed in various ways well known to the skilled practitioner. For instance, one of ordinary skill in the art will understand that a composition disclosed herein is efficacious in treating cancer or inhibiting tumor growth in a subject by observing that the composition reduces tumor size or prevents a further increase in tumor load. Tumor size, tumor load, etc., can be measured by methods that are known in the art.

The disclosed DOC1 polypeptide compositions that inhibit angiogenesis and reduce tumor size disclosed herein may be administered prophylactically to patients or subjects who are at risk for cancer or who have been newly diagnosed with cancer.

Other molecules that interact with DOC1 which do not have a specific pharmaceutical function, but which may be used for the delivery of diagnostic tools for example can be delivered in ways similar to those described for the pharmaceutical products.

The disclosed compositions and methods can also be used for example as tools to isolate and test new drug candidates for a variety of neoplastic diseases.

Screening/Diagnostic Methods

A method of diagnosing cancer in a subject is provided. The method comprises measuring the amount of DOC1 expression in a subject, the lower the level of DOC1, the more likely a cancer exists in the subject. The present diagnostic and classifying methods are expected to be useful for the cancers described herein, particularly, epithelial cancers, e.g., colon cancer and prostate cancer.

A method for classifying a cancer in a subject is provided. The method can comprise the steps of contacting a test sample from a subject with an anti-DOC1 antibody; detecting the binding of the anti-DOC1 antibody to a DOC1 polypeptide in the test sample; comparing the expression level of the DOC1 polypeptide in the test sample with the expression level of a DOC1 polypeptide in a reference sample for which a cancer classification is known; and identifying a difference, if present, in the expression level of the DOC1 polypeptide in the test sample and reference sample, thereby classifying the cancer in the subject. The difference in the expression level of the DOC1 polypeptide in the test sample as compared to the reference sample indicates that the test sample has a different classification as the reference sample. A similar expression level of the DOC1 polypeptide in the test sample as compared to the reference sample indicates that the test sample has the same classification as the reference sample. In the method of classifying a cancer, the reference sample can be a sample from a subject with a known classification. Alternatively, in the method of classifying a cancer, the reference sample can be from a database. Further, the reference sample can be classified as a normal sample or the reference sample can be classified as cancerous.

A method for identifying a stage of cancer in a subject is provided. The method can comprise contacting a test sample from a subject with an anti-DOC1 antibody; detecting the binding of the anti-DOC1 antibody to a DOC1 polypeptide in the sample; comparing the expression level of the DOC1 polypeptide in the test sample with the expression level of a DOC1 polypeptide in a reference sample for which a stage of cancer is known; and identifying a difference, if present, in the expression level of the DOC1 polypeptide in the test sample and reference sample, thereby identifying the stage of cancer in the subject. A difference in the expression level of the DOC1 polypeptide in the test sample as compared to the reference sample indicates that the test sample has a different stage of cancer than the reference sample. A similar expression level of the DOC1 polypeptide in the test sample as compared to the reference sample indicates that the test sample has the same stage of cancer as the reference sample. The reference sample can be from a patient with a known stage of cancer. Alternatively, the reference sample is from a database.

A method of determining the efficacy of an anti-cancer treatment is provided, The method can comprise determining the expression level of a DOC1 polypeptide in a sample obtained from the subject; administering the anti-cancer treatment; determining the expression level of a DOC1 polypeptide in a sample obtained from the subject after administration of the anti-cancer treatment; and comparing the expression level of the DOC1 polypeptide in the sample obtained after the anti-cancer treatment with the sample obtained in step a) such that if there is a change in the expression level of the DOC1 polypeptide in the sample obtained after the anti-cancer treatment as compared to the sample obtained before administration of the anti-cancer treatment, wherein the change is associated with an improvement in the subject, the anti-cancer therapeutic is an effective anti-cancer therapeutic. The change can be an increase in the expression levels of the DOC1 polypeptide.

There are contexts in which the a decrease in the expression levels of the DOC1 polypeptide is desired. For example, conditions caused by excessive DOC1-induced apoptosis, can be treated by reducing/decreasing levels of DOC1.

Thus, provided is a method of identifying a modulator of DOC1 expression. The method can comprise a) contacting a cell that is capable of expressing DOC1 with a putative modulator; measuring DOC1 expression, wherein a change in DOC1 expression in the cell of step a) as compared to a cell that was not contacted with the putative modulator indicates the presence of a modulator of DOC1 expression. The modulator of DOC1 expression can increase DOC1 expression. Angiogenesis inhibitors such as endostatin, fumagillin and EMAP II upregulate DOC1 expression. For example, the human prolactin antagonist, G129R, can inhibit human breast cancer cell proliferation in vitro and to slow the growth rate of tumors in mice (Beck et al., Cancer Res. 2003 Jul. 1; 63(13): 3598-604). The modulator of DOC1 expression can decrease DOC1 expression. For example, DOC1 expression can be silenced using small interfering RNA (Tandle et al. Cytokine 2005 Jun. 21; 30(6):347-58). The siRNA used in this experiment were pSiRNA-Neo-DOC1: 5'AGCGTAACCAAG-GAGAGAGAT3' (accession number XM_002964, position 1172-1192; SEQ ID NO:5); and pSiRNA-Neo-Control: 5'ATTCATTCATTCATTCACCAT3' (accession number D00269, position 1192-1212; SEQ ID NO:6)

DOC1 expression can be measured by amplifying a DOC1 nucleic acid. As the sequence of the nucleic acid is provided, the generation and use of DOC1 amplifying primers is routine. DOC1 expression can be measured by detecting a DOC1 polypeptide. In the method that measures DOC1 expression by detecting DOC1 polypeptide, the DOC1 polypeptide can be detected using anti-DOC1 antibody, for example the antibody described herein.

Thus, method of detecting DOC1 in a fluid or tissue of a subject is provided, comprising: contacting a sample obtained from the subject with an anti-DOC1 antibody; and determining the presence of a DOC1 polypeptide in the sample.

D. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for detecting DOC1 in a tissue or blood, the kit comprising anti-DOC1 antibody. The kits also can contain a detectable labels for detecting an antibody-DOC1 complex.

E. Uses

The disclosed compositions can be used in a variety of ways as research tools. For example, the disclosed compositions, such the anti-DOC1 antibody can be used to study the tissue distribution of DOC1 to confirm the reliability of using its expression level as an indicator of cancer or non-cancer status. The antibody can also be used in a method to stage cancer. The antibody can also be used in a method a method of determining the efficacy of an anti-cancer treatment. The antibody can also be used in a method a method of identifying a modulator of DOC1 expression. Other uses are disclosed, apparent from the disclosure, and/or will be understood by those in the art.

F. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

2. Peptide Synthesis

One method of producing the disclosed proteins, such as SEQ ID NO:23, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

3. Process for Making the Compositions

Disclosed are processes for making the compositions as well as making the intermediates leading to the compositions. For example, disclosed are the nucleic acid shown in SEQ ID NO:7, and every degenerate nucleic encoding SEQ ID NO:1, SEQ ID NO:2, SEQ ID NO:3 or SEQ ID NO:4. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid comprising the sequence set forth in SEQ ID NO:7 (or functional DOC1 fragment-encoding nucleic acid fragment), or any degenerate sequence encoding SEQ ID NO:1, SEQ ID NO:2, SEQ ID NO:3 or SEQ ID NO:4, to a sequence controlling the expression of the nucleic acid.

Also disclosed are nucleic acid molecules produced by the process comprising linking in an operative way a nucleic acid molecule comprising a sequence having 80% identity to a sequence set forth in SEQ ID NO:7, or 80% identity to any degenerate sequence encoding SEQ ID NO:1, SEQ ID NO:2, SEQ ID NO:3 or SEQ ID NO:4, and a sequence controlling the expression of the nucleic acid.

Disclosed are nucleic acid molecules produced by the process comprising linking in an operative way a nucleic acid molecule comprising a sequence that hybridizes under stringent hybridization conditions to a sequence set forth SEQ ID NO:7, or to any degenerate sequence encoding SEQ ID NO:1, SEQ ID NO:2, SEQ ID NO:3 or SEQ ID NO:4, and a sequence controlling the expression of the nucleic acid.

Disclosed are nucleic acid molecules produced by the process comprising linking in an operative way a nucleic acid molecule comprising a sequence encoding a peptide set forth in SEQ ID NO:1, SEQ ID NO:2, SEQ ID NO:3 or SEQ ID NO:4, and a sequence controlling an expression of the nucleic acid molecule.

Disclosed are nucleic acid molecules produced by the process comprising linking in an operative way a nucleic acid molecule comprising a sequence encoding a peptide having 80%, 90%, 91%, 92%, 93%, 94%, 95%, 96%, 97%, 98%, or 99% identity to any peptide set forth in SEQ ID NO:1, SEQ ID NO:2, SEQ ID NO:3 or SEQ ID NO:4 and a sequence controlling an expression of the nucleic acid molecule.

Disclosed are nucleic acids produced by the process comprising linking in an operative way a nucleic acid molecule comprising a sequence encoding a peptide having 80%, 90%, 91%, 92%, 93%, 94%, 95%, 96%, 97%, 98%, or 99% identity to any peptide set forth in SEQ ID NO:1, SEQ ID NO:2, SEQ ID NO:3 or SEQ ID NO:4, wherein any change from SEQ ID NO:1, SEQ ID NO:2, SEQ ID NO:3 or SEQ ID NO:4 are conservative changes and a sequence controlling an expression of the nucleic acid molecule.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

G. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Figure 1B:
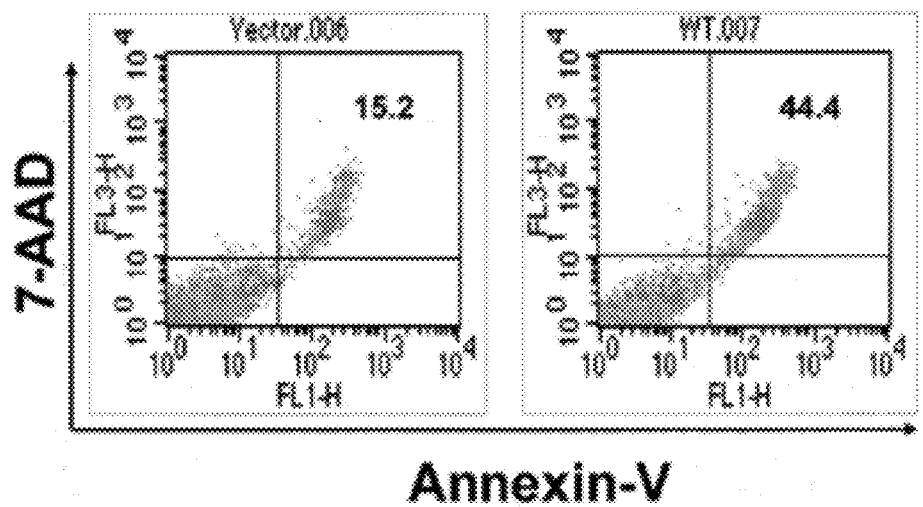
Figure 2A:
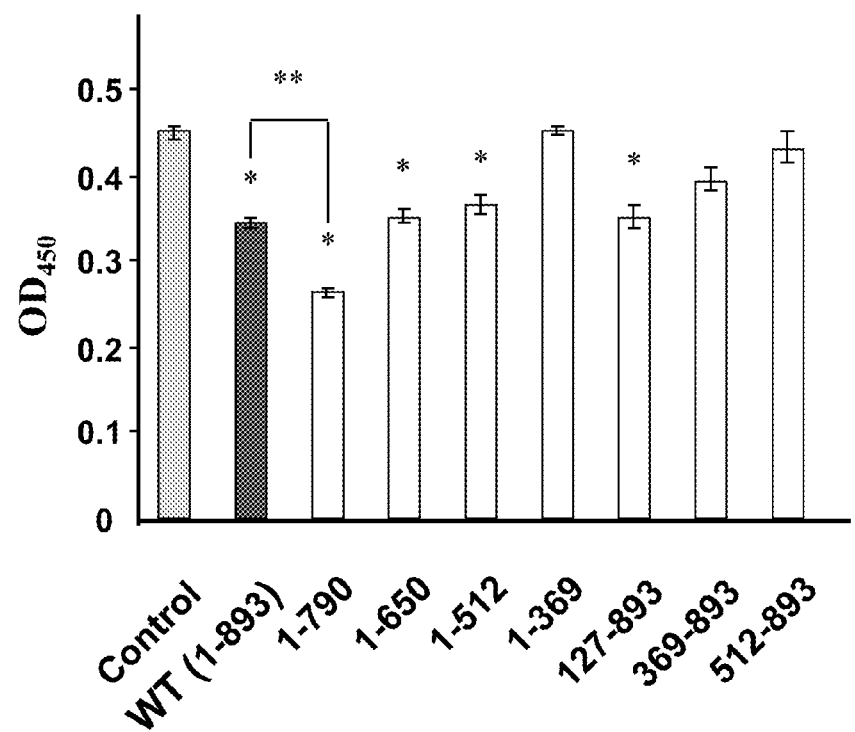
FIG. 2 shows that FILIP1L truncation mutants have differential activity in mediating anti-proliferative activity (A) Differential inhibition of HUVECs proliferation by FILIP1L truncation mutants was analyzed by BrdU ELISA 24 h after transfection. Error bars indicate SEM (n=4). FILIP1L truncation mutants 1-790 (P=0.0001), 1-650 (P=0.004), 1-512 (P=0.0114) and 127-893 (P=0.0021) significantly inhibited cell proliferation compared to control. C-terminal mutant 1-790 was more potent than wild-type FILIP1L in mediating anti-proliferative activity (P=0.001). The result is a representative of two independent experiments. Additional N-terminal (B) and C-terminal (C) mutants were also tested.
Figure 2B:
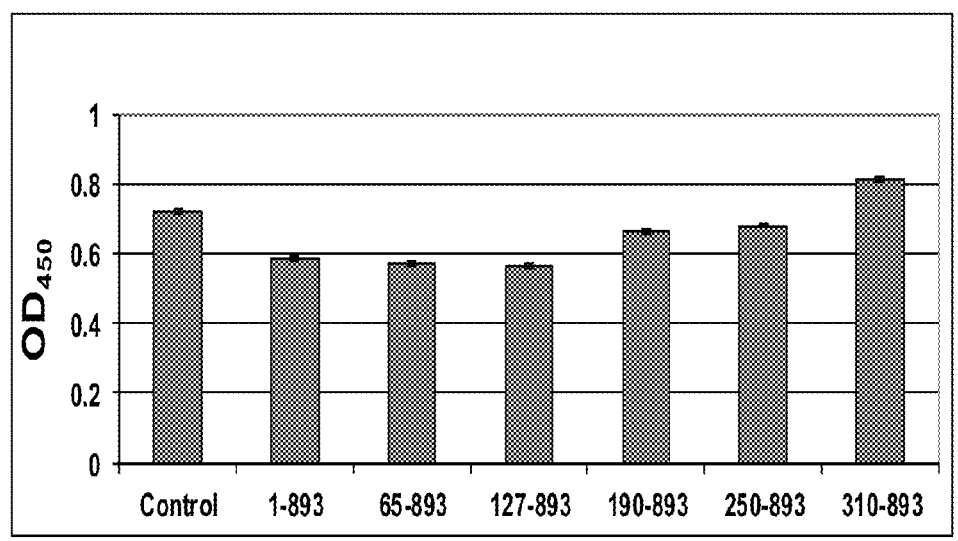
Figure 2C:
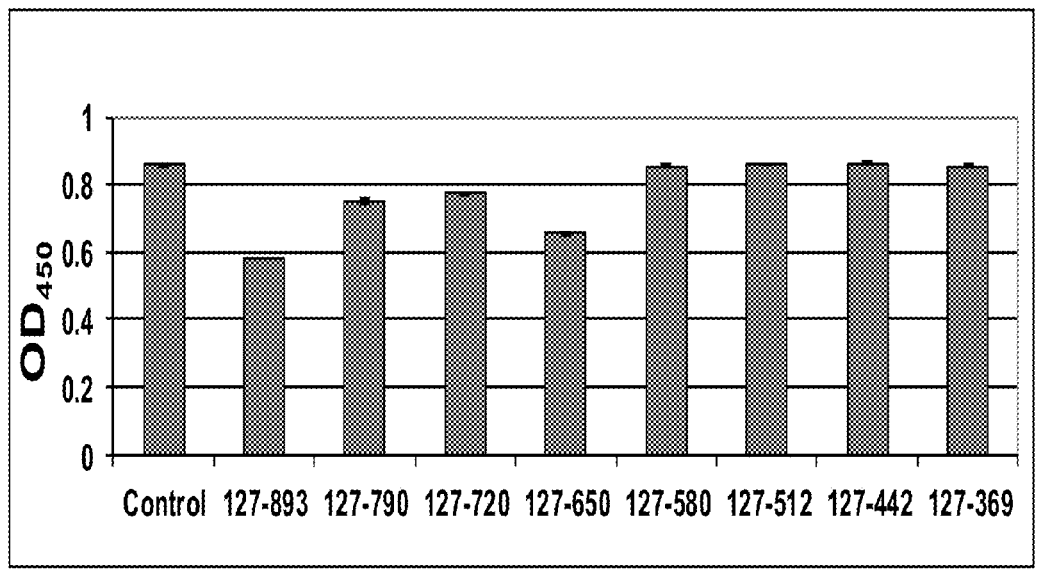

Functional Studies of DOC1 and Selected Truncation Fragments; Novel Proteins that Inhibit Angiogenesis and Inhibit Tumor Growth Over-expression of DOC1 in endothelial cells leads to inhibition of cell proliferation and an increase in apoptosis. In particular, DOC1 over-expression inhibited cell proliferation by 25 percent compared to controls as determined by BrdU labeling (FIG. 1A), and increased apoptosis 3-fold compared to controls as determined by Annexin V and 7-AAD staining (FIG. 1B). In addition, over-expression of DOC1 fragments in a series of DOC1 truncation mutants showed differential activity in terms of the inhibition of cell proliferation as determined by BrdU labeling (FIG. 2A-C). Based on these truncation studies, an active region that mediates the inhibition of cell proliferation can be placed between aa127 and aa512, and C-terminal mutant 1-790 is more potent than wild-type DOC1 in mediating anti-proliferative activity. Stable clones expressing DOC1 C-terminal mutant 1-790 showed slower cell migration than those expressing control vector (FIG. 3), indicating that overexpression of DOC1 results in inhibition of cell migration. Administration of DOC1 truncation mutant (aa1-790) by vasculature-targeting bacteriophage into tumor-bearing nude mice resulted in the inhibition of M21 melanoma growth (FIG. 5; Example 3).

Example 2

Mouse Monoclonal DOC1 Antibody

A mouse monoclonal DOC1 antibody was developed, which allowed detection of endogenous DOC1 protein in human tissues for the first time. The antibody, was produced by standard methods. $His_6$ and MBP fusion constructs encoding a full length FILIP1L cDNA were generated. The fusion construct was expressed in Baculovirus, the fusion protein was purified and was cleaved by TEV protease. We then used the intact FILIP1L protein as an antigen to immunize mice. Mouse monoclonal antibodies were screened by ELISA and Western blot using the purified FILIP1L protein, and monoclonal antibodies from clone 3C5 and 1C2 were selected.

Figure 4:
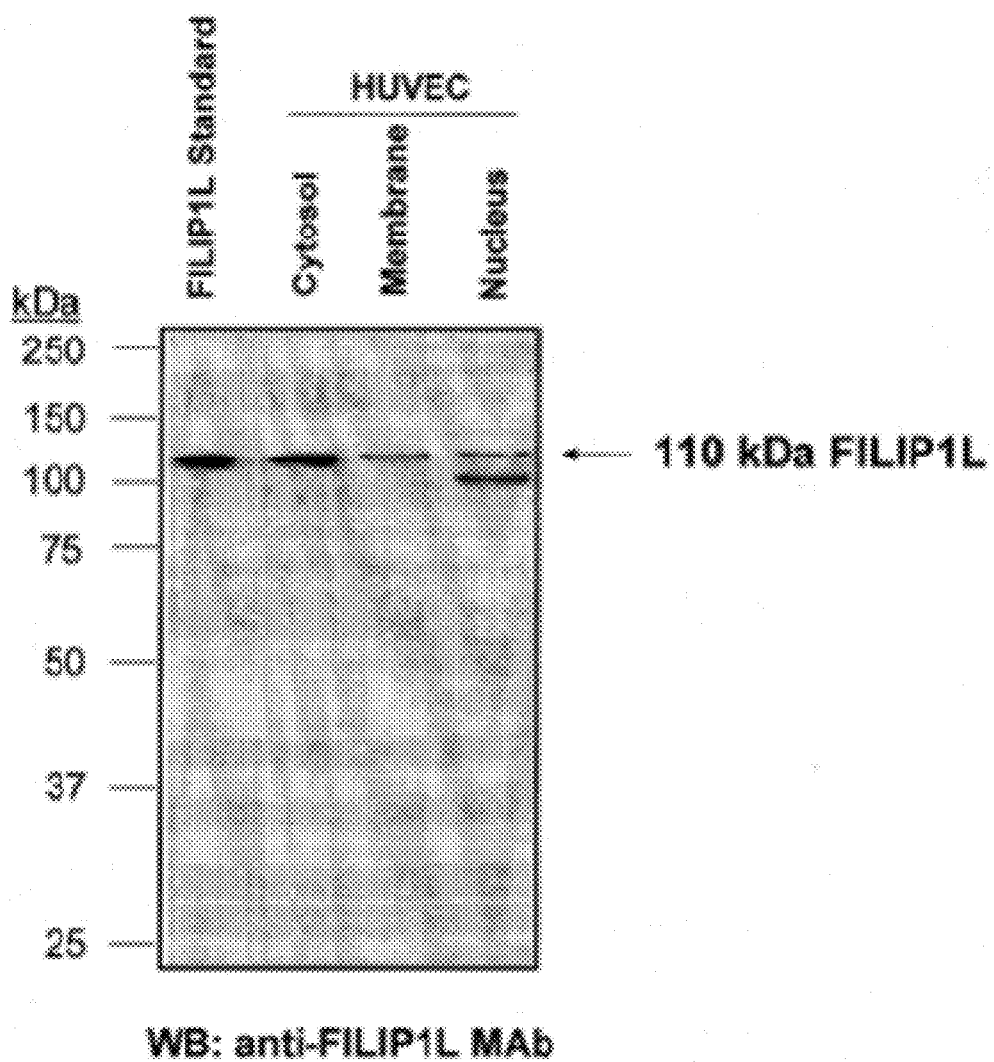
FIG. 4 shows that FILIP1L protein is present in human endothelial cells A 110 kDa FILIP1L protein was detected in the cytoplasm, membrane and nucleus of HUVECs by Western blot using FILIP1L antibody. A purified FILIP1L protein was used as a standard.

DOC1 protein is expressed in the cytoplasm, on the membrane and in the nucleus of endothelial cells (FIG. 4). Immunohistochemical staining showed that DOC1 protein is expressed on the vasculature, stroma and muscularis in human cancer patient specimens (FIG. 5A). DOC1 appears to be more expressed in foci of inflammation in cancer stroma (e.g. chronic prostatitis) in these cancer patient specimens. In normal human colon, FILIP1L was expressed in the vasculature and muscularis mucosa (smooth muscle type stroma) determined by immunohistochemical staining of FILIP1L. FILIP1L appears to be more expressed in foci of inflammation in human prostate cancer stroma (e.g. chronic prostatitis).

The antibodies from clones 3C5 and 1C2 tested for binding against DOC1 polypeptides. 293 cells were transfected with the plasmid encoding each construct, harvested cells after 24 h, and the cell lysates were subjected to Western blot analysis using the antibody. In addition to binding the DOC1 of SEQ ID NO:1, this antibody specifically detects wild-type, 1-790 (SEQ ID NO:1) and 1-650 (SEQ ID NO:2).

Example 3

In Vivo Activity of DOC1 Functional Fragments

Figure 5:
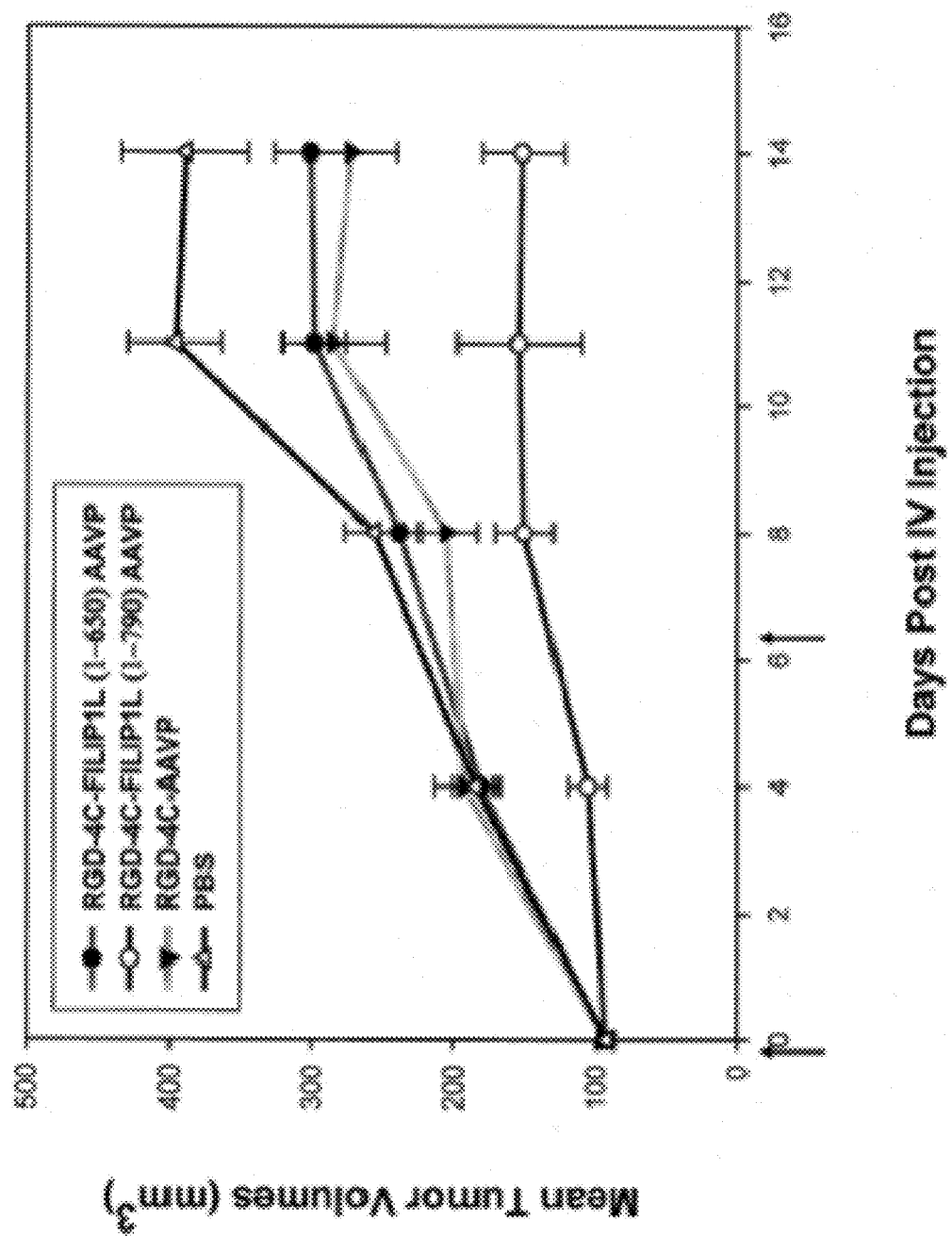
FIG. 5 shows targeted expression of FILIP1L C-terminal mutant 1-790 in tumor vasculature results in inhibition of tumor growth in vivo. Tumors from RGD-4C-FILIP1L (1-790) AAVP-treated mice (empty circles) were significantly smaller than those from PBS-treated mice (empty triangles) in M21 xenograft model by day 14 (P=0.0062). Tumors from RGD-4C-FILIP1L (1-790) AAVP-treated mice (empty circles) were also significantly smaller than those from RGD-4C AAVP-treated mice (filled triangles; P=0.0344) and RGD-4C-FILIP1L (1-650) AAVP-treated mice (filled circles; P=0.0053) by day 14. Error bars indicate SEM (n=11). The result is a representative of two independent experiments.

An in vivo experiment using M1 phage to treat mice provided the results shown in FIG. 5. A bacteriophage AAV hybrid vector containing a DOC1 fragment that targets tumor vasculature was administered. This resulted in necrosis in the tumor and subsequent inhibition of tumor growth.

It has been recently shown that a new hybrid adeno-associated virus/phage (AAVP) specifically targets tumor vasculature in a mouse model (Hajitou A et al. 2006 Cell 125:385-398)). Specifically, a eukaryotic gene cassette from adeno-associated virus was inserted into RGD-4C phage which displays the double-cyclic peptide CDCRGDCFC (RGD-4C). Since the RGD-4C peptide binds to $\alpha_v$ integrins which are overexpressed in tumor vasculature, the hybrid AAVP could specifically target tumor vasculature. AAVP specifically targets tumor vasculature in several different tumor models, and in both immunosuppressed and immunocompetent mice. To test if targeted expression of DOC1 in tumor vasculature resulted in inhibition of tumor growth, the AAVP system was utilized. M21 melanoma cells were injected subcutaneously onto the female athymic nude mice, and grown to the average size of 100 $mm^3$. Mice were randomly sorted to four groups (n=11 for each group), phages ($1 \times 10^{11}$ TU per dose) were injected intravenously twice at day 0 and day 7, and the tumors were measured in a blinded manner. Four groups were tested: PBS, RGD-4C AAVP, RGD-4C-DOC1 (1-650) and RGD-4C-DOC1 (1-790) AAVP. The PBS control tumors were grown fast and some of the tumors started to show necrosis in the center of tumor by day 14, so the tumors were measured until day 14. Only tumors from RGD-4C-DOC1 (1-790) AAVP-treated mice were significantly smaller than those from PBS-treated mice by day 14 (P=0.0062). In addition, tumors from RGD-4C-DOC1 (1-790) AAVP-treated mice were significantly smaller than those from RGD-4C AAVP-treated mice (P=0.0344) and RGD-4C-DOC1 (1-650) AAVP-treated mice (P=0.0053) by day 14.

In this experiment, it was shown that 1-790 had a potent anti-tumor activity. Therefore, DOC1 and its truncation fragments are shown herein to be mediators of the anti-proliferative and apoptotic activity in endothelial cells and tumor cells. The DOC1 fragments can be utilized as cancer therapeutics.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Example 4

Functional Characterization of Filamin A Interacting Protein 1-Like Production of Mouse Monoclonal Anti-FILIP1L Antibody The construct encoding a full length FILIP1L cDNA was generated and expressed in Baculovirus. The purified full-length FILIP1L protein (893 amino acids) was used as an antigen to immunize mice. Immunization of mice, production of hybridoma cells, screening by enzyme-linked immunosorbent assay (ELISA) and purification of monoclonal antibody were performed by Green Mountain Antibodies Inc. Antibodies that recognize FILIP1L were further tested by western blot and a monoclonal antibody was selected.

Cell Culture

HUVECs were cultured in complete EGM-2 medium as recommended by the manufacturer (Lonza). HEK293 cells were grown in Dulbecco modified Eagle medium containing 10% FBS. DU145 human prostate carcinoma cells and M21 human melanoma cells were grown in RPMI 1640 medium containing 10% FBS.

Western Blot

HUVECs were cultured, harvested and fractionated with ProteoExtract Subcellular Proteome Extraction Kit according to the manufacturer's protocol (Calbiochem). For endostatin experiment, HUVECs were starved in EGM-2 basal medium containing 1% FBS for 16 h, treated with 1 µg/ml endostatin for 2, 4 and 8 h, and lysed with radioimmuno precipitation assay (RIPA) buffer. HEK293 cells were transfected, using Lipofectamine 2000 (Invitrogen), with a series of N-terminal and C-terminal truncation mutants of FILIP1L containing a C-terminal hemagglutinin (HA) tag, harvested at 24 h and lysed with RIPA buffer. Empty lentivirus- or lentivirus expressing FILIP1L mutant 1-790 (here-after referred to as FILIP1LΔC103)-transduced DU145 clones were cultured in the presence or absence of 1 µg/ml doxycycline and lysed with RIPA buffer. Tumors from PBS-, null-adeno-associated virus-phage (here-after referred to as AAVP-null)- and AAVP expressing FILIP1LΔC103 (here-after referred to as AAVP-ΔC103)-treated mice were removed 4 days after tail vein injection and snap frozen. Whole tumor lysates were prepared from RIPA buffer lysis of 60 µm tumor section. 25-50 µg cellular fractionation, whole cell lysates or whole tumor lysates prepared by above methods were separated on SDS-PAGE and transferred to nitrocellulose membrane. The membranes were blotted with antibodies against FILIP1L, HA tag (Covance) and glyceraldehyde 3-phosphate dehydrogenase (GAPDH) (Chemicon) followed by incubation with anti-mouse antibody conjugated to horseradish peroxidase. The signal was detected using chemiluminescence (Millipore).

Immunohistochemistry

Frozen human colon tumors and their adjacent normal colon samples were obtained under an IRB approved protocol. 10 µm tissue sections were fixed with 4% paraformaldehyde for 20 min and stained with mouse monoclonal antibodies against FILIP1L (7.5 µg/ml) and CD31 (10 µg/ml, DAKO). After visualization of staining by DAB (3,3'-diaminobenzidine tetrahydrochloride), the slides were counterstained with hematoxylin. Images were acquired by Axioplan 2 microscope using a 20×/0.75 objective with Axiovision 4.1 software (Zeiss).

Immunofluorescence and Vessel Density Determination

HUVECs were starved in EGM-2 basal medium containing 1% FBS for 16 h and treated with 1 µg/ml endostatin for 4 h. The cells were fixed with 4% paraformaldehyde for 10 min followed by permeabilization with 0.1% Triton X-100 for 5 min. The cells were washed with PBS, blocked with 5% bovine serum albumin in PBS and treated with mouse anti-FILIP1L antibody (4 µg/ml) preincubated with 500 fold molar excess of either bovine serum albumin (BSA) or FILIP1L. The cells were then incubated with 2 µg/ml Alexa Fluor 488 anti-mouse IgG (Invitrogen) and treated with 4,6-diamidino-2-phenylindole (DAPI) mounting media (Vector Laboratories). Images were acquired on a LSM-510 confocal microscope using a 25×/0.8, 40×/1.3 or 63×/1.4 objective and analyzed by AxioVision LE software (Zeiss). For AAVP-targeting experiment, tumors from PBS-, AAVP-ΔC103- and AAVP-ΔC243-treated mice were removed at 30 min and 6 days after tail vein injection (30 min only for PBS-treated tumor), snap frozen and cut into 10 µm tumor sections. These tumor sections were subjected to immunofluorescent staining as described above except rabbit anti-AAVP antibody (Sigma) followed by Alexa Fluor 594 anti-rabbit IgG (Invitrogen) and rat anti-CD31 antibody (BD Pharmingen) followed by Alexa Fluor 488 anti-rat IgG (Invitrogen) were used.

CD31-stained tumor sections from PBS-, AAVP-null- and AAVP-ΔC103-treated mice were analyzed for vessel density as described in Blansfield J A et al. Clin Cancer Res 2008; 14:270-80, which is herein incorporated by reference for at least material related to the analysis of vessel density. Three tumors from each treatment group were analyzed. Five random fields per tumor were imaged by Axiovert 200M microscope using a 10×/0.3 objective (Zeiss). Axiovision 4.6 software (Zeiss) was used to quantify CD31-positive vessels. In addition, TUNEL staining was also performed on these AAVP-treated tumors as recommended by the manufacturer (Promega Corporation). Images were taken by Axiovert 200M microscope using a 5×/0.15 objective (Zeiss).

Transfection of HUVECs with FILIP1L Plasmids

Plasmids encoding wild-type as well as truncation mutants of FILIP1L were purified using Endo-free maxiprep kit (Qiagen). HUVECs were transfected with equimolar amount of each DNA using HUVEC nucleofector solution and Nucleofector II machine as provided by the manufacturer (Amaxa). Transfection efficiency was verified using a plasmid with an enhanced green fluorescent protein (eGFP) marker (2 µg) as was calculated by the GFP expression. The percentage of transfection reached by this method was 50±10%. After transfection, the cells were subjected to proliferation, apoptosis or migration assays.

Bromodeoxyuridine (BrdU) ELISA Cell Proliferation Assay

The transfected HUVECs were plated with $2 \times 10^4$ cells/well in 96 well culture plates and incubated for 24 h. Cell proliferation was measured by Cell Proliferation Biotrak ELISA (GE Healthcare) as recommended by the manufacturer.

Apoptosis Assay

The transfected HUVECs were plated with $2.5 \times 10^4$ cells/well in white-walled 96 well culture plates and incubated for 24 h. Early apoptosis was determined by the measurement of caspase 3/7 activity using the Caspase-Glo 3/7 Assay (Promega Corporation) following manufacturer's instructions. The transfected HUVECs were plated with $2 \times 10^6$ cells/100 mm culture dishes and incubated for 48 h. Late stage apoptosis was determined by the staining of annexin V-fluorescein isothiocyanate (FITC) and 7-amino-actinomycin D (7-AAD) staining using the Annexin V-FITC Apoptosis Detection Kit (BD Pharmingen) following manufacturer's instructions. The stained cells were subjected to flow cytometric analysis using a FACSCalibur (BD) and analyzed by the CELLQuest program.

Migration Assay

The migratory potential of the transfected HUVECs was assessed by Electric Cell-Substrate Impedance Sensing (ECIS Model 9600, Applied Biophysics Inc. (Giaever I and Keese CR. Nature 1993; 366:591-2; Keese C R et al. Proc Natl Acad Sci USA 2004; 101:1554-9). $1.1 \times 10^5$ cells were inoculated in 8W1E+ plates in complete EGM-2 medium. The cells were allowed to completely adhere to the electrodes which produced maximum and non variable readings of impedance. The monolayers were then wounded (30 seconds, 4.0 V, 60 kHz) where impedance became a minimum. As cells migrated to heal the wound, the impedance was recorded at 15 kHz every 5 seconds for 10 hours in real time. The differences in migration rate were evaluated by comparison of the slopes of the curves in linear range for early time points.

DU145 clones transduced with either empty lentivirus or lentivirus expressing FILIP1LΔC103 ($7.5 \times 10^4$ cells/chamber) were plated in the presence or absence of 1 μg/ml doxycycline in upper chamber. Migration toward 10% FBS was measured at 15 h by QCM 24-well colorimetric cell migration assay kit (Chemicon) as recommended by the manufacturer.

Cloning of FILIP1L and its Truncation Mutants

Genes for FILIP1L and its truncation mutants were cloned into Gateway entry clones using multi-step PCR. The subsequent entry clones were sequence verified throughout the entire cloned region. Entry clones were then subcloned by Gateway LR recombination using the manufacturer's protocols (Invitrogen) into different expression vectors.

Lentivirus Generation and Development of Inducible Clones Overexpressing FILIP1LΔC103

A lentiviral construct encoding FILIP1LΔC103 was used to generate lentivirus expressing FILIP1LΔC103 by the ViraPower™ T-REx™ Lentiviral Expression System (Invitrogen) using the manufacturer's protocols. DU145 cells were transduced with the Tet repressor-lentivirus, and screened for clones that expressed the Tet repressor by western blot analysis. Tet repressor-expressing DU145 cells were then transduced with either empty lentivirus or lentivirus expressing FILIP1LΔC103, and stable clones were screened by real time RT-PCR analysis.

Quantitative Real-Time RT-PCR

DU145 clones transduced with lentivirus expressing FILIP1LΔC103 were cultured in the presence or absence of 1 μg/ml doxycycline for 48 h and harvested. Total RNA was prepared by RNeasy kit (Qiagen) and cDNA was prepared by Superscript II reverse transcriptase (Invitrogen). qPCR was performed using ABI 7500 SDS real-time PCR instrument following manufacturer's instructions (Applied Biosystems). The expression of the FILIP1L gene was normalized to GAPDH expression. The primers used were: 5'-AACGCTG-GTATCATGGCTGAA-3' (SEQ ID NO:9) and 5'-ATCTCT-GCACTGCTCCTCCATT-3' (SEQ ID NO:10) for FILIP1L; 5'-TCACCAGGGCTGCTTTTAACTC-3' (SEQ ID NO:11) and 5'-GGAATCATATTGGAACATGTAAACCA-3' (SEQ ID NO:12) for GAPDH.

Construction and Generation of Targeted AAVP Particles

Cloning of both FILIP1LΔC103 (amino acid 1-790) and FILIP1LΔC243 (amino acid 1-650) mutant cDNA into the AAVP vector and the production of AAVP was performed as described previously (Hajitou A et al. Nat Protoc 2007; 2:523-31; Hajitou A et al. Cell 2006; 125:385-98).

Xenograft Assay

M21 human melanoma cells were injected subcutaneously into female athymic nude mice, and grown to an average size of 100 mm³. Mice were randomly sorted into four groups (n=11 for each group), AAVP ($1 \times 10^{11}$ transducing units per dose) was injected intravenously at day 0 and day 7, and tumors were measured in a blinded manner. Tumor volume was calculated as the product of (length×width×height)×0.52. All animal experiments were conducted according to protocols approved by the NIH Animal Care and Use Committee.

Statistical Analysis

Statistical analyses were performed using a two-tailed Student's t test (GraphPad Prism 3.0) and differences were considered to be statistically significant at a value of P less than 0.05. Xenograft and vessel density data were analyzed using One-way analysis of variance with Newman-Keuls Multiple Comparison Test. A P value less than 0.05 was considered significant.

Results

Expression of FILIP1L Protein in HUVECs and Human Tissue

Although FILIP1L mRNA expression has been shown to be upregulated in human endothelial cells in response to different angiogenesis inhibitors (Mazzanti C M et al. Genome Res 2004; 14:1585-93; Tandle A T et al. Cytokine 2005; 30:347-58), the expression of FILIP1L protein has not been previously investigated. To determine whether FILIP1L protein is endogenously expressed in human tissue, monoclonal antibodies that specifically recognize FILIP1L were produced. To detect FILIP1L protein in endothelial cells and to determine its subcellular localization, HUVECs were fractionized and a western blot was performed using anti-FILIP1L antibody. A specific 110 kDa band, identical size to the purified FILIP1L protein, was detected by anti-FILIP1L antibody, suggesting that HUVECs express a full length FILIP1L protein (FIG. 4). In addition, FILIP1L was expressed predominantly in the cytoplasm with less expression in the membrane and nucleus. Having demonstrated the expression of FILIP1L protein in cultured endothelial cells, the expression of FILIP1L in human tissue was then examined. Immunohistochemical analysis was performed on 15 frozen human colon cancers and matched normal colon tissues using anti-FILIP1L antibody. In normal colon, FILIP1L was expressed in the vasculature and muscularis mucosa. In colon cancer, FILIP1L was strongly expressed in tumor stroma and the vasculature. Thus, these data demonstrate that FILIP1L is expressed in vasculature and smooth muscle, and in desmoplastic stroma in response to tumor invasion. Endogenous FILIP1L protein in HUVECs was immunofluorescently stained with FILIP1L antibody, which showed a punctate distribution in the cytoplasm. Preincubation of FILIP1L antibody with FILIP1L protein, but not with BSA, abrogated the staining.

Upregulation of FILIP1L Protein by Endostatin

Figure 6A:
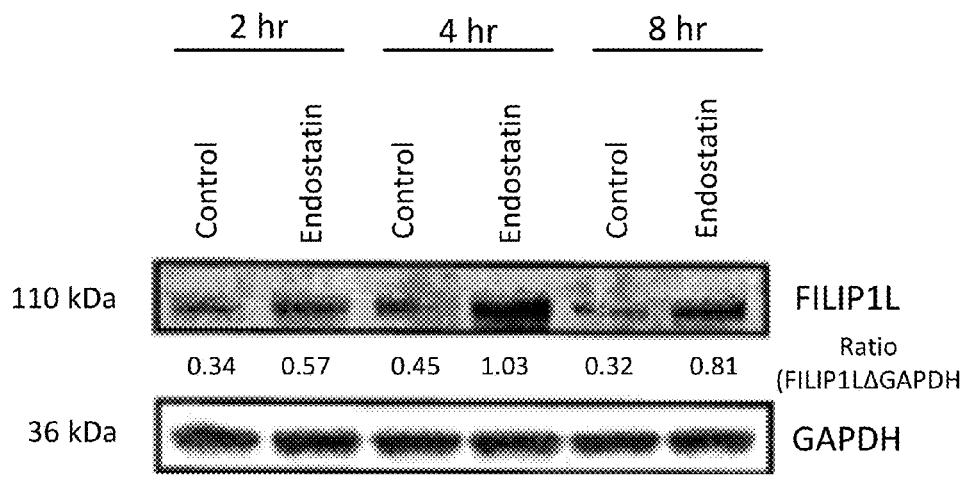
FIG. 6 shows the upregulation of FILIP1L protein by endostatin A, Increased expression of FILIP1L protein was detected in HUVECs treated with endostatin for 2, 4 and 8 h by western blot using anti-FILIP1L antibody. GAPDH blot is shown as the loading control. The numbers underneath the blot are the densitometric values calculated as FILIP1L-GAPDH ratios using ImageQuant software. The result is representative of two independent experiments. B, FILIP1L expression in endostatin-treated HUVECs was significantly more than that in vehicle-treated control cells (P=0.0012). Five images from each treatment group were analyzed. Axiovision 4.6 software (Zeiss) was used to quantify the percent area with FILIP1L-positive staining Box & whiskers plot (GraphPad Prism 3.0) is shown.
Figure 6B:
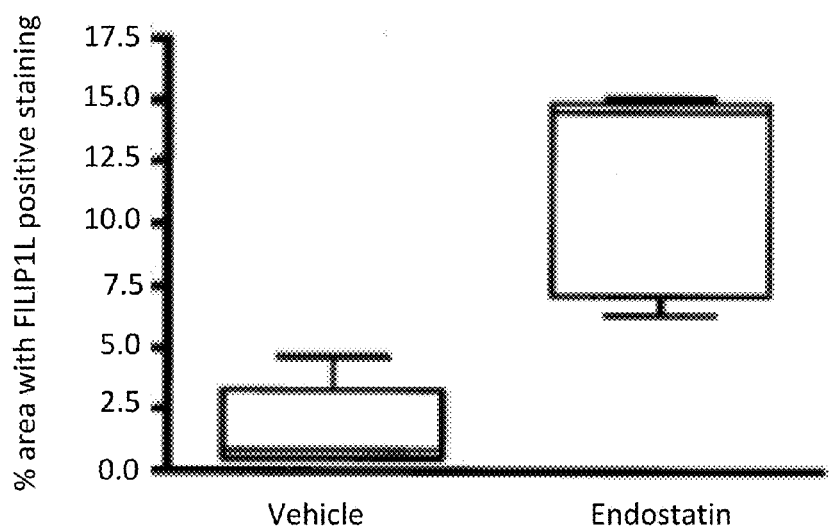

Previous studies have shown that FILIP1L mRNA expression is upregulated in HUVECs within 1 h following the treatment of endothelial cells with the angiogenesis inhibitors endostatin, fumagillin and EMAP II (Mazzanti C M et al. Genome Res 2004; 14:1585-93; Tandle AT et al. Cytokine 2005; 30:347-58). To further confirm that FILIP1L protein expression is upregulated in endothelial cells in response to angiogenesis inhibitors, HUVECs were treated with endostatin, harvested cells at 2, 4 and 8 h, and performed western blot analysis using anti-FILIP1L antibody on whole cell lysates. Compared to vehicle-treated controls, endostatin-treated HUVECs expressed more FILIP1L protein at all the time points tested (densitometric quantitation values are also shown in FIG. 6A). To examine if endostatin treatment affects cellular distribution of FILIP1L protein in endothelial cells, HUVECs were serum starved to synchronize them. We then treated those HUVECs with endostatin and immunofluorescently stained them with anti-FILIP1L antibody at 4 h. Serum-starved, vehicle-treated control cells demonstrated weak cytoplasmic staining, whereas endostatin-treated cells showed a stronger punctate distribution of staining in the cytoplasm. FILIP1L expression measured by immunofluorescent staining in endostatin-treated HUVECs was significantly more than that in vehicle-treated control cells ($P=0.0012$) (FIG. 6B). In addition, this staining was FILIP1L-specific as anti-FILIP1L antibody preincubated with FILIP1L protein, but not with BSA control, failed to demonstrate the staining. These results suggest that FILIP1L protein expression is increased following endostatin treatment and support our initial observations at the mRNA level. The punctate distribution in the cytoplasm was detected in HUVECs treated with endostatin for 4 h by immunofluorescent staining using anti-FILIP1L antibody. Vehicle-treated control cells showed diffused cytoplasmic staining Nuclear staining with DAPI is shown in blue. Scale bar shown indicates 10 μm. The result is a representative image from two independent experiments. Preincubation of anti-FILIP1L antibody with FILIP1L protein, but not with BSA, abrogated the punctuate staining seen in HUVECs treated with endostatin. Nuclear staining with DAPI is shown in blue. Scale bar shown indicates 20 μm.

Overexpression of FILIP1L in Endothelial Cells Leads to Inhibition of Cell Proliferation and an Increase in Apoptosis HUVECs were transfected with a plasmid encoding FILIP1L cDNA and measured cell proliferation by BrdU ELISA 24 h after transfection. Transfection efficiency was 50±10%, as verified by GFP expression following the transfection of HUVECs with a control plasmid encoding an eGFP. Compared to control empty vector-transfected cells, FILIP1L-transfected cells showed a decrease in cell proliferation ($P<0.0001$). To determine if overexpression of FILIP1L in endothelial cells results in an increase in apoptosis, caspase 3/7 activity was measured at 24 h following transfection of HUVECs with FILIP1L cDNA. Caspase 3/7 activity was measured by luminescence. Although caspase 3/7 activity in control vector-transfected cells was present due to the cytotoxicity caused by the transfection procedure, FILIP1L-transfected cells showed significantly more activity ($P<0.001$). To further detect apoptosis in these cells, the transfected cells were stained with annexin V-FITC and 7-AAD at 48 h following transfection, and measured staining using flow cytometry. FILIP1L overexpression resulted in increased staining of both annexin V-FITC and 7-AAD (44.4% vs. 15.2%), indicating that late stage apoptosis is increased in FILIP1L-transfected cells compared to control vector-transfected cells.

FILIP1L Truncation Mutants have Differential Antiproliferative Activity

Figure 7:
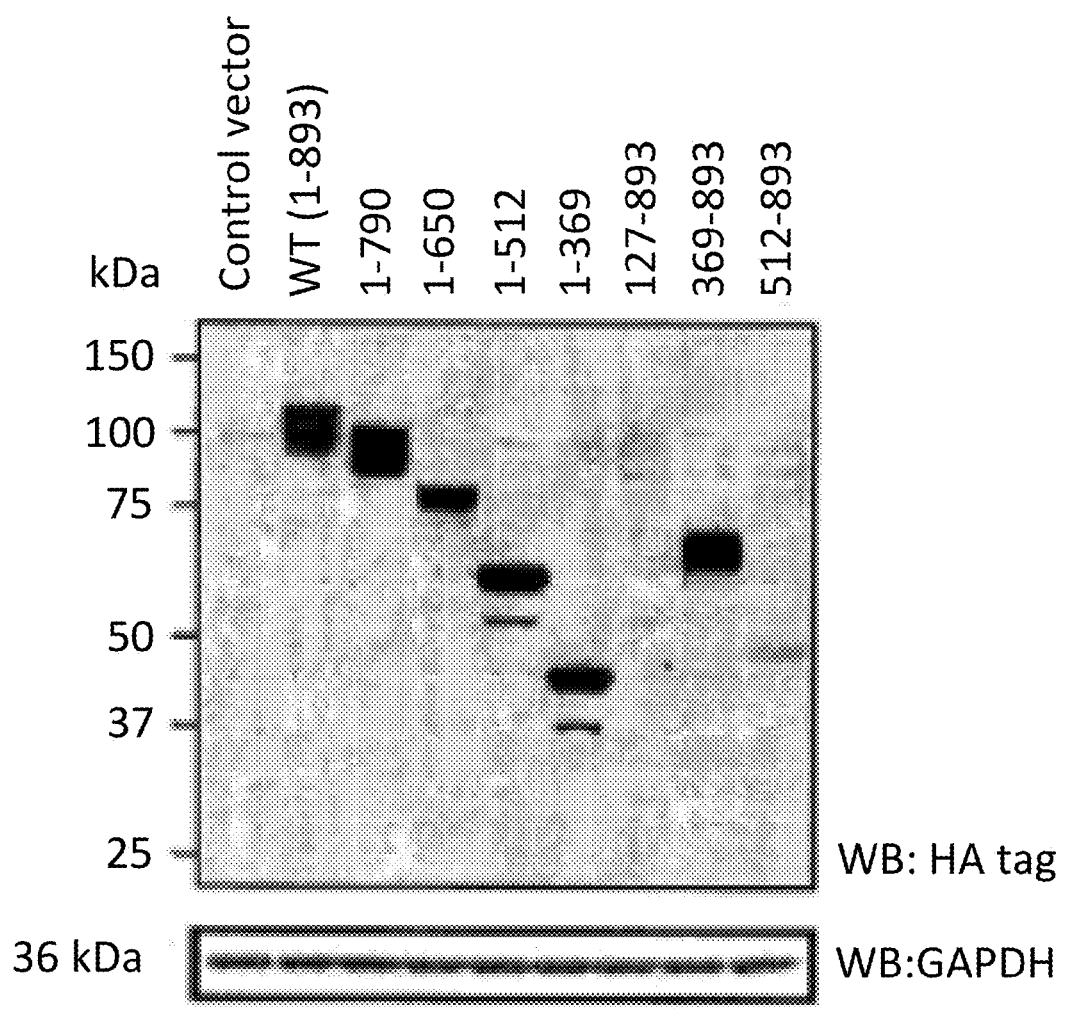
FIG. 7 shows that FILIP1L truncation mutants have differential antiproliferative activity. A, A schematic representation of FILIP1L protein (893 amino acids). Two leucine zipper motifs (black rectangles) and a prefoldin domain (striped rectangles) were recognized in the N-terminal half of a coiled-coil region (grey area). A SbcC (COG0419; ATPase involved in DNA repair) conserved domain in its N-terminal half and a Herpes_BLLF1 (pfam05109; Herpes virus major outer envelope glycoprotein) conserved domain in its C-terminal half are also shown. B, A schematic diagram of FILIP1L truncation mutants. HA indicates C-terminal HA tag. Amino acid residues are shown on top of each construct. C, Expression of each mutant was confirmed in HEK293 cells transfected with each construct by western blot analysis using anti-HA tag antibody. GAPDH blot is shown as the loading control.

A coiled-coil region (residues 3-542), two leucine zipper motifs (residues 83-111 and 218-253) and a prefoldin domain (residues 465-535) can be recognized in the N-terminal half of the FILIP1L protein. In addition, an NCBI conserved domain search 1 reveals that FILIP1L has a SbcC (COG0419; ATPase involved in DNA repair; residues 19-576) conserved domain in its N-terminal half and a Herpes_BLLF1 (pfam05109; Herpes virus major outer envelope glycoprotein; residues 640-829) conserved domain in its C-terminal half (FIG. 7A).

To examine which part of the FILIP1L protein mediates the antiproliferative activity in endothelial cells, a series of N-terminal and C-terminal truncation mutants of FILIP1L as a fusion protein containing a C-terminal HA tag (FIG. 7B) were generated. To determine if these mutant constructs produce proteins in cells, HEK293 cells were transfected with each construct and western blot analysis was performed using anti-HA tag antibody. All the constructs produced proteins of the predicted size, although N-terminal truncation mutants 127-893 and 512-893 showed low levels of expression (FIG. 7C). To determine if these proteins are functional, HUVECs were transfected with the plasmid encoding each FILIP1L mutant, and measured cell proliferation by BrdU ELISA 24 h after transfection. FILIP1L truncation mutants 1-790, 1-650, 1-512 and 127-893 significantly inhibited cell proliferation compared to control. C-terminal truncation mutant 1-790 was more potent in its ability to inhibit cell proliferation than wild-type ($P=0.001$) (FIG. 4). To examine if overexpression of FILIP1LΔC103 (amino acids 1-790) in endothelial cells results in an increase in apoptosis, we measured caspase 3/7 activity at 24 h following transfection of HUVECs with FILIP1LΔC103 cDNA. FILIP1LΔC103-transfected cells showed significantly more apoptotic activity than control cells ($P<0.0001$).

Overexpression of FILIP1LΔC103 in HUVECs as Well as DU145 Prostate Cancer Cells Leads to Inhibition of Cell Migration Since inhibition of cell migration is one of the important characteristics of angiogenesis inhibitors, it was tested whether overexpression of FILIP1LΔC103 results in inhibition of cell migration. To do this, HUVECs were transfected with a plasmid encoding FILIP1LΔC103 cDNA and cell migration was measured by Electric Cell-Substrate Impedance Sensing system (Applied Biophysics Inc. (Giaever I and Keese C R. Nature 1993; 366:591-2; Keese C R et al. Proc Natl Acad Sci USA 2004; 101:1554-9)). Compared to control empty vector-transfected cells, FILIP1LΔC103-transfected cells showed a significantly slower migration rate ($P<0.0001$) (FIG. 3), indicating that overexpression of FILIP1LΔC103 in HUVECs results in inhibition of cell migration.

The effects of overexpression of FILIP1L C103 on migration of neoplastic cell lines was also tested. DU145 prostate cancer cells were selected as a model system because FILIP1L mRNA expression was shown to be repressed in immortalized prostate epithelial cells (Schwarze S R et al. J Biol Chem 2002; 277:14877-83; Schwarze S R et al. Neoplasia 2005; 7:816-23), and FILIP1L mRNA expression is relatively low in this cell line compared to other cancer cell lines. Overexpression of FILIP1LΔC103 in DU145 cells also resulted in inhibition of cell proliferation. Thus, inducible FILIP1LΔC103-overexpressing clones were developed. The system used was the ViraPower™ T-REx™ Lentiviral Expression System (Invitrogen). In this system the expression of a gene of interest is repressed by a Tet repressor in the absence of tetracycline (or doxycycline), whereas it is derepressed in the presence of tetracycline (or doxycycline). Clones were screened by real time RT-PCR analysis. Several clones showed a 2.5-7 fold increase in FILIP1LΔC103 mRNA expression following doxycycline induction compared to the uninduced condition (FIG. 8A).

Figure 8A:
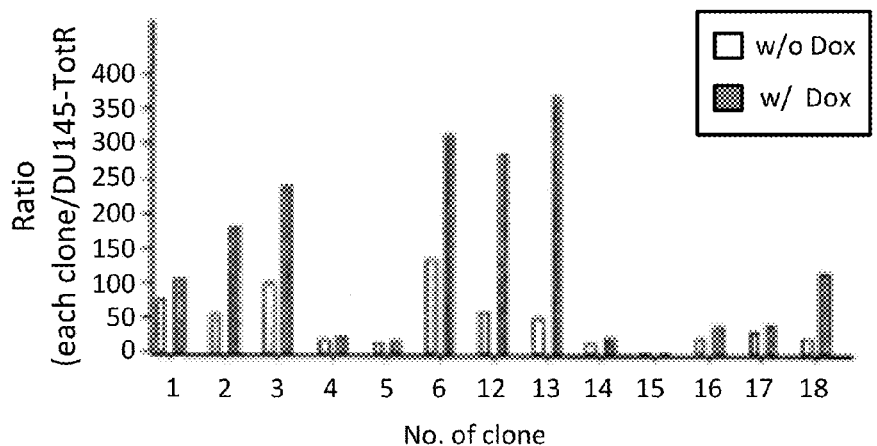
FIG. 8 shows that overexpression of FILIP1LΔC103 in HUVECs as well as DU145 prostate cancer cells leads to inhibition of cell migration. A, Real time RT-PCR analysis for FILIP1L on cDNA from DU145 clones transduced with FILIP1LΔC103-lentivirus. Each clone was treated with either PBS (w/o) or 1 μg/mL doxycycline (Dox) for 48 h prior to harvest. The y-axis represents a ratio between each clone and the parental Tet repressor-expressing DU145 cells where each value was standardized with housekeeping gene GAPDH. Each bar is an average of three experiments. B, A 90 kDa FILIP1LΔC103 protein was detected in Tet repressor-expressing DU145 cells transduced with FILIP1LΔC103-lentivirus, but not control lentivirus, by western blot using anti-FILIP1L antibody. The result shown is a representative (clone #12) from several clones. GAPDH blot is shown as the loading control. C, All three FILIP1LΔC103 clones, but not mixed population of control cells, showed a significantly slower migration in the presence of doxycycline. Error bars indicate SEM (n=3). P value comparison between in the presence and in the absence of doxycycline were: control cells (P=0.141), clone #2 (P=0.0014), clone #12 (P=0.0005) and clone #13 (P<0.0001). The result is representative of two independent experiments.
Figure 8B:
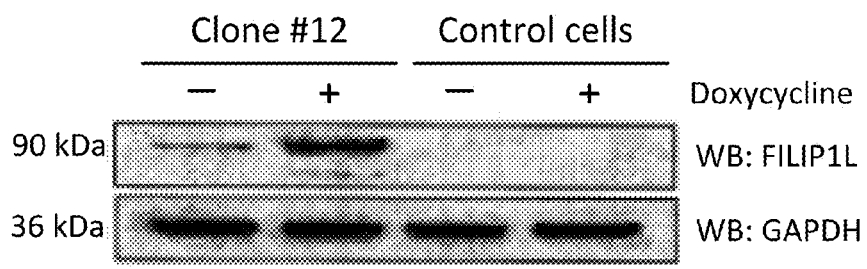
Figure 8C:
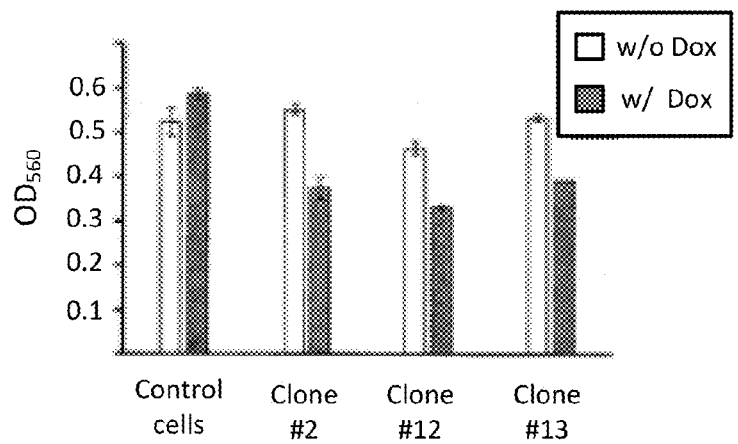

Unexpectedly, however, it was observed that, at the uninduced basal level, most of these clones expressed 20-60 fold more FILIP1LΔC103 mRNA than parental Tet repressor-expressing DU145 cells (FIG. 8A). FILIP1LΔC103 protein levels were shown to be increased considerably by doxycycline, but the basal level expression was also detectable in these clones (FIG. 8B). Control cells that were a mixed population from empty lentivirus-transduced Tet repressor-expressing DU145, however, did not produce any FILIP1LΔC103 protein (FIG. 8B). To measure cell migration for these cells, the Boyden chamber assay was utilized. Using this system, cell migration was measured for the FILIP1LΔC103 clones #2, 12 and 13 as well as control cells. All the FILIP1LΔC103 clones, but not control cells, showed a significantly slower migration in the presence of doxycycline ($P<0.005$) (FIG. 8C). Therefore, these data indicate that overexpression of FILIP1LΔC103 in DU145 cells also results in inhibition of cell migration.

Targeted Expression of FILIP1LΔC103 in Tumor Vasculature Results in Inhibition of Tumor Growth In Vivo It has been demonstrated that overexpression of FILIP1L results in inhibition of cell proliferation and migration, and increased apoptosis in vitro. The effects of targeted FILIP1L expression in vivo were then evaluated. In particular, it was chosen to selectively deliver FILIP1L to tumor vasculature in order to determine if overexpression of FILIP1L in tumor vasculature leads to an antitumor effect. To achieve this, a hybrid adeno-associated virus/phage (AAVP) vector was utilized, which has been shown to specifically target tumor vasculature in an RGD peptide-restricted manner (Hajitou A et al. Nat Protoc 2007; 2:523-31; Hajitou A et al. Cell 2006; 125:385-98; Soghomonyan S et al. Nat Protoc 2007; 2:416-23). These hybrid vectors rely on the specific binding relationship between an RGD peptide and $\alpha_v$ integrin expressed on the surface of tumor vasculature. These vectors have been shown to specifically traffic to, and specifically transfect, tumor associated endothelial cells without evidence of transfection of normal endothelial cells. Two FILIP1L mutants were tested for this purpose: FILIP1LΔC103 (amino acid 1-790) and FILIP1LΔC243 (amino acid 1-650). Each FILIP1L mutant cDNA was cloned into the AAVP vector, produced RGD-targeted AAVP and screened for the AAVP which showed the highest expression of each mutant by real time RT-PCR analysis.

In order to examine whether the AAVP specifically targets tumor vasculature in our M21 human melanoma model, the RGD-targeted AAVP was injected into the tail vein of female athymic nude mice harboring a 100-150 mm3 subcutaneous M21 tumor. After injection, tumors were harvested by timecourse, and analyzed by immunofluorescent staining with anti-CD31 and anti-AAVP antibodies. Both RGD-4C-FILIP1LΔC103 AAVP (AAVP expressing FILIP1L mutant 1-790; referred to as AAVP-ΔC 103) and RGD-4C-FILIP1LΔC243 AAVP (AAVP expressing FILIP1L mutant 1-650; here-after referred to as AAVP-ΔC243) were shown to specifically target tumor vasculature, but not tumor cells (FIG. 10A) or the vasculature of normal organs. FILIP1L protein expression was also measured in these tumors by western blot analysis using anti-FILIP1L antibody on whole tumor lysates. Tumors from AAVP-ΔC103-treated mice, but not PBS- and RGD-4C AAVP (control null AAVP; referred to as AAVP-null)-treated mice, showed FILIP1L protein expression. Therefore, these data are consistent with the observation that the FILIP1L mutant is expressed in the tumor vasculature of mice treated with AAVP-ΔC 103. AAVP-ΔC 103 injected intravenously specifically targeted tumor vasculature. Tumors from PBS- and AAVP-ΔC103-treated mice were immunofluorescently stained with anti-AAVP antibody followed by Alexa Fluor 594 anti-rabbit IgG (red for the AAVP staining) and anti-CD31 (also known as platelet endothelial cell adhesion molecule) antibody followed by Alexa Fluor 488 anti-rat IgG (green for the blood vessel staining) Nuclear staining with DAPI is shown in blue. Scale bar shown indicates 50 µm. The result is a representative image from two independent experiments. Similar data were obtained using AAVP-ΔC243. A 90 kDa FILIP1LΔC103 protein was detected in whole tumor lysates from AAVP-ΔC 103-treated mice, but not PBS- and AAVP-null-treated mice, by western blot using anti-FILIP1L antibody. Three different tumors per group were analyzed. GAPDH blot is shown as the loading control. Representative images of CD31-stained tumors from PBS-, AAVP-null- and AAVP-ΔC103-treated mice are shown. Tumors treated with each AAVP for 4 days were immunofluorescently stained with anti-CD31 antibody followed by Alexa Fluor 488 anti-rat IgG (green for the vessel staining) Nuclear staining with DAPI is shown in blue. Scale bar shown indicates 100 µm. Vessel density was significantly decreased in tumors from AAVP-ΔC103-treated mice compared to those from AAVP-null-treated mice ($P<0.01$) and PBS-treated mice ($P<0.001$) at day 4. The percentage of cells in the tumors stained positive for CD31 was quantified using Axiovision 4.6 software (Zeiss). Box & whiskers plot (GraphPad Prism 3.0) of vessel density is shown. Middle lines indicate median values. *, $P<0.01$; , $P<0.001$; *, $P<0.05$; n=3 mice per treatment group.

To evaluate the efficacy of the FILIP1L mutant-AAVP treatment on tumor growth inhibition in vivo, M21 melanoma cells were injected subcutaneously into female athymic nude mice, and grown to an average size of 100 mm3. Mice were randomly sorted into four groups (n=11 for each group), AAVP ($1 \times 10^{11}$ transducing units per dose) was injected intravenously at day 0 and day 7, and tumors were measured in a blinded manner. The following groups were tested: PBS, AAVP-null, AAVP-ΔC243 and AAVP-ΔC103. PBS control tumors grew aggressively and started to show central necrosis by day 14. Thus, the experiments were terminated at day 14. Only tumors from AAVP-ΔC103-treated mice were significantly smaller than those from PBS-treated mice by day 14 ($P<0.01$) (FIG. 9). Although tumors from AAVP-null-treated mice and AAVP-ΔC243-treated mice were smaller than those from PBS-treated mice, the differences were not statistically significant. In addition, tumors from AAVP-ΔC103-treated mice were significantly smaller than those from AAVP-null-treated mice ($P<0.05$) and AAVP-ΔC243-treated mice ($P<0.05$) by day 14 (FIG. 9). These results indicate that targeted expression of FILIP1LΔC 103 in tumor vasculature results in inhibition of M21 melanoma growth in vivo.

In order to confirm that the inhibition of tumor growth is dependent on the antivascular effects of FILIP1LΔC103, vessel density was analyzed for these AAVP-treated tumors. The percentage area of CD31 positive cells was used as a measure of vessel density (Blansfield J A et al. Clin Cancer Res 2008; 14:270-80). Vessel density from AAVP-ΔC103-treated tumors was significantly less than those from PBS-treated tumors ($P<0.001$) and AAVP-null-treated tumors ($P<0.01$) at day 4, indicating that the inhibition of tumor vasculature by AAVP-ΔC103 leads to the inhibition of M21 tumor growth. In addition, AAVP-ΔC 103-treated tumors showed extensive apoptosis as measured by TUNEL staining compared to PBS- or AAVP-null-treated tumors, further indicating that the inhibition of tumor vasculature by AAVP-ΔC 103 results in induction of apoptosis and necrosis in these M21 tumors.

H. Sequences

```
DOC1 Isoform 2 (SEQ ID NO: 1; GenBank Accession No. NP_055705.2 (893 aa)):
mvvdeqqrlt aqltlqrqki qelttnaket htklalaear vqeeeqkatr lekelqtqtt kfhqdqdtim akltnedsqn rqlqqklaal srgideleet nrslrkaeee lqdikekisk geygnagima eveelrkrvl dmegkdeeli kmeeqcrdln krleretlqs kdfklevekl skrimalekl edafnkskqe cyslkcnlek ermttkqlsq eleslkvrik eleaiesrle kteftlkedl tklktltvmf vderktmsek lkktedklqa assqlqveqn kvttvtekli eetkralksk tdveekmysv tkerddlknk lkaeeekgnd llsrvnmlkn rlqsleaiek dflknklnqd sgksttalhq ennkikelsq everlklklk dmkaieddlm ktedeyetle rryanerdka qflskelehv kmelakykla ektetsheqw lfkrlqeeea ksghlsrevd alkekiheym atedlichlq gdhsvlqkkl nqqenrnrdl greienltke leryrhfsks lrpslngrri sdpqvfskev qteavdnepp dykslipler avingqlyee senqdedpnd egsvlsfkcs qstpcpvnrk lwipwmkske ghlqngkmqt kpnanfvqpg dlvlshtpgq plhikvtpdh vqntatleit spttesphsy tstavipncg tpkqritilq nasitpvksk tstedlmnle qgmspitmat faraqtpesc gsltpertms piqvlavtgs asspeqgrsp epteisakha ifrvspdrqs swqfqrsnsn sssvittedn kihihlgspy mqavaspvrp aspsaplqdn rtqglingal nkttnkvtss ititptatpl prqsqitvsn iyn DOC1 variant 2 (GenBank Accession No. NP_055705; SEQ ID NO: 2 (752 aa))
mvvdeqqrlt aqltlqrqki qelttnaket htklalaear vqeeeqkatr lekelqtqtt kfhqdqdtim akltnedsqn rqlqqklaal srgideleet nrslrkaeee lqdikekisk geygnagima eveelikmee qcrdlnkrle retlqskdfk leveklskri maleklеdaf nkskqecysl kcnlekermt tkqlsqeles lkvrikelea iesrlektef tlkedltklk tltvmfvder ktmseklkkt edklqaassq lqveqnkvtt vteklieetk ralksktdve ekmysvtker ddlknklkae eekgndllsr vnmlknrlqs leaiekdflk nklnqdsgks ttalhqennk ikelsqever lklklkdmka ieddlmkted eyetlerrya nerdkaqfls kelehvkmel akyklaekte tsheqwlfkr lqeeeaksgh lsrevdalke kiheymated lichlqgdhs vckkklnqqe nrnrdlgrei enltkelery rhfskslrps lngrrisdpq vfskevqtea vdneppdyks lipleravin gqlyeesenq dedpndegsv lsfkcsqstp cpvnrklwip wmkskeghlq ngkmqtkpna nfvqpgdlvl shtpgqplhi kvtpdhvqnt atleitsptt esphsytsta vipncgtpkq ritilqnasi tpvksktste dlmnleqgms pitmatfara qtpescgslt pertmslfrf wl DOC1 Isoform 1 (GenBank Accession No. NP_878913.2; SEQ ID NO: 3 (1135 aa))
mrsrgsdteg saqkkfprht kghsfqgpkn mkhrqqdkds psesdvilpc pkaekphsgn ghqaedlsrd dllfllsile gelqardevi gilkaekmdl alleaqygfv tpkkvlealq rdafqakstp wqediyekpm neldkvvekh kesyrrilgq llvaeksrrq tileleeekr khkeymeksd eficlleqec erlkklidqe iksqeekeqe kekrvttlke eltklksfal mvvdeqqrlt aqltlqrqki qelttnaket htklalaear vqeeeqkatr lekelqtqtt kfhqdqdtim akltnedsqn rqlqqklaal srqideleet nrslrkaeee lqdikekisk geygnagima eveelrkrvl dmegkdeeli kmeeqcrdln krleretlqs kdfklevekl
```

-continued

```
skrimalekl edafnkskqe cyslkcnlek ermttkqlsq eleslkvrik eleaiesrle kteftlkedl tklktltvmf vderktmsek lkktedklqa assqlqveqn kvttvtekli eetkralksk tdveekmysv tkerddlknk lkaeeekgnd llsrvnmlkn rlqsleaiek dflknklnqd sgksttalhq ennkikelsq everlklklk dmkaieddlm ktedeyetle rryanerdka qflskelehv kmelakykla ektetsheqw lfkrlqeeea ksghlsrevd alkekiheym atedlichlq gdhsvlqkkl nqqenrnrdl greienltke leryrhfsks lrpslngrri sdpqvfskev qteavdnepp dykslipler avingqlyee senqdedpnd egsvlsfkcs qstpcpvnrk lwipwmkske ghlqngkmqt kpnanfvqpg dlvlshtpgq plhikvtpdh vqntatleit spttesphsy tstavipncg tpkqritilq nasitpvksk tstedlmnle qgmspitmat faraqtpesc gsltpertms piqvlavtgs asspeqgrsp epteisakha ifrvspdrqs swqfqrsnsn sssvittedn kihihlgspy mqavaspvrp aspsaplqdn rtqglingal nkttnkvtss ititptatpl prqsqitvep lllph
```

DOC1 Isoform 3 (GenBank Accession No. NP_001035924.1; SEQ ID NO: 4 (1133 aa))
```
mrsrgsdteg saqkkfprht kghsfqgpkn mkhrqqdkds psesdvilpc pkaekphsgn ghqaedlsrd dllfllsile gelqardevi gilkaekmdl alleaqygfv tpkkvlealq rdafqakstp wqediyekpm neldkvvekh kesyrrilgq llvaeksrrq tileleeekr khkeymeksd eficlleqec erlkklidqe iksqeekeqe kekrvttlke eltklksfal mvvdeqqrlt aqltlqrqki qelttnaket htklalaear vqeeeqkatr lekelqtqtt kfhqdqdtim akltnedsqn rqlqqklaal srqideleet nrslrkaeee lqdikekisk geygnagima eveelrkrvl dmegkdeeli kmeeqcrdln krleretlqs kdfkleveki skrimalekl edafnkskqe cyslkcnlek ermttkqlsq eleslkvrik eleaiesrle kteftlkedl tklktltvmf vderktmsek lkktedklqa assqlqveqn kvttvtekli eetkralksk tdveekmysv tkerddlknk lkaeeekgnd llsrvnmlkn rlqsleaiek dflknklnqd sgksttalhq ennkikelsq everlklklk dmkaieddlm ktedeyetle rryanerdka qflskelehv kmelakykla ektetsheqw lfkrlqeeea ksghlsrevd alkekiheym atedlichlq gdhsvlqkkl nqqenrnrdl greienltke leryrhfsks lrpslngrri sdpqvfskev qteavdnepp dykslipler avingqlyee senqdedpnd egsvlsfkcs qstpcpvnrk lwipwmkske ghlqngkmqt kpnanfvqpg dlvlshtpgq plhikvtpdh vqntatleit spttesphsy tstavipncg tpkqritilq nasitpvksk tstedlmnle qgmspitmat faraqtpesc gsltpertms piqvlavtgs asspeqgrsp epteisakha ifrvspdrqs swqfqrsnsn sssvittedn kihihlgspy mqavaspvrp aspsaplqdn rtqglingal nkttnkvtss ititptatpl prqsqitvep iyn

SEQ ID NO: 5:
AGCGTAACCAAGGAGAGAGAT

SEQ ID NO: 6
ATTCATTCATTCATTCACCAT

SEQ ID NO: 7
   1 ataggccggg cgcgctcagc gccccgctcg cattgttcgg gcgactctcg gagcgcgcac 61 agtcggctcg cagcgcggca ctacagcggc cccggcccgg ccccgcccg gccccggcgc 121 aggcagttca gattaaagaa gctaattgat caagaaatca gtctcagga ggagaaggag 181 caagaaaagg agaaaagggt caccaccctg aaagaggagc tgaccaagct gaagtctttt 241 gctttgatgg tggtggatga acagcaaagg ctgacggcac agctcaccct tcaaagacag 301 aaaatccaag agctgaccac aaatgcaaag gaaacacata ccaaactagc ccttgctgaa
```

-continued

```
 361 gccagagttc aggaggaaga gcagaaggca accagactag agaaggaact gcaaacgcag
 421 accacaaagt ttcaccaaga ccaagacaca attatggcga agctcaccaa tgaggacagt
 481 caaaatcgcc agcttcaaca aaagctggca gcactcagcc ggcagattga tgagttagaa
 541 gagacaaaca ggtctttacg aaaagcagaa gaggagctgc aagatataaa agaaaaaatc
 601 agtaagggag aatatggaaa cgctggtatc atggctgaag tggaagagct caggaaacgt
 661 gtgctagata tggaagggaa agatgaagag ctcataaaaa tggaggagca gtgcagagat
 721 ctcaataaga ggcttgaaag ggagacgtta cagagtaaag actttaaact agaggttgaa
 781 aaactcagta aagaattat ggctctggaa agttagaag acgctttcaa caaaagcaaa
 841 caagaatgct actctctgaa atgcaattta gaaaagaaa ggatgaccac aaagcagttg
 901 tctcaagaac tggagagttt aaaagtaagg atcaaagagc tagaagccat gaaagtcgg
 961 ctagaaaaga cagaattcac tctaaaagag gatttaacta aactgaaaac attaactgtg
1021 atgtttgtag atgaacggaa acaatgagt gaaaaattaa agaaaactga agataaatta
1081 caagctgctt cttctcagct tcaagtggag caaaataaag taacaacagt tactgagaag
1141 ttaattgagg aaactaaaag ggcgctcaag tccaaaaccg atgtagaaga aaagatgtac
1201 agcgtaacca aggagagaga tgatttaaaa aacaaattga agcggaaga agagaaagga
1261 aatgatctcc tgtcaagagt taatatgttg aaaaatagg ttcaatcatt ggaagcaatt
1321 gagaaagatt tcctaaaaaa caaattaaat caagactctg ggaaatccac aacagcatta
1381 caccaagaaa acaataagat taaggagctc tctcaagaag tggaaagact gaaactgaag
1441 ctaaaggaca tgaaagccat tgaggatgac ctcatgaaaa cagaagatga atatgagact
1501 ctagaacgaa ggtatgctaa tgaacgagac aaagctcaat ttttatctaa agagctagaa
1561 catgttaaaa tggaacttgc taagtacaag ttagcagaaa agacagagac cagccatgaa
1621 caatggcttt tcaaaaggct tcaagaagaa gaagctaagt cagggcacct ctcaagagaa
1681 gtggatgcat taaaagagaa aattcatgaa tacatggcaa ctgaagacct aatatgtcac
1741 ctccagggag atcactcagt cctgcaaaaa aaactaaatc aacaagaaaa caggaacaga
1801 gatttaggaa gagagattga aaacctcact aaggagttag agaggtaccg gcatttcagt
1861 aagagcctca ggcctagtct caatggaaga agaatttccg atcctcaagt attttctaaa
1921 gaagttcaga cagaagcagt agacaatgaa ccacctgatt acaagagcct cattcctctg
1981 gaacgtgcag tcatcaatgg tcagttatat gaggagagtg agaatcaaga cgaggaccct
2041 aatgatgagg atctgtgct gtccttcaaa tgcagccagt ctactccatg tcctgttaac
2101 agaaagctat ggattccctg gatgaaatcc aaggagggcc atcttcagaa tggaaaaatg
2161 caaactaaac ccaatgccaa ctttgtgcaa cctggagatc tagtcctaag ccacacacct
2221 gggcagccac ttcatataaa ggttactcca gaccatgtac aaaacacagc cactcttgaa
2281 atcacaagtc caaccacaga gagtcctcac tcttacacga gtactgcagt gataccgaac
2341 tgtggcacgc caaagcaaag gataaccatc ctccaaaacg cctccataac accagtaaag
2401 tccaaaacct ctaccgaaga cctcatgaat ttagaacaag gcatgtcccc aattaccatg
2461 gcaacctttg ccagagcaca gaccccagag tcttgtggtt ctctaactcc agaaaggaca
2521 atgtccccta ttcaggtttt ggctgtgact ggttcagcta gctctcctga gcagggacgc
2581 tccccagaac caacagaaat cagtgccaag catgcgatat tcagagtctc cccagaccgg
2641 cagtcatcat ggcagtttca gcgttcaaac agcaatagct caagtgtgat aactactgag
2701 gataataaaa tccacattca cttaggaagt ccttacatgc aagctgtagc cagccctgtg
```

-continued

```
2761 agacctgcca gcccttcagc accactgcag gataaccgaa ctcaaggctt aattaacggg 2821 gcactaaaca aaacaaccaa taaagtcacc agcagtatta ctatcacacc aacagccaca 2881 cctcttcctc gacaatcaca aattacagta agtaatatat ataactgacc acgctcaccc 2941 tcatccagtc catactgata tttttgcaag gaactcaatc ctttttttaat catccctcca 3001 tatcccccaa gactgactga actcgtactt tgggaaggtt tgtgcatgaa ctatacaaga 3061 gtatctgaaa ctaactgttg cctgcatagt catatcgagt gtgcacttac tgtatatctt 3121 ttcatttaca tacttgtatg gaaaatattt agtctgcact tgtataaata catctttatg 3181 tatttcattt tccataactc actttaattt gactgcaact tgtcttggtg aaatacttta 3241 acattataaa acagtaaata atttgttatt ttta
```

SEQ ID NO: 8
mvvdeqqrlt aqltlqrqkv qelttnaket htklalaear vqeeeqkatr lekelqtqtt kfhqdqdtim akltnedsqn rqlqqklaal srqideleet nrslrkaeee lqdikekisk geygnagima eveelrkrvl dmegkdeeli kmeeqcrdln krleretlqs kdfkleveki skrimalekl edafnkskqe cyslkcnlek ermttkqlsq eleslkvrik eleaiesrle kteftlkedl tklktltvmf vderktmsek lkktedklqa assqlqveqn kvttvtekli eetkralksk tdveekmysv tkerddlknk lkaeeekgnd llsrvnmlkn rlqsleaiek dflknklnqd sgksttalhq ennkikelsq everlklklk dmkaieddlm ktedeyetle rryanerdka qflskelehv kmelakykla ektetsheqw lfkrlqeeea ksghlsrevd alkekiheym atedlichlq gdhsvlqkkl nqqenrnrdl greienltke leryrhfsks lrpslngrri sdpqvfskev qteavdnepp dykslipler avingqlyee senqdedpnd egsvlsfkcs qstpcpvnrk lwipwmkske ghlqngkmqt kpnanfvqpg dlvlshtpgq plhikvtpdh vqntatleit spttesphsy tstavipncg tpkqritilq nasitpvksk tstedlmnle qgmspitmat faraqtpesc gsltpertms piqvlavtgs asspeqgrsp epteisakha ifrvspdrqs swqfqrsnsn sssvittedn kihihlgspy mqavaspvrp aspsaplqdn rtqglingal nkttnkvtss ititptatpl prqsgitvsn iyn

SEQ ID NO: 9
AACGCTGGTATCATGGCTGAA

SEQ ID NO: 10
ATCTCTGCACTGCTCCTCCATT

SEQ ID NO: 11
TCACCAGGGCTGCTTTTAACTC

SEQ ID NO: 12
GGAATCATATTGGAACATGTAAACCA

Information for DOC1 (FILIP1L) Amino Acid and Gene:

```
LOCUS       NM_014890 3274 bp mRNA linear PRI 03-SEP-2007
DEFINITION  Homo sapiens filamin A interacting protein 1-like (FILIP1L),
            transcript variant 2, mRNA.
ACCESSION   NM_014890
VERSION     NM_014890.2 GI: 109659848
KEYWORDS    .
SOURCE      Homo sapiens (human)
ORGANISM    Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.
REFERENCE   1 (bases 1 to 3274)
AUTHORS     Tandle, A.T., Mazzanti, C., Alexander, H.R., Roberts, D.D. and
            Libutti, S.K.
```

```
-continued
TITLE        Endothelial monocyte activating polypeptide-II induced gene
             expression changes in endothelial cells
JOURNAL      Cytokine 30 (6), 347-358 (2005)
PUBMED       15935955
REMARK       GeneRIF: DOC1 might play a role in mediating some of the effects of
             EMAP-II on endothelial cells
REFERENCE    2 (bases 1 to 3274)
AUTHORS      Suzuki, Y., Yamashita, R., Shirota, M., Sakakibara, Y., Chiba, J.,
             Mizushima-Sugano, J., Nakai, K. and Sugano, S.
TITLE        Sequence comparison of human and mouse genes reveals a homologous
             block structure in the promoter regions
JOURNAL      Genome Res. 14 (9), 1711-1718 (2004)
PUBMED       15342556
REFERENCE    3 (bases 1 to 3274)
AUTHORS      Mok, S.C., Wong, K.K., Chan, R.K., Lau, C.C., Tsao, S.W., Knapp, R.C. and
             Berkowitz, R.S.
TITLE        Molecular cloning of differentially expressed genes in human
             epithelial ovarian cancer
JOURNAL      Gynecol. Oncol. 52 (2), 247-252 (1994)
PUBMED       8314147
COMMENT      VALIDATED REFSEQ: This record has undergone preliminary review
of the sequence, but has not yet been subject to final review. The
reference sequence was derived from BP233250.1 and BC027860.1.
On Jun. 27, 2006 this sequence version replaced gi: 7657036.
COMPLETENESS: complete on the 3' end.
PRIMARY      REFSEQ_SPAN          PRIMARY_IDENTIFIER   PRIMARY_SPAN      COMP
             1-583                BP233250.1           1-583
             584-3274             BC027860.1           516-3206
FEATURES             Location/Qualifiers
     source          1 . . . 3274
                     /organism="Homo sapiens"
                     /mol_type="mRNA"
                     /db_xref="taxon: 9606"
                     /chromosome="3"
                     /map="3q12.1"
     gene            1 . . . 3274
                     gene="FILIP1L"
                     /note="filamin A interacting protein 1-like; synonyms:
                         DOC1, DOC-1, GIP90"
                     /db_xref="GeneID: 11259"
                     /db_xref="HGNC: 24589"
                     /db_xref="HPRD: 16832"
     exon            1 . . . 131
                     /gene="FILIP1L"
                     /note="alignment: Splign"
                     /number=5
     exon            132 . . . 3274
                     /gene="FILIP1L"
                     /note="alignment: Splign"
                     /number=6b
     CDS             247 . . . 2928
                     /gene="FILIP1L"
                     /GO_component="myosin"
                     /note="isoform 2 is encoded by transcript variant 2"
                     /codon_start=1
                     /product="downregulated in ovarian cancer 1 isoform 2"
                     /protein_id="NP_055705.2"
                     /db_xref="GI: 109659849"
                     /db_xref="GeneID: 11259"
                     /db_xref="HGNC: 24589"
                     /db_xref="HPRD: 16832"
                     /translation=
                                                              (SEQ ID NO: 1)
MVVDEQQRLTAQLTLQRQKIQELTTNAKETHTKLALAEARVQEE
EQKATRLEKELQTQTTKFHQDQDTIMAKLTNEDSQNRQLQQKLAALSRQIDELEETNR
SLRKAEEELQDIKEKISKGEYGNAGIMAEVEELRKRVLDMEGKDEELIKMEEQCRDLN
KRLERETLQSKDFKLEVEKLSKRIMALEKLEDAFNKSKQECYSLKCNLEKERMTTKQL
SQELESLKVRIKELEAIESRLEKTEFTLKEDLTKLKTLTVMFVDERKTMSEKLKKTED
KLQAASSQLQVEQNKVTTVTEKLIEETKRALKSKTDVEEKMYSVTKERDDLKNKLKAE
EEKGNDLLSRVNMLKNRLQSLEAIEKDFLKNKLNQDSGKSTTALHQENNKIKELSQEV
ERLKLKLKDMKAIEDDLMKTEDEYETLERRYANERDKAQFLSKELEHVKMELAKYKLA
EKTETSHEQWLFKRLQEEEAKSGHLSREVDALKEKIHEYMATEDLICHLQGDHSVLQK
KLNQQENRNRDLGREIENLTKELERYRHFSKSLRPSLNGRRISDPQVFSKEVQTEAVD
NEPPDYKSLIPLERAVINGQLYEESENQDEDPNDEGSVLSFKCSQSTPCPVNRKLWIP
WMKSKEGHLQNGKMQTKPNANFVQPGDLVLSHTPGQPLHIKVTPDHVQNTATLEITSP
TTESPHSYTSTAVIPNCGTPKQRITILQNASITPVKSKTSTEDLMNLEQGMSPITMAT
FARAQTPESCGSLTPERTMSPIQVLAVTGSASSPEQGRSPEPTEISAKHAIFRVSPDR
QSSWQFQRSNSNSSSVITTEDNKIHIHLGSPYMQAVASPVRPASPSAPLQDNRTQGLI
```

NGALNKTTNKVTSSITITPTATPLPRQSQITVSNIYN

```
     STS        2535..2674
                /gene="FILIP1L"
                /standard_name="RH16583"
                /db_xref="UniSTS: 72547"
     STS        2669..2798
                /gene="FILIP1L"
                /standard_name="SHGC-33580"
                /db_xref="UniSTS: 171033"
     STS        2822..3237
                /gene="FILIP1L"
                /standard_name="DOC1_9246"
                /db_xref="UniSTS: 468384"
```

(SEQ ID NO: 7)

```
   1 ataggccggg cgcgctcagc gccccgctcg cattgttcgg gcgactctcg gagcgcgcac
  61 agtcggctcg cagcgcggca ctacagcggc cccggcccgg ccccgcccg gccccggcgc
 121 aggcagttca gattaaagaa gctaattgat caagaaatca agtctcagga ggagaaggag
 181 caagaaaagg agaaaagggt caccaccctg aaagaggagc tgaccaagct gaagtctttt
 241 gctttgatgg tggtggatga acagcaaagg ctgacggcac agctcaccct tcaaagacag
 301 aaaatccaag agctgaccac aaatgcaaag gaaacacata ccaaactagc ccttgctgaa
 361 gccagagttc aggaggaaga gcagaaggca accagactag agaaggaact gcaaacgcag
 421 accacaaagt tcaccaagaa ccaagacaca attatggcga agctcaccaa tgaggacagt
 481 caaaatcgcc agcttcaaca aaagctggca gcactcagcc ggcagattga tgagttagaa
 541 gagacaaaca ggtctttacg aaaagcagaa gaggagctgc aagatataaa agaaaaaatc
 601 agtaagggag aatatggaaa cgctggtatc atggctgaag tggaagagct caggaaacgt
 661 gtgctagata tggaagggaa agatgaagag ctcataaaaa tggaggagca gtgcagagat
 721 ctcaataaga ggcttgaaag ggagacgtta cagagtaaag actttaaact agaggttgaa
 781 aaactcagta aaagaattat ggctctgaaa aagttagaag acgcttttcaa caaaagcaaa
 841 caagaatgct actctctgaa atgcaattta gaaaagaaa ggatgaccac aaagcagttg
 901 tctcaagaac tggagagttt aaaagtaagg atcaaagagc tagaagccat tgaaagtcgg
 961 ctagaaaaga cagaattcac tctaaaagag gatttaacta aactgaaaac attaactgtg
1021 atgtttgtag atgaacggaa aacaatgagt gaaaaattaa agaaaactga agataaatta
1081 caagctgctt cttctcagct tcaagtggag caaataaaag taacaacagt tactgagaag
1141 ttaattgagg aaactaaaag ggcgctcaag tccaaaaccg atgtagaaga aaagatgtac
1201 agcgtaacca aggagagaga tgatttaaaa aacaaattga agcggaaga agagaaagga
1261 aatgatctcc tgtcaagagt taatatgttg aaaaatagge ttcaatcatt ggaagcaatt
1321 gagaaagatt tcctaaaaaa caattaaat caagactctg ggaaatccac aacagcatta
1381 caccaagaaa acaataagat taaggagctc tctcaagaag tggaaagact gaaactgaag
1441 ctaaaggaca tgaaagccat tgaggatgac ctcatgaaaa cagaagatga atatgagact
1501 ctagaacgaa ggtatgctaa tgaacgagac aaagctcaat tttatctaa agagctagaa
1561 catgttaaaa tggaacttgc taagtacaag ttagcagaaa agacagagac cagccatga
1621 caatggcttt tcaaaaggct tcaagaagaa gaagctaagt cagggcacct ctcaagagaa
1681 gtggatgcat taaaagagaa aattcatgaa tacatggcaa ctgaagacct aatatgtcac
1741 ctccaggag atcactcagt cctgcaaaaa aaactaaatc aacaagaaaa caggaacaga
1801 gatttaggaa gagagattga aaacctcact aaggagttag agaggtaccg gcatttcagt
1861 aagagcctca ggcctagtct caatggaaga agaatttccg atcctcaagt attttctaaa
1921 gaagttcaga cagaagcagt agacaatgaa ccacctgatt acaagagcct cattcctctg
1981 gaacgtgcag tcatcaatgg tcagttatat gaggagagtg agaatcaaga cgaggaccct
2041 aatgatgagg gatctgtgct gtccttcaaa tgcagccagt ctactccatg tcctgttaac
2101 agaaagctat ggattccctg gatgaaatcc aaggagggcc atcttcagaa tggaaaaatg
2161 caaactaaac ccaatgccaa ctttgtgcaa cctggagatc tagtcctaag ccacacacct
2221 gggcagccac ttcatataaa ggttactcca gaccatgtac aaaacacagc cactcttgaa
2281 atcacaagtc caaccacaga gagtcctcac tcttacacga gtactgcagt gataccgaac
2341 tgtggcacgc caaagcaaag gataaccatc ctccaaaacg cctccataac accagtaaag
2401 tccaaaacct ctaccgaaga cctcatgaat ttagaacaag gcatgtcccc aattaccatg
2461 gcaacctttg ccagagcaca gaccccagag tcttgtggtt ctctaactcc agaaaggaca
2521 atgtcccta ttcaggtttt ggctgtgact ggttcagcta gctctcctga gcagggacgc
2581 tccccagaac caacagaaat cagtgccaag catgcgatat tcagagtctc cccagaccgg
2641 cagtcatcat ggcagtttca gcgttcaaac agcaatagct caagtgtgat aactactgag
2701 gataataaaa tccacattca cttaggaagt ccttacatgc aagctgtagc cagccctgtg
2761 agacctgcca gcccttcagc accactgcag gataaccgaa ctcaaggctt aattaacggg
2821 gcactaaaca aaacaaccaa taagtcacc agcagtatta ctatcacacc aacagccaca
2881 cctcttcctc gacaatcaca aattacagta agtaatatat ataactgacc acgctcaccc
2941 tcatccagtc catactgata ttttgcaag gaactcaatc ctttttaat catccctcca
3001 tatcccccaa gactgactga actcgtactt tgggaaggtt tgtgcatgaa ctatacaaga
3061 gtatctgaaa ctaactgttg cctgcatagt catatcgagt gtgcacttac tgtatatctt
3121 ttcatttaca tacttgtatg gaaaatatttt agtctgcact tgtataaata catctttatg
3181 tatttcattt tccataactc actttaattt gactgcaact tgtcttggtg aaatactta
3241 acattataaa acagtaaata atttgttatt ttta
```

---

What is claimed is:

1. A purified filamin A interacting protein 1-like polypeptide consisting of a fragment of SEQ ID NO: 1 selected from the group consisting of amino acids 1-790, 1-650, 1-512, 1-369, 65-893, 127-369, 127-442, 127-512, 127-580, 127-650, 127-720, 127-790, 127-893, 190-893, 310-893, 369-893, and 512-893.

2. A purified polypeptide consisting of an amino acid sequence at least about 95% identical to the purified polypeptide of claim 1, wherein said polypeptide inhibits tumor growth.

3. A purified polypeptide consisting of R1-a fragment of SEQ ID NO:1-R2, wherein R1 or R2 are selected from the group consisting of H, acyl, a targeting amino acid sequence and a targeting molecule, and wherein the fragment of SEQ ID NO:1 is selected from the group consisting of amino acids 1-790, 1-650, 1-512, 1-369, 65-893, 127-369, 127-442, 127-512, 127-580, 127-650, 127-720, 127-790, 127-893, 190-893, 310-893, 369-893, and 512-893.

4. A purified DOC1 polypeptide comprising a fragment of SEQ ID NO: 1, wherein the DOC1 polypeptide is not the full-length DOC1 polypeptide sequence, and the fragment comprises amino acids 127-512 of SEQ ID NO:1.

5. A method of using a filamin A interacting protein 1-like polypeptide to inhibit angiogenesis in a subject, comprising contacting an endothelial cell of the subject with a therapeutically effective amount of the purified polypeptide of claim 1, thus inhibiting angiogenesis.

6. A method of using a filamin A interacting protein 1-like polypeptide to inhibit tumor growth in a subject, comprising contacting a tumor cell of the subject with a therapeutically effective amount of the purified polypeptide of claim 1, thus inhibiting tumor growth.

7. A method of using a filamin A interacting protein 1-like polypeptide to inhibit angiogenesis in a subject, comprising contacting an endothelial cell of the subject with a therapeutically effective amount of the purified polypeptide of claim 3, thus inhibiting angiogenesis.

8. A method of using a filamin A interacting protein 1-like polypeptide to inhibit tumor growth in a subject, comprising contacting a tumor cell of the subject with a therapeutically effective amount of the purified polypeptide of claim 3, thus inhibiting tumor growth.

* * * * *

UNITED STATES PATENT AND TRADEMARK OFFICE
CERTIFICATE OF CORRECTION

PATENT NO.       : 8,501,912 B2                                          Page 1 of 1
APPLICATION NO.  : 12/745279
DATED            : August 6, 2013
INVENTOR(S)      : Libutti et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 238 days.

Signed and Sealed this
Fifteenth Day of September, 2015

Michelle K. Lee
*Director of the United States Patent and Trademark Office*

SEQUENCE LISTING

<160> NUMBER OF SEQ ID NOS: 12

<210> SEQ ID NO 1
<211> LENGTH: 893
<212> TYPE: PRT
<213> ORGANISM: Artificial Sequence
<220> FEATURE:
<223> OTHER INFORMATION: Synthetic construct

<400> SEQUENCE: 1

```
Met Val Val Asp Glu Gln Gln Arg Leu Thr Ala Gln Leu Thr Leu Gln
1               5                   10                  15

Arg Gln Lys Ile Gln Glu Leu Thr Thr Asn Ala Lys Glu Thr His Thr
            20                  25                  30

Lys Leu Ala Leu Ala Glu Ala Arg Val Gln Glu Glu Glu Gln Lys Ala
        35                  40                  45

Thr Arg Leu Glu Lys Glu Leu Gln Thr Gln Thr Thr Lys Phe His Gln
    50                  55                  60

Asp Gln Asp Thr Ile Met Ala Lys Leu Thr Asn Glu Asp Ser Gln Asn
65                  70                  75                  80

Arg Gln Leu Gln Gln Lys Leu Ala Ala Leu Ser Arg Gln Ile Asp Glu
                85                  90                  95

Leu Glu Glu Thr Asn Arg Ser Leu Arg Lys Ala Glu Glu Glu Leu Gln
            100                 105                 110

Asp Ile Lys Glu Lys Ile Ser Lys Gly Glu Tyr Gly Asn Ala Gly Ile
        115                 120                 125

Met Ala Glu Val Glu Glu Leu Arg Lys Arg Val Leu Asp Met Glu Gly
    130                 135                 140

Lys Asp Glu Glu Leu Ile Lys Met Glu Glu Gln Cys Arg Asp Leu Asn
145                 150                 155                 160

Lys Arg Leu Glu Arg Glu Thr Leu Gln Ser Lys Asp Phe Lys Leu Glu
                165                 170                 175

Val Glu Lys Leu Ser Lys Arg Ile Met Ala Leu Glu Lys Leu Glu Asp
            180                 185                 190

Ala Phe Asn Lys Ser Lys Gln Glu Cys Tyr Ser Leu Lys Cys Asn Leu
        195                 200                 205

Glu Lys Glu Arg Met Thr Thr Lys Gln Leu Ser Gln Glu Leu Glu Ser
    210                 215                 220

Leu Lys Val Arg Ile Lys Glu Leu Glu Ala Ile Glu Ser Arg Leu Glu
225                 230                 235                 240

Lys Thr Glu Phe Thr Leu Lys Glu Asp Leu Thr Lys Leu Lys Thr Leu
                245                 250                 255

Thr Val Met Phe Val Asp Glu Arg Lys Thr Met Ser Glu Lys Leu Lys
            260                 265                 270

Lys Thr Glu Asp Lys Leu Gln Ala Ala Ser Ser Gln Leu Gln Val Glu
        275                 280                 285

Gln Asn Lys Val Thr Thr Val Thr Glu Lys Leu Ile Glu Glu Thr Lys
    290                 295                 300

Arg Ala Leu Lys Ser Lys Thr Asp Val Glu Glu Lys Met Tyr Ser Val
305                 310                 315                 320

Thr Lys Glu Arg Asp Asp Leu Lys Asn Lys Leu Lys Ala Glu Glu Glu
                325                 330                 335

Lys Gly Asn Asp Leu Leu Ser Arg Val Asn Met Leu Lys Asn Arg Leu
            340                 345                 350

Gln Ser Leu Glu Ala Ile Glu Lys Asp Phe Leu Lys Asn Lys Leu Asn
        355                 360                 365

Gln Asp Ser Gly Lys Ser Thr Thr Ala Leu His Gln Glu Asn Asn Lys
    370                 375                 380
```

```
Ile Lys Glu Leu Ser Gln Glu Val Glu Arg Leu Lys Leu Lys Leu Lys
385                 390                 395                 400

Asp Met Lys Ala Ile Glu Asp Leu Met Lys Thr Glu Asp Glu Tyr
            405                 410                 415

Glu Thr Leu Glu Arg Arg Tyr Ala Asn Glu Arg Asp Lys Ala Gln Phe
                420                 425                 430

Leu Ser Lys Glu Leu Glu His Val Lys Met Glu Leu Ala Lys Tyr Lys
            435                 440                 445

Leu Ala Glu Lys Thr Glu Thr Ser His Glu Gln Trp Leu Phe Lys Arg
    450                 455                 460

Leu Gln Glu Glu Glu Ala Lys Ser Gly His Leu Ser Arg Glu Val Asp
465                 470                 475                 480

Ala Leu Lys Glu Lys Ile His Glu Tyr Met Ala Thr Glu Asp Leu Ile
                485                 490                 495

Cys His Leu Gln Gly Asp His Ser Val Leu Gln Lys Lys Leu Asn Gln
            500                 505                 510

Gln Glu Asn Arg Asn Arg Asp Leu Gly Arg Glu Ile Glu Asn Leu Thr
            515                 520                 525

Lys Glu Leu Glu Arg Tyr Arg His Phe Ser Lys Ser Leu Arg Pro Ser
    530                 535                 540

Leu Asn Gly Arg Arg Ile Ser Asp Pro Gln Val Phe Ser Lys Glu Val
545                 550                 555                 560

Gln Thr Glu Ala Val Asp Asn Glu Pro Asp Tyr Lys Ser Leu Ile
            565                 570                 575

Pro Leu Glu Arg Ala Val Ile Asn Gly Gln Leu Tyr Glu Glu Ser Glu
                580                 585                 590

Asn Gln Asp Glu Asp Pro Asn Asp Glu Gly Ser Val Leu Ser Phe Lys
            595                 600                 605

Cys Ser Gln Ser Thr Pro Cys Pro Val Asn Arg Lys Leu Trp Ile Pro
    610                 615                 620

Trp Met Lys Ser Lys Glu Gly His Leu Gln Asn Gly Lys Met Gln Thr
625                 630                 635                 640

Lys Pro Asn Ala Asn Phe Val Gln Pro Gly Asp Leu Val Leu Ser His
                645                 650                 655

Thr Pro Gly Gln Pro Leu His Ile Lys Val Thr Pro Asp His Val Gln
            660                 665                 670

Asn Thr Ala Thr Leu Glu Ile Thr Ser Pro Thr Thr Glu Ser Pro His
            675                 680                 685

Ser Tyr Thr Ser Thr Ala Val Ile Pro Asn Cys Gly Thr Pro Lys Gln
    690                 695                 700

Arg Ile Thr Ile Leu Gln Asn Ala Ser Ile Thr Pro Val Lys Ser Lys
705                 710                 715                 720

Thr Ser Thr Glu Asp Leu Met Asn Leu Glu Gln Gly Met Ser Pro Ile
            725                 730                 735

Thr Met Ala Thr Phe Ala Arg Ala Gln Thr Pro Glu Ser Cys Gly Ser
            740                 745                 750

Leu Thr Pro Glu Arg Thr Met Ser Pro Ile Gln Val Leu Ala Val Thr
    755                 760                 765

Gly Ser Ala Ser Ser Pro Glu Gln Gly Arg Ser Pro Glu Pro Thr Glu
770                 775                 780

Ile Ser Ala Lys His Ala Ile Phe Arg Val Ser Pro Asp Arg Gln Ser
785                 790                 795                 800

Ser Trp Gln Phe Gln Arg Ser Asn Ser Asn Ser Ser Ser Val Ile Thr
```

```
                            805                 810                 815
Thr Glu Asp Asn Lys Ile His Ile His Leu Gly Ser Pro Tyr Met Gln
            820                 825                 830

Ala Val Ala Ser Pro Val Arg Pro Ala Ser Pro Ser Ala Pro Leu Gln
            835                 840                 845

Asp Asn Arg Thr Gln Gly Leu Ile Asn Gly Ala Leu Asn Lys Thr Thr
            850                 855                 860

Asn Lys Val Thr Ser Ser Ile Thr Ile Thr Pro Thr Ala Thr Pro Leu
865                 870                 875                 880

Pro Arg Gln Ser Gln Ile Thr Val Ser Asn Ile Tyr Asn
                885                 890

<210> SEQ ID NO 2
<211> LENGTH: 752
<212> TYPE: PRT
<213> ORGANISM: Artificial Sequence
<220> FEATURE:
<223> OTHER INFORMATION: Synthetic construct

<400> SEQUENCE: 2

Met Val Val Asp Glu Gln Gln Arg Leu Thr Ala Gln Leu Thr Leu Gln
1               5                   10                  15

Arg Gln Lys Ile Gln Glu Leu Thr Thr Asn Ala Lys Glu Thr His Thr
            20                  25                  30

Lys Leu Ala Leu Ala Glu Ala Arg Val Gln Glu Glu Glu Gln Lys Ala
        35                  40                  45

Thr Arg Leu Glu Lys Glu Leu Gln Thr Gln Thr Thr Lys Phe His Gln
    50                  55                  60

Asp Gln Asp Thr Ile Met Ala Lys Leu Thr Asn Glu Asp Ser Gln Asn
65              70                  75                  80

Arg Gln Leu Gln Gln Lys Leu Ala Ala Leu Ser Arg Gln Ile Asp Glu
                85                  90                  95

Leu Glu Glu Thr Asn Arg Ser Leu Arg Lys Ala Glu Glu Glu Leu Gln
            100                 105                 110

Asp Ile Lys Glu Lys Ile Ser Lys Gly Glu Tyr Gly Asn Ala Gly Ile
        115                 120                 125

Met Ala Glu Val Glu Glu Leu Ile Lys Met Glu Glu Gln Cys Arg Asp
    130                 135                 140

Leu Asn Lys Arg Leu Glu Arg Glu Thr Leu Gln Ser Lys Asp Phe Lys
145                 150                 155                 160

Leu Glu Val Glu Lys Leu Ser Lys Arg Ile Met Ala Leu Glu Lys Leu
                165                 170                 175

Glu Asp Ala Phe Asn Lys Ser Lys Gln Glu Cys Tyr Ser Leu Lys Cys
            180                 185                 190

Asn Leu Glu Lys Glu Arg Met Thr Thr Lys Gln Leu Ser Gln Glu Leu
        195                 200                 205

Glu Ser Leu Lys Val Arg Ile Lys Glu Leu Glu Ala Ile Glu Ser Arg
    210                 215                 220

Leu Glu Lys Thr Glu Phe Thr Leu Lys Glu Asp Leu Thr Lys Leu Lys
225                 230                 235                 240

Thr Leu Thr Val Met Phe Val Asp Glu Arg Lys Thr Met Ser Glu Lys
                245                 250                 255

Leu Lys Lys Thr Glu Asp Lys Leu Gln Ala Ala Ser Ser Gln Leu Gln
            260                 265                 270

Val Glu Gln Asn Lys Val Thr Thr Val Thr Glu Lys Leu Ile Glu Glu
        275                 280                 285
```

-continued

Thr Lys Arg Ala Leu Lys Ser Lys Thr Asp Val Glu Glu Lys Met Tyr
    290                 295                 300

Ser Val Thr Lys Glu Arg Asp Asp Leu Lys Asn Lys Leu Lys Ala Glu
305                 310                 315                 320

Glu Glu Lys Gly Asn Asp Leu Leu Ser Arg Val Asn Met Leu Lys Asn
                325                 330                 335

Arg Leu Gln Ser Leu Glu Ala Ile Glu Lys Asp Phe Leu Lys Asn Lys
            340                 345                 350

Leu Asn Gln Asp Ser Gly Lys Ser Thr Thr Ala Leu His Gln Glu Asn
        355                 360                 365

Asn Lys Ile Lys Glu Leu Ser Gln Glu Val Glu Arg Leu Lys Leu Lys
    370                 375                 380

Leu Lys Asp Met Lys Ala Ile Glu Asp Leu Met Lys Thr Glu Asp
385                 390                 395                 400

Glu Tyr Glu Thr Leu Glu Arg Arg Tyr Ala Asn Glu Arg Asp Lys Ala
                405                 410                 415

Gln Phe Leu Ser Lys Glu Leu Glu His Val Lys Met Glu Leu Ala Lys
            420                 425                 430

Tyr Lys Leu Ala Glu Lys Thr Glu Thr Ser His Glu Gln Trp Leu Phe
        435                 440                 445

Lys Arg Leu Gln Glu Glu Ala Lys Ser Gly His Leu Ser Arg Glu
    450                 455                 460

Val Asp Ala Leu Lys Glu Lys Ile His Glu Tyr Met Ala Thr Glu Asp
465                 470                 475                 480

Leu Ile Cys His Leu Gln Gly Asp His Ser Val Cys Lys Lys Lys Leu
                485                 490                 495

Asn Gln Gln Glu Asn Arg Asn Arg Asp Leu Gly Arg Glu Ile Glu Asn
            500                 505                 510

Leu Thr Lys Glu Leu Glu Arg Tyr Arg His Phe Ser Lys Ser Leu Arg
        515                 520                 525

Pro Ser Leu Asn Gly Arg Arg Ile Ser Asp Pro Gln Val Phe Ser Lys
    530                 535                 540

Glu Val Gln Thr Glu Ala Val Asp Asn Glu Pro Pro Asp Tyr Lys Ser
545                 550                 555                 560

Leu Ile Pro Leu Glu Arg Ala Val Ile Asn Gly Gln Leu Tyr Glu Glu
                565                 570                 575

Ser Glu Asn Gln Asp Glu Asp Pro Asn Asp Glu Gly Ser Val Leu Ser
            580                 585                 590

Phe Lys Cys Ser Gln Ser Thr Pro Cys Pro Val Asn Arg Lys Leu Trp
        595                 600                 605

Ile Pro Trp Met Lys Ser Lys Glu Gly His Leu Gln Asn Gly Lys Met
    610                 615                 620

Gln Thr Lys Pro Asn Ala Asn Phe Val Gln Pro Gly Asp Leu Val Leu
625                 630                 635                 640

Ser His Thr Pro Gly Gln Pro Leu His Ile Lys Val Thr Pro Asp His
                645                 650                 655

Val Gln Asn Thr Ala Thr Leu Glu Ile Thr Ser Pro Thr Glu Ser
            660                 665                 670

Pro His Ser Tyr Thr Ser Thr Ala Val Ile Pro Asn Cys Gly Thr Pro
        675                 680                 685

Lys Gln Arg Ile Thr Ile Leu Gln Asn Ala Ser Ile Thr Pro Val Lys
    690                 695                 700

Ser Lys Thr Ser Thr Glu Asp Leu Met Asn Leu Glu Gln Gly Met Ser

```
                705                 710                 715                 720
Pro Ile Thr Met Ala Thr Phe Ala Arg Ala Gln Thr Pro Glu Ser Cys
                    725                 730                 735

Gly Ser Leu Thr Pro Glu Arg Thr Met Ser Leu Phe Arg Phe Trp Leu
                    740                 745                 750

<210> SEQ ID NO 3
<211> LENGTH: 1135
<212> TYPE: PRT
<213> ORGANISM: Artificial Sequence
<220> FEATURE:
<223> OTHER INFORMATION: Synthetic construct

<400> SEQUENCE: 3

Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
                20                  25                  30

His Arg Gln Gln Asp Lys Asp Ser Pro Ser Glu Ser Asp Val Ile Leu
            35                  40                  45

Pro Cys Pro Lys Ala Glu Lys Pro His Ser Gly Asn Gly His Gln Ala
        50                  55                  60

Glu Asp Leu Ser Arg Asp Asp Leu Leu Phe Leu Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125

Thr Pro Trp Gln Glu Asp Ile Tyr Glu Lys Pro Met Asn Glu Leu Asp
130                 135                 140

Lys Val Val Glu Lys His Lys Glu Ser Tyr Arg Arg Ile Leu Gly Gln
145                 150                 155                 160

Leu Leu Val Ala Glu Lys Ser Arg Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
        195                 200                 205

Gln Glu Ile Lys Ser Gln Glu Glu Lys Glu Gln Lys Glu Lys Arg
210                 215                 220

Val Thr Thr Leu Lys Glu Glu Leu Thr Lys Leu Lys Ser Phe Ala Leu
225                 230                 235                 240

Met Val Val Asp Glu Gln Gln Arg Leu Thr Ala Gln Leu Thr Leu Gln
                245                 250                 255

Arg Gln Lys Ile Gln Glu Leu Thr Thr Asn Ala Lys Glu Thr His Thr
            260                 265                 270

Lys Leu Ala Leu Ala Glu Ala Arg Val Gln Glu Glu Gln Lys Ala
        275                 280                 285

Thr Arg Leu Glu Lys Glu Leu Gln Thr Gln Thr Lys Phe His Gln
290                 295                 300

Asp Gln Asp Thr Ile Met Ala Lys Leu Thr Asn Glu Asp Ser Gln Asn
305                 310                 315                 320

Arg Gln Leu Gln Gln Lys Leu Ala Ala Leu Ser Arg Gln Ile Asp Glu
                325                 330                 335
```

```
Leu Glu Glu Thr Asn Arg Ser Leu Arg Lys Ala Glu Glu Leu Gln
            340                 345                 350

Asp Ile Lys Glu Lys Ile Ser Lys Gly Glu Tyr Gly Asn Ala Gly Ile
            355                 360                 365

Met Ala Glu Val Glu Glu Leu Arg Lys Arg Val Leu Asp Met Glu Gly
            370                 375                 380

Lys Asp Glu Glu Leu Ile Lys Met Glu Glu Gln Cys Arg Asp Leu Asn
385                 390                 395                 400

Lys Arg Leu Glu Arg Glu Thr Leu Gln Ser Lys Asp Phe Lys Leu Glu
            405                 410                 415

Val Glu Lys Leu Ser Lys Arg Ile Met Ala Leu Glu Lys Leu Glu Asp
            420                 425                 430

Ala Phe Asn Lys Ser Lys Gln Glu Cys Tyr Ser Leu Lys Cys Asn Leu
            435                 440                 445

Glu Lys Glu Arg Met Thr Thr Lys Gln Leu Ser Gln Glu Leu Glu Ser
            450                 455                 460

Leu Lys Val Arg Ile Lys Glu Leu Glu Ala Ile Glu Ser Arg Leu Glu
465                 470                 475                 480

Lys Thr Glu Phe Thr Leu Lys Glu Asp Leu Thr Lys Leu Lys Thr Leu
            485                 490                 495

Thr Val Met Phe Val Asp Glu Arg Lys Thr Met Ser Glu Lys Leu Lys
            500                 505                 510

Lys Thr Glu Asp Lys Leu Gln Ala Ala Ser Ser Gln Leu Gln Val Glu
            515                 520                 525

Gln Asn Lys Val Thr Thr Val Thr Glu Lys Leu Ile Glu Glu Thr Lys
            530                 535                 540

Arg Ala Leu Lys Ser Lys Thr Asp Val Glu Glu Lys Met Tyr Ser Val
545                 550                 555                 560

Thr Lys Glu Arg Asp Asp Leu Lys Asn Lys Leu Lys Ala Glu Glu Glu
            565                 570                 575

Lys Gly Asn Asp Leu Leu Ser Arg Val Asn Met Leu Lys Asn Arg Leu
            580                 585                 590

Gln Ser Leu Glu Ala Ile Glu Lys Asp Phe Leu Lys Asn Lys Leu Asn
            595                 600                 605

Gln Asp Ser Gly Lys Ser Thr Thr Ala Leu His Gln Glu Asn Asn Lys
            610                 615                 620

Ile Lys Glu Leu Ser Gln Glu Val Glu Arg Leu Lys Leu Lys Leu Lys
625                 630                 635                 640

Asp Met Lys Ala Ile Glu Asp Asp Leu Met Lys Thr Glu Asp Glu Tyr
            645                 650                 655

Glu Thr Leu Glu Arg Arg Tyr Ala Asn Glu Arg Asp Lys Ala Gln Phe
            660                 665                 670

Leu Ser Lys Glu Leu Glu His Val Lys Met Glu Leu Ala Lys Tyr Lys
            675                 680                 685

Leu Ala Glu Lys Thr Glu Thr Ser His Glu Gln Trp Leu Phe Lys Arg
            690                 695                 700

Leu Gln Glu Glu Glu Ala Lys Ser Gly His Leu Ser Arg Glu Val Asp
705                 710                 715                 720

Ala Leu Lys Glu Lys Ile His Glu Tyr Met Ala Thr Glu Asp Leu Ile
            725                 730                 735

Cys His Leu Gln Gly Asp His Ser Val Leu Gln Lys Lys Leu Asn Gln
            740                 745                 750

Gln Glu Asn Arg Asn Arg Asp Leu Gly Arg Glu Ile Glu Asn Leu Thr
```

```
                        755                 760                 765

Lys Glu Leu Glu Arg Tyr Arg His Phe Ser Lys Ser Leu Arg Pro Ser
770                 775                 780

Leu Asn Gly Arg Arg Ile Ser Asp Pro Gln Val Phe Ser Lys Glu Val
785                 790                 795                 800

Gln Thr Glu Ala Val Asp Asn Glu Pro Pro Asp Tyr Lys Ser Leu Ile
                805                 810                 815

Pro Leu Glu Arg Ala Val Ile Asn Gly Gln Leu Tyr Glu Glu Ser Glu
                820                 825                 830

Asn Gln Asp Glu Asp Pro Asn Asp Glu Gly Ser Val Leu Ser Phe Lys
                835                 840                 845

Cys Ser Gln Ser Thr Pro Cys Pro Val Asn Arg Lys Leu Trp Ile Pro
                850                 855                 860

Trp Met Lys Ser Lys Glu Gly His Leu Gln Asn Gly Lys Met Gln Thr
865                 870                 875                 880

Lys Pro Asn Ala Asn Phe Val Gln Pro Gly Asp Leu Val Leu Ser His
                885                 890                 895

Thr Pro Gly Gln Pro Leu His Ile Lys Val Thr Pro Asp His Val Gln
                900                 905                 910

Asn Thr Ala Thr Leu Glu Ile Thr Ser Pro Thr Thr Glu Ser Pro His
                915                 920                 925

Ser Tyr Thr Ser Thr Ala Val Ile Pro Asn Cys Gly Thr Pro Lys Gln
                930                 935                 940

Arg Ile Thr Ile Leu Gln Asn Ala Ser Ile Thr Pro Val Lys Ser Lys
945                 950                 955                 960

Thr Ser Thr Glu Asp Leu Met Asn Leu Glu Gln Gly Met Ser Pro Ile
                965                 970                 975

Thr Met Ala Thr Phe Ala Arg Ala Gln Thr Pro Glu Ser Cys Gly Ser
                980                 985                 990

Leu Thr Pro Glu Arg Thr Met Ser Pro Ile Gln Val Leu Ala Val Thr
                995                 1000                1005

Gly Ser Ala Ser Ser Pro Glu Gln Gly Arg Ser Pro Glu Pro Thr
            1010                1015                1020

Glu Ile Ser Ala Lys His Ala Ile Phe Arg Val Ser Pro Asp Arg
            1025                1030                1035

Gln Ser Ser Trp Gln Phe Gln Arg Ser Asn Ser Asn Ser Ser Ser
            1040                1045                1050

Val Ile Thr Thr Glu Asp Asn Lys Ile His Ile His Leu Gly Ser
            1055                1060                1065

Pro Tyr Met Gln Ala Val Ala Ser Pro Val Arg Pro Ala Ser Pro
            1070                1075                1080

Ser Ala Pro Leu Gln Asp Asn Arg Thr Gln Gly Leu Ile Asn Gly
            1085                1090                1095

Ala Leu Asn Lys Thr Thr Asn Lys Val Thr Ser Ser Ile Thr Ile
            1100                1105                1110

Thr Pro Thr Ala Thr Pro Leu Pro Arg Gln Ser Gln Ile Thr Val
            1115                1120                1125

Glu Pro Leu Leu Leu Pro His
            1130                1135

<210> SEQ ID NO 4
<211> LENGTH: 1133
<212> TYPE: PRT
<213> ORGANISM: Artificial Sequence
<220> FEATURE:
```

<223> OTHER INFORMATION: Synthetic construct

<400> SEQUENCE: 4

```
Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
            20                  25                  30

His Arg Gln Gln Asp Lys Asp Ser Pro Ser Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Asp Leu Leu Phe Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125

Thr Pro Trp Gln Glu Asp Ile Tyr Glu Lys Pro Met Asn Glu Leu Asp
    130                 135                 140

Lys Val Val Glu Lys His Lys Glu Ser Tyr Arg Arg Ile Leu Gly Gln
145                 150                 155                 160

Leu Leu Val Ala Glu Lys Ser Arg Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
        195                 200                 205

Gln Glu Ile Lys Ser Gln Glu Glu Lys Glu Lys Glu Lys Arg
    210                 215                 220

Val Thr Thr Leu Lys Glu Glu Leu Thr Lys Leu Lys Ser Phe Ala Leu
225                 230                 235                 240

Met Val Val Asp Glu Gln Gln Arg Leu Thr Ala Gln Leu Thr Leu Gln
                245                 250                 255

Arg Gln Lys Ile Gln Glu Leu Thr Thr Asn Ala Lys Glu Thr His Thr
            260                 265                 270

Lys Leu Ala Leu Ala Glu Ala Arg Val Gln Glu Glu Glu Gln Lys Ala
        275                 280                 285

Thr Arg Leu Glu Lys Glu Leu Gln Thr Gln Thr Lys Phe His Gln
    290                 295                 300

Asp Gln Asp Thr Ile Met Ala Lys Leu Thr Asn Glu Asp Ser Gln Asn
305                 310                 315                 320

Arg Gln Leu Gln Gln Lys Leu Ala Ala Leu Ser Arg Gln Ile Asp Glu
                325                 330                 335

Leu Glu Glu Thr Asn Arg Ser Leu Arg Lys Ala Glu Glu Glu Leu Gln
            340                 345                 350

Asp Ile Lys Glu Lys Ile Ser Lys Gly Glu Tyr Gly Asn Ala Gly Ile
        355                 360                 365

Met Ala Glu Val Glu Glu Leu Arg Lys Arg Val Leu Asp Met Glu Gly
    370                 375                 380

Lys Asp Glu Glu Leu Ile Lys Met Glu Glu Cys Arg Asp Leu Asn
385                 390                 395                 400

Lys Arg Leu Glu Arg Glu Thr Leu Gln Ser Lys Asp Phe Lys Leu Glu
```

-continued

```
                405                 410                 415
Val Glu Lys Leu Ser Lys Arg Ile Met Ala Leu Glu Lys Leu Glu Asp
                420                 425                 430

Ala Phe Asn Lys Ser Lys Gln Glu Cys Tyr Ser Leu Lys Cys Asn Leu
            435                 440                 445

Glu Lys Glu Arg Met Thr Thr Lys Gln Leu Ser Gln Glu Leu Glu Ser
        450                 455                 460

Leu Lys Val Arg Ile Lys Glu Leu Glu Ala Ile Glu Ser Arg Leu Glu
465                 470                 475                 480

Lys Thr Glu Phe Thr Leu Lys Glu Asp Leu Thr Lys Leu Lys Thr Leu
                485                 490                 495

Thr Val Met Phe Val Asp Glu Arg Lys Thr Met Ser Glu Lys Leu Lys
            500                 505                 510

Lys Thr Glu Asp Lys Leu Gln Ala Ala Ser Ser Gln Leu Gln Val Glu
        515                 520                 525

Gln Asn Lys Val Thr Thr Val Thr Glu Lys Leu Ile Glu Glu Thr Lys
    530                 535                 540

Arg Ala Leu Lys Ser Lys Thr Asp Val Glu Glu Lys Met Tyr Ser Val
545                 550                 555                 560

Thr Lys Glu Arg Asp Asp Leu Lys Asn Lys Leu Lys Ala Glu Glu Glu
                565                 570                 575

Lys Gly Asn Asp Leu Leu Ser Arg Val Asn Met Leu Lys Asn Arg Leu
            580                 585                 590

Gln Ser Leu Glu Ala Ile Glu Lys Asp Phe Leu Lys Asn Lys Leu Asn
        595                 600                 605

Gln Asp Ser Gly Lys Ser Thr Thr Ala Leu His Gln Glu Asn Asn Lys
    610                 615                 620

Ile Lys Glu Leu Ser Gln Glu Val Glu Arg Leu Lys Leu Lys Leu Lys
625                 630                 635                 640

Asp Met Lys Ala Ile Glu Asp Asp Leu Met Lys Thr Glu Asp Glu Tyr
                645                 650                 655

Glu Thr Leu Glu Arg Arg Tyr Ala Asn Glu Arg Asp Lys Ala Gln Phe
            660                 665                 670

Leu Ser Lys Glu Leu Glu His Val Lys Met Glu Leu Ala Lys Tyr Lys
        675                 680                 685

Leu Ala Glu Lys Thr Glu Thr Ser His Glu Gln Trp Leu Phe Lys Arg
    690                 695                 700

Leu Gln Glu Glu Glu Ala Lys Ser Gly His Leu Ser Arg Glu Val Asp
705                 710                 715                 720

Ala Leu Lys Glu Lys Ile His Glu Tyr Met Ala Thr Glu Asp Leu Ile
                725                 730                 735

Cys His Leu Gln Gly Asp His Ser Val Leu Gln Lys Lys Leu Asn Gln
            740                 745                 750

Gln Glu Asn Arg Asn Arg Asp Leu Gly Arg Glu Ile Glu Asn Leu Thr
        755                 760                 765

Lys Glu Leu Glu Arg Tyr Arg His Phe Ser Lys Ser Leu Arg Pro Ser
    770                 775                 780

Leu Asn Gly Arg Arg Ile Ser Asp Pro Gln Val Phe Ser Lys Glu Val
785                 790                 795                 800

Gln Thr Glu Ala Val Asp Asn Glu Pro Pro Asp Tyr Lys Ser Leu Ile
                805                 810                 815

Pro Leu Glu Arg Ala Val Ile Asn Gly Gln Leu Tyr Glu Glu Ser Glu
            820                 825                 830
```

Asn Gln Asp Glu Asp Pro Asn Asp Glu Gly Ser Val Leu Ser Phe Lys
        835                 840                 845

Cys Ser Gln Ser Thr Pro Cys Pro Val Asn Arg Lys Leu Trp Ile Pro
    850                 855                 860

Trp Met Lys Ser Lys Glu Gly His Leu Gln Asn Gly Lys Met Gln Thr
865                 870                 875                 880

Lys Pro Asn Ala Asn Phe Val Gln Pro Gly Asp Leu Val Leu Ser His
                885                 890                 895

Thr Pro Gly Gln Pro Leu His Ile Lys Val Thr Pro Asp His Val Gln
            900                 905                 910

Asn Thr Ala Thr Leu Glu Ile Thr Ser Pro Thr Glu Ser Pro His
        915                 920                 925

Ser Tyr Thr Ser Thr Ala Val Ile Pro Asn Cys Gly Thr Pro Lys Gln
    930                 935                 940

Arg Ile Thr Ile Leu Gln Asn Ala Ser Ile Thr Pro Val Lys Ser Lys
945                 950                 955                 960

Thr Ser Thr Glu Asp Leu Met Asn Leu Glu Gln Gly Met Ser Pro Ile
                965                 970                 975

Thr Met Ala Thr Phe Ala Arg Ala Gln Thr Pro Glu Ser Cys Gly Ser
            980                 985                 990

Leu Thr Pro Glu Arg Thr Met Ser Pro Ile Gln Val Leu Ala Val Thr
        995                 1000                1005

Gly Ser Ala Ser Ser Pro Glu Gln Gly Arg Ser Pro Glu Pro Thr
    1010                1015                1020

Glu Ile Ser Ala Lys His Ala Ile Phe Arg Val Ser Pro Asp Arg
    1025                1030                1035

Gln Ser Ser Trp Gln Phe Gln Arg Ser Asn Ser Asn Ser Ser Ser
    1040                1045                1050

Val Ile Thr Thr Glu Asp Asn Lys Ile His Ile His Leu Gly Ser
    1055                1060                1065

Pro Tyr Met Gln Ala Val Ala Ser Pro Val Arg Pro Ala Ser Pro
    1070                1075                1080

Ser Ala Pro Leu Gln Asp Asn Arg Thr Gln Gly Leu Ile Asn Gly
    1085                1090                1095

Ala Leu Asn Lys Thr Thr Asn Lys Val Thr Ser Ser Ile Thr Ile
    1100                1105                1110

Thr Pro Thr Ala Thr Pro Leu Pro Arg Gln Ser Gln Ile Thr Val
    1115                1120                1125

Ser Asn Ile Tyr Asn
    1130

<210> SEQ ID NO 5
<211> LENGTH: 21
<212> TYPE: DNA
<213> ORGANISM: Artificial Sequence
<220> FEATURE:
<223> OTHER INFORMATION: Synthetic construct

<400> SEQUENCE: 5
agcgtaacca aggagagaga t                                             21

<210> SEQ ID NO 6
<211> LENGTH: 21
<212> TYPE: DNA
<213> ORGANISM: Artificial Sequence
<220> FEATURE:
<223> OTHER INFORMATION: Synthetic construct

<400> SEQUENCE: 6
attcattcat tcattcacca t                                              21

<210> SEQ ID NO 7
<211> LENGTH: 3274
<212> TYPE: DNA
<213> ORGANISM: Artificial Sequence
<220> FEATURE:
<223> OTHER INFORMATION: Synthetic construct

<400> SEQUENCE: 7
ataggccggg cgcgctcagc gccccgctcg cattgttcgg gcgactctcg gagcgcgcac      60
agtcggctcg cagcgcggca ctacagcggc cccggcccgg ccccgcccg gccccggcgc     120 aggcagttca gattaaagaa gctaattgat caagaaatca agtctcagga ggagaaggag    180
caagaaaagg agaaaagggt caccaccctg aaagaggagc tgaccaagct gaagtctttt    240
gctttgatgg tggtggatga acagcaaagg ctgacggcac agctcaccct tcaaagacag    300
aaaatccaag agctgaccac aaatgcaaag gaaacacata ccaaactagc ccttgctgaa    360
gccagagttc aggaggaaga gcagaaggca ccagactag agaaggaact gcaaacgcag     420
accacaaagt ttcaccaaga ccaagacaca attatggcga agctcaccaa tgaggacagt    480
caaaatcgcc agcttcaaca aaagctggca gcactcagcc ggcagattga tgagttagaa    540
gagacaaaca ggtctttacg aaaagcagaa gaggagctgc aagatataaa agaaaaaatc    600
agtaagggag aatatggaaa cgctggtatc atggctgaag tggaagagct caggaaacgt    660
gtgctagata tggaagggaa agatgaagag ctcataaaaa tggaggagca gtgcagagat    720
ctcaataaga ggcttgaaag ggagacgtta cagagtaaaa ctttaaaact agaggttgaa    780
aaactcagta aagaattat ggctctggaa aagttagaag acgctttcaa caaaagcaaa    840
caagaatgct actctctgaa atgcaattta gaaaagaaa ggatgaccac aaagcagttg     900
tctcaagaac tggagagttt aaaagtaagg atcaagagc tagaagccat tgaaagtcgg    960
ctagaaaaga cagaattcac tctaaaagag gatttaacta aactgaaaac attaactgtg   1020
atgtttgtag atgaacggaa acaatgagt gaaaaattaa agaaactga agataaatta     1080 caagctgctt cttctcagct tcaagtggag caaaataaag taacaacagt tactgagaag   1140
ttaattgagg aaactaaaag ggcgctcaag tccaaaaccg atgtagaaga aaagatgtac   1200
agcgtaacca aggagagaga tgatttaaaa aacaaattga agcggaaga agagaaagga    1260 aatgatctcc tgtcaagagt taatatgttg aaaaataggc ttcaatcatt ggaagcaatt   1320
gagaaagatt tcctaaaaaa caaattaat caagactctg ggaaatccac aacagcatta    1380
caccaagaaa acaataagat taaggagctc tctcaagaag tggaaagact gaaactgaag   1440
ctaaaggaca tgaaagccat tgaggatgac ctcatgaaaa cagaagatga atatgagact   1500
ctagaacgaa ggtatgctaa tgaacgagac aaagctcaat ttttatctaa agagctagaa   1560
catgttaaaa tggaacttgc taagtacaag ttagcagaaa agacagagac cagccatgaa   1620
caatggcttt tcaaaaggct tcaagaagaa gaagctaagt cagggcacct ctcaagagaa   1680
gtggatgcat taaagagaa aattcatgaa tacatggcaa ctgaagacct aatatgtcac   1740
ctccagggag atcactcagt cctgcaaaaa aactaaatc aacaagaaaa caggaacaga   1800
gatttaggaa gagagattga aaacctcact aaggagttag agaggtaccg gcatttcagt   1860
aagagcctca ggcctagtct caatggaaga agaatttccg atcctcaagt attttctaaa   1920
gaagttcaga cagaagcagt agacaatgaa ccacctgatt acaagagcct cattcctctg   1980

-continued

```
gaacgtgcag tcatcaatgg tcagttatat gaggagagtg agaatcaaga cgaggaccct    2040
aatgatgagg gatctgtgct gtccttcaaa tgcagccagt ctactccatg tcctgttaac    2100
agaaagctat ggattccctg gatgaaatcc aaggagggcc atcttcagaa tggaaaatg     2160 caaactaaac ccaatgccaa ctttgtgcaa cctggagatc tagtcctaag ccacacacct    2220
gggcagccac ttcatataaa ggttactcca gaccatgtac aaaacacagc cactcttgaa    2280
atcacaagtc caaccacaga gagtcctcac tcttacacga gtactgcagt gataccgaac    2340
tgtggcacgc caaagcaaag gataaccatc ctccaaaacg cctccataac accagtaaag    2400
tccaaaacct ctaccgaaga cctcatgaat ttagaacaag gcatgtcccc aattaccatg    2460
gcaacctttg ccagagcaca gaccccagag tcttgtggtt ctctaactcc agaaaggaca    2520 atgtcccta ttcaggtttt ggctgtgact ggttcagcta gctctcctga gcagggacgc     2580
tccccagaac caacagaaat cagtgccaag catgcgatat tcagagtctc cccagaccgg    2640
cagtcatcat ggcagtttca gcgttcaaac agcaatagct caagtgtgat aactactgag    2700
gataataaaa tccacattca cttaggaagt ccttacatgc aagctgtagc cagccctgtg    2760
agacctgcca gcccttcagc accactgcag gataaccgaa ctcaaggctt aattaacggg    2820
gcactaaaca aaacaaccaa taaagtcacc agcagtatta ctatcacacc aacagccaca    2880
cctcttcctc gacaatcaca aattacagta agtaatatat ataactgacc acgctcaccc    2940
tcatccagtc catactgata ttttgcaag gaactcaatc ctttttaat catccctcca      3000 tatcccccaa gactgactga actcgtactt tgggaaggtt tgtgcatgaa ctatacaaga    3060
gtatctgaaa ctaactgttg cctgcatagt catatcgagt gtgcacttac tgtatatctt    3120
ttcatttaca tacttgtatg gaaaatattt agtctgcact tgtataaata catctttatg    3180
tatttcattt tccataactc actttaattt gactgcaact tgtcttggtg aaatacttta    3240
acattataaa acagtaaata atttgttatt ttta                                3274
```

<210> SEQ ID NO 8
<211> LENGTH: 893
<212> TYPE: PRT
<213> ORGANISM: Artificial Sequence
<220> FEATURE:
<223> OTHER INFORMATION: Synthetic construct

<400> SEQUENCE: 8

```
Met Val Val Asp Glu Gln Gln Arg Leu Thr Ala Gln Leu Thr Leu Gln
1               5                   10                  15

Arg Gln Lys Val Gln Glu Leu Thr Thr Asn Ala Lys Glu Thr His Thr
            20                  25                  30

Lys Leu Ala Leu Ala Glu Ala Arg Val Gln Glu Glu Glu Gln Lys Ala
        35                  40                  45

Thr Arg Leu Glu Lys Glu Leu Gln Thr Gln Thr Lys Phe His Gln
    50                  55                  60

Asp Gln Asp Thr Ile Met Ala Lys Leu Thr Asn Glu Asp Ser Gln Asn
65                  70                  75                  80

Arg Gln Leu Gln Gln Lys Leu Ala Ala Leu Ser Arg Gln Ile Asp Glu
                85                  90                  95

Leu Glu Glu Thr Asn Arg Ser Leu Arg Lys Ala Glu Glu Leu Gln
            100                 105                 110

Asp Ile Lys Glu Lys Ile Ser Lys Gly Glu Tyr Gly Asn Ala Gly Ile
        115                 120                 125

Met Ala Glu Val Glu Glu Leu Arg Lys Arg Val Leu Asp Met Glu Gly
    130                 135                 140
```

```
Lys Asp Glu Glu Leu Ile Lys Met Glu Glu Gln Cys Arg Asp Leu Asn
145                 150                 155                 160

Lys Arg Leu Glu Arg Glu Thr Leu Gln Ser Lys Asp Phe Lys Leu Glu
                165                 170                 175

Val Glu Lys Leu Ser Lys Arg Ile Met Ala Leu Glu Lys Leu Glu Asp
            180                 185                 190

Ala Phe Asn Lys Ser Lys Gln Glu Cys Tyr Ser Leu Lys Cys Asn Leu
        195                 200                 205

Glu Lys Glu Arg Met Thr Thr Lys Gln Leu Ser Gln Glu Leu Glu Ser
    210                 215                 220

Leu Lys Val Arg Ile Lys Glu Leu Glu Ala Ile Glu Ser Arg Leu Glu
225                 230                 235                 240

Lys Thr Glu Phe Thr Leu Lys Glu Asp Leu Thr Lys Leu Lys Thr Leu
                245                 250                 255

Thr Val Met Phe Val Asp Glu Arg Lys Thr Met Ser Glu Lys Leu Lys
            260                 265                 270

Lys Thr Glu Asp Lys Leu Gln Ala Ala Ser Ser Gln Leu Gln Val Glu
        275                 280                 285

Gln Asn Lys Val Thr Thr Val Thr Glu Lys Leu Ile Glu Glu Thr Lys
    290                 295                 300

Arg Ala Leu Lys Ser Lys Thr Asp Val Glu Glu Lys Met Tyr Ser Val
305                 310                 315                 320

Thr Lys Glu Arg Asp Asp Leu Lys Asn Lys Leu Lys Ala Glu Glu Glu
                325                 330                 335

Lys Gly Asn Asp Leu Leu Ser Arg Val Asn Met Leu Lys Asn Arg Leu
            340                 345                 350

Gln Ser Leu Glu Ala Ile Glu Lys Asp Phe Leu Lys Asn Lys Leu Asn
        355                 360                 365

Gln Asp Ser Gly Lys Ser Thr Thr Ala Leu His Gln Glu Asn Asn Lys
    370                 375                 380

Ile Lys Glu Leu Ser Gln Glu Val Glu Arg Leu Lys Leu Lys Leu Lys
385                 390                 395                 400

Asp Met Lys Ala Ile Glu Asp Asp Leu Met Lys Thr Glu Asp Glu Tyr
                405                 410                 415

Glu Thr Leu Glu Arg Arg Tyr Ala Asn Glu Arg Asp Lys Ala Gln Phe
            420                 425                 430

Leu Ser Lys Glu Leu Glu His Val Lys Met Glu Leu Ala Lys Tyr Lys
        435                 440                 445

Leu Ala Glu Lys Thr Glu Thr Ser His Glu Gln Trp Leu Phe Lys Arg
    450                 455                 460

Leu Gln Glu Glu Glu Ala Lys Ser Gly His Leu Ser Arg Glu Val Asp
465                 470                 475                 480

Ala Leu Lys Glu Lys Ile His Glu Tyr Met Ala Thr Glu Asp Leu Ile
                485                 490                 495

Cys His Leu Gln Gly Asp His Ser Val Leu Gln Lys Lys Leu Asn Gln
            500                 505                 510

Gln Glu Asn Arg Asn Arg Asp Leu Gly Arg Glu Ile Glu Asn Leu Thr
        515                 520                 525

Lys Glu Leu Glu Arg Tyr Arg His Phe Ser Lys Ser Leu Arg Pro Ser
    530                 535                 540

Leu Asn Gly Arg Arg Ile Ser Asp Pro Gln Val Phe Ser Lys Glu Val
545                 550                 555                 560

Gln Thr Glu Ala Val Asp Asn Glu Pro Pro Asp Tyr Lys Ser Leu Ile
```

```
                565                 570                 575
Pro Leu Glu Arg Ala Val Ile Asn Gly Gln Leu Tyr Glu Glu Ser Glu
            580                 585                 590

Asn Gln Asp Glu Asp Pro Asn Asp Glu Gly Ser Val Leu Ser Phe Lys
        595                 600                 605

Cys Ser Gln Ser Thr Pro Cys Pro Val Asn Arg Lys Leu Trp Ile Pro
    610                 615                 620

Trp Met Lys Ser Lys Glu Gly His Leu Gln Asn Gly Lys Met Gln Thr
625                 630                 635                 640

Lys Pro Asn Ala Asn Phe Val Gln Pro Gly Asp Leu Val Leu Ser His
            645                 650                 655

Thr Pro Gly Gln Pro Leu His Ile Lys Val Thr Pro Asp His Val Gln
        660                 665                 670

Asn Thr Ala Thr Leu Glu Ile Thr Ser Pro Thr Thr Glu Ser Pro His
    675                 680                 685

Ser Tyr Thr Ser Thr Ala Val Ile Pro Asn Cys Gly Thr Pro Lys Gln
690                 695                 700

Arg Ile Thr Ile Leu Gln Asn Ala Ser Ile Thr Pro Val Lys Ser Lys
705                 710                 715                 720

Thr Ser Thr Glu Asp Leu Met Asn Leu Glu Gln Gly Met Ser Pro Ile
            725                 730                 735

Thr Met Ala Thr Phe Ala Arg Ala Gln Thr Pro Glu Ser Cys Gly Ser
        740                 745                 750

Leu Thr Pro Glu Arg Thr Met Ser Pro Ile Gln Val Leu Ala Val Thr
    755                 760                 765

Gly Ser Ala Ser Ser Pro Glu Gln Gly Arg Ser Pro Glu Pro Thr Glu
770                 775                 780

Ile Ser Ala Lys His Ala Ile Phe Arg Val Ser Pro Asp Arg Gln Ser
785                 790                 795                 800

Ser Trp Gln Phe Gln Arg Ser Asn Ser Asn Ser Ser Ser Val Ile Thr
            805                 810                 815

Thr Glu Asp Asn Lys Ile His Ile His Leu Gly Ser Pro Tyr Met Gln
        820                 825                 830

Ala Val Ala Ser Pro Val Arg Pro Ala Ser Pro Ser Ala Pro Leu Gln
    835                 840                 845

Asp Asn Arg Thr Gln Gly Leu Ile Asn Gly Ala Leu Asn Lys Thr Thr
850                 855                 860

Asn Lys Val Thr Ser Ser Ile Thr Ile Thr Pro Thr Ala Thr Pro Leu
865                 870                 875                 880

Pro Arg Gln Ser Gln Ile Thr Val Ser Asn Ile Tyr Asn
            885                 890

<210> SEQ ID NO 9
<211> LENGTH: 21
<212> TYPE: DNA
<213> ORGANISM: Artificial Sequence
<220> FEATURE:
<223> OTHER INFORMATION: Synthetic construct

<400> SEQUENCE: 9
aacgctggta tcatggctga a                                           21

<210> SEQ ID NO 10
<211> LENGTH: 22
<212> TYPE: DNA
<213> ORGANISM: Artificial Sequence
<220> FEATURE:
```

```
<223> OTHER INFORMATION: Synthetic construct

<400> SEQUENCE: 10
atctctgcac tgctcctcca tt                                           22

<210> SEQ ID NO 11
<211> LENGTH: 22
<212> TYPE: DNA
<213> ORGANISM: Artificial Sequence
<220> FEATURE:
<223> OTHER INFORMATION: Synthetic construct

<400> SEQUENCE: 11
tcaccagggc tgcttttaac tc                                           22

<210> SEQ ID NO 12
<211> LENGTH: 26
<212> TYPE: DNA
<213> ORGANISM: Artificial Sequence
<220> FEATURE:
<223> OTHER INFORMATION: Synthetic construct

<400> SEQUENCE: 12
ggaatcatat tggaacatgt aaacca                                       26
```